(12) United States Patent
Jain et al.

(10) Patent No.: US 9,957,230 B2
(45) Date of Patent: May 1, 2018

(54) SYNERGISTIC COMPOSITIONS

(71) Applicant: Cadila Healthcare Limited, Ahmedabad (IN)

(72) Inventors: Mukul R. Jain, Gujarat (IN); Suresh Giri, Gujarat (IN); Himanshu M. Kothari, Gujarat (IN); Kaushik Banerjee, Gujarat (IN); Rashmikant Kachhiya, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 0 days. days.

(21) Appl. No.: 15/594,795

(22) Filed: May 15, 2017

(65) Prior Publication Data

US 2017/0320823 A1 Nov. 9, 2017

Related U.S. Application Data

(62) Division of application No. 14/783,336, filed as application No. PCT/IN2014/000445 on Jul. 4, 2014, now Pat. No. 9,656,954.

(30) Foreign Application Priority Data

Jul. 5, 2013 (IN) .......................... 2276/MUM/2013

(51) Int. Cl.
| | |
|---|---|
| C07D 207/333 | (2006.01) |
| C07D 233/58 | (2006.01) |
| A61K 31/155 | (2006.01) |
| C07C 279/14 | (2006.01) |
| C07C 229/26 | (2006.01) |
| C07C 217/60 | (2006.01) |
| C07C 215/40 | (2006.01) |
| C07C 215/12 | (2006.01) |
| C07C 215/10 | (2006.01) |
| C07C 211/51 | (2006.01) |

(Continued)

(52) U.S. Cl.
CPC ........ *C07D 207/333* (2013.01); *A61K 31/155* (2013.01); *A61K 31/40* (2013.01); *A61K 31/4015* (2013.01); *A61K 31/4985* (2013.01); *A61K 31/505* (2013.01); *A61K 31/64* (2013.01); *A61K 38/26* (2013.01); *A61K 45/06* (2013.01); *C07C 211/11* (2013.01); *C07C 211/27* (2013.01); *C07C 211/30* (2013.01); *C07C 211/35* (2013.01); *C07C 211/51* (2013.01); *C07C 215/10* (2013.01); *C07C 215/12* (2013.01); *C07C 215/40* (2013.01); *C07C 217/60* (2013.01); *C07C 229/26* (2013.01); *C07C 279/14* (2013.01); *C07D 233/58* (2013.01); *C07D 295/027* (2013.01); *A61K 2300/00* (2013.01); *C07C 2601/14* (2017.05)

(58) Field of Classification Search
None
See application file for complete search history.

(56) References Cited

U.S. PATENT DOCUMENTS

| | | |
|---|---|---|
| 4,231,938 A | 11/1980 | Monaghan et al. |
| 4,346,227 A | 8/1982 | Terahara et al. |

(Continued)

FOREIGN PATENT DOCUMENTS

| | | |
|---|---|---|
| EP | 1586571 A1 | 10/2005 |
| IN | 1910/MUM/2013 | 12/2014 |

(Continued)

OTHER PUBLICATIONS

Berge et al., Pharmaceutical Salts, Jan. 1977, Journal of Pharmaceutical Sciences, vol. 66, No. 1, 1-19.*

(Continued)

*Primary Examiner* — Kristin A Vajda
(74) *Attorney, Agent, or Firm* — Goodwin Procter LLP

(57) ABSTRACT

The present invention describes a synergistic composition comprising of one or more statins, or one or more dipeptidyl peptidase IV (DPP IV) inhibitor or one or more biguanide antihyperglycaemic agent and a PPAR agonist of formula (1a) for the treatment of diabetes, especially non-insulin dependent diabetes (NIDDM) or Type 2 diabetes and conditions associated with diabetes mellitus and to compositions suitable for use in such method. The invention also describes the preparation of such compositions. The present invention also relates to certain novel salts of the PPAR agonist of formula (I), processes for the preparation of these novel salts and use thereof.

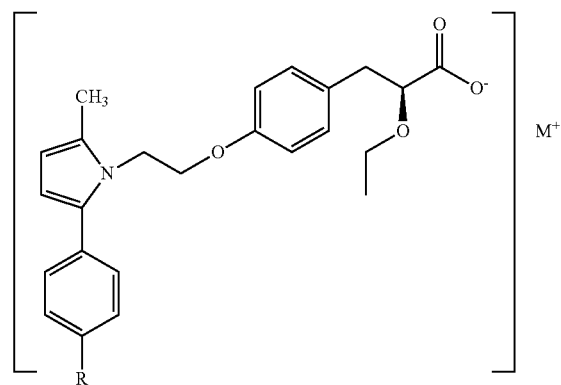

Formula (I)

16 Claims, 14 Drawing Sheets

(51) Int. Cl.

| | | |
|---|---|---|
| C07C 211/35 | (2006.01) | |
| C07C 211/30 | (2006.01) | |
| C07C 211/27 | (2006.01) | |
| C07C 211/11 | (2006.01) | |
| A61K 45/06 | (2006.01) | |
| A61K 38/26 | (2006.01) | |
| A61K 31/64 | (2006.01) | |
| A61K 31/505 | (2006.01) | |
| A61K 31/4985 | (2006.01) | |
| A61K 31/4015 | (2006.01) | |
| A61K 31/40 | (2006.01) | |
| C07D 295/027 | (2006.01) | |

(56) References Cited

U.S. PATENT DOCUMENTS

| | | | |
|---|---|---|---|
| 4,444,784 | A | 4/1984 | Hoffman et al. |
| 5,273,995 | A | 12/1993 | Roth |
| 5,354,772 | A | 10/1994 | Kathawala |
| 6,166,063 | A | 12/2000 | Villhauer |
| 6,395,767 | B2 | 5/2002 | Robl et al. |
| 6,699,871 | B2 | 3/2004 | Edmondson et al. |
| 6,987,123 | B2 | 1/2006 | Lohray et al. |
| 7,041,837 | B2 | 5/2006 | Lohray et al. |
| 7,323,491 | B2 | 1/2008 | Lohray et al. |
| 7,407,955 | B2 | 8/2008 | Himmelsbach et al. |
| 8,110,598 | B2 | 2/2012 | Lohray et al. |
| 8,212,057 | B2 | 7/2012 | Lohray et al. |
| 8,558,009 | B2 | 10/2013 | Lohray et al. |
| 8,772,342 | B2 | 7/2014 | Darteil et al. |
| 9,610,277 | B2 | 4/2017 | Patel et al. |
| 9,656,954 | B2 | 5/2017 | Jain et al. |
| 9,783,495 | B2 | 10/2017 | Pandey et al. |
| 9,814,697 | B2 | 11/2017 | Patel et al. |
| 2003/0199498 | A1 | 10/2003 | Lohray et al. |
| 2003/0236254 | A1 | 12/2003 | Lohray et al. |
| 2007/0238776 | A1 | 10/2007 | Lohray et al. |
| 2009/0196923 | A1 | 8/2009 | Mandal et al. |
| 2011/0275669 | A1 | 11/2011 | Lohray et al. |
| 2012/0121729 | A1 | 5/2012 | Paterson et al. |
| 2013/0338209 | A1 | 12/2013 | Gambhire et al. |
| 2016/0068484 | A1 | 3/2016 | Jain et al. |
| 2016/0107989 | A1 | 4/2016 | Dwivedi et al. |
| 2016/0136131 | A1 | 5/2016 | Patel et al. |
| 2016/0166539 | A1 | 6/2016 | Patel et al. |
| 2016/0194280 | A1 | 7/2016 | Dwivedi et al. |
| 2016/0207884 | A1 | 7/2016 | Dwivedi et al. |
| 2017/0087127 | A1 | 3/2017 | Patel et al. |
| 2017/0088514 | A1 | 3/2017 | Gambhire et al. |
| 2017/0144968 | A1 | 5/2017 | Dwivedi et al. |
| 2017/0266158 | A1 | 9/2017 | Patel et al. |

FOREIGN PATENT DOCUMENTS

| | | | | |
|---|---|---|---|---|
| WO | WO-91/19702 | A1 | 12/1991 | |
| WO | WO-94/01420 | A1 | 1/1994 | |
| WO | WO-94/13650 | A1 | 6/1994 | |
| WO | WO-95/03038 | A1 | 2/1995 | |
| WO | WO-95/17394 | A1 | 6/1995 | |
| WO | WO-96/04260 | A1 | 2/1996 | |
| WO | WO-96/04261 | A1 | 2/1996 | |
| WO | WO-96/33998 | A1 | 10/1996 | |
| WO | WO-97/25042 | A1 | 7/1997 | |
| WO | WO-97/36579 | A1 | 10/1997 | |
| WO | WO-98/28534 | A1 | 7/1998 | |
| WO | WO-99/08501 | A2 | 2/1999 | |
| WO | WO-99/16758 | A1 | 4/1999 | |
| WO | WO-99/19313 | A1 | 4/1999 | |
| WO | WO-99/20614 | A1 | 4/1999 | |
| WO | WO-00/23417 | A1 | 4/2000 | |
| WO | WO-00/23445 | A1 | 4/2000 | |
| WO | WO-00/23451 | A1 | 4/2000 | |
| WO | WO-01/53257 | A2 | 7/2001 | |
| WO | WO-02/24625 | A2 | 3/2002 | |
| WO | WO-03/009841 | A1 | 2/2003 | |
| WO | WO-2005/031335 | A1 | 4/2005 | |
| WO | WO 2012104869 | A1 * | 8/2012 | ............ A61K 31/40 |
| WO | WO-2014/174524 | A1 | 10/2014 | |
| WO | WO-2014/195967 | A2 | 12/2014 | |
| WO | WO-2015/001573 | A1 | 1/2015 | |
| WO | WO-2015/011730 | A1 | 1/2015 | |
| WO | WO-2015/029066 | A1 | 3/2015 | |
| WO | WO-2015/033357 | A2 | 3/2015 | |

OTHER PUBLICATIONS

"Sodium Stearyl Fumarate", obtained on Jun. 23, 2015. Retrieved from the Internet: <URL: https://www.medicinescomplete.com/me/excipients/current/ . . . >, 4 pages.

Anonymous "IND Minutes draft 19 07 12" Retrieved on Oct. 15, 2013 from the Internet from URL: http://www.docstoc.com/docs/145152750/IND-Minutes-draft-19-07-12 (1 page).

Anonymous "Lipaglyn$^{TM}$ Discovery, Development & Preclinical Studies" Retrieved on Oct. 15, 2013 from the Internet from URL: http://webcache.googleusercontent.com/search?q=cache:RGrhmY0HM3sJ:lipaglyn.com/downloads/Lipaglyn_Preclinical_Studies.ppsx (25 pages).

Anonymous International Nonproprietary Names for Pharmaceutical Substances (INN); Jan. 1, 2012; Retrieved from the Internet: URL: http://www.who.int/medicines/publications/druginformation/issues/PL_108.pdf; Retrieved on Oct. 10-15, 2013; pp. 401-471.

Ansel etal. "Pharmaceutical Dosage Forms and Drug Delivery Systems, Seventh Edition" 1999, pp. 88-92.

Augustyns, K. et al. "Inhibitors of proline-specific dipeptidyl peptidases: DPP IV inhibitors as a novel approach for the treatment of Type 2 diabetes," *Expert Opin. Ther. Patents*, (2005) vol. 15, No. 10, pp. 1387-1407.

Barb et al. (2016) "Pharmacological management of nonalcoholic fatty liver disease" Metabolism Clinical and Experimental 65:1183-1195.

Berger et al. (2005) "PPARs: Therapeutic targets for metabolic disease TRENDS in Pharmacological Sciences" 26(5): 244-251.

Bharate, S. et al. "Interactions and incompatibilities of pharmaceutical excipients with active pharmaceutical ingredients: a comprehensive review." *J. Excipient and Food Chem.* (2010) vol. 1, No. 3, pp. 3-26.

Brenna, E. et al. "Enzyme-mediated synthesis of EEHP and EMHP, useful pharmaceutical intermediates of PPAR agonists" *Tetrahedron: Asymmetry* (2009) vol. 20 pp. 2594-2599.

Cairns, D. (editor) "Essentials of Pharmaceutical Chemistry, Fourth Edition" 2012, p. 14.

Chou et al. (2013) "Metrelepin: First Global Approval" Drugs 73:989-997.

Deeg et al. (2007) "Pioglitazone and Rosiglitazone Have Different Effects on Serum Lipoprotein Particle Concentrations and Sizes in Patients With Type 2 Diabetes and Dyslipidemia" Diabetes Care 30(10):2458-2464.

Demuth, H.-U. et al. "Type 2 diabetes—Therapy with dipeptidyl peptidase IV inhibitors," *Biochim. Blophys. Acta*, 1751 (2005) pp. 33-44.

Fan, W. W and Evans, R. "PPARs and ERRs: molecular mediators of mitochondrial metabolism" *Curr. Opin. Cell Bio.* (2015) vol. 33, pp. 49-54.

FDA News Release—FDA Approves Egrifta to treat Lipodystrophy in HIV Patients; downloaded from www.fda.gov/NewsEvents/Newsroom/PressAnnouncements/ucm233516.htm on Sep. 7, 2016 (2 pages).

Gennaro et al. "Remington's Pharmaceutical Sciences, 19th Edition" (1995) Mack Publishing, pp. 1380-1383.

Giri et al. "Efficacy of Saroglitazar, a Novel PPAR Agonist in a Mouse Model of Non-Alcoholic Steatohepatitis" Poster No. 2011, Keystone Symposia Conference, Mar. 22-27, 2015 at Whistler, British Colombia, Canada.

Hadigan, C. et al. "Metabolic Effects of Rosiglitazone in HIV Lipodystrophy: A Randomized, Controlled Trial," *Ann. Internal Med.* (2004) vol. 140, No. 10, pp. 788-794. (Abstract Only).

(56) References Cited

OTHER PUBLICATIONS

IND Committee: "Minutes of IND Committee Meeting Held on Jul. 19, 2012" Retrieved on Oct. 15, 2013 from the Internet from URL: http://www.docstoc.com/docs/145152750/IND-Minutes-draft-19-07-12 (2 pages).
International Preliminary Report on Patentability dated Aug. 15, 2013 for International Application No. PCT/IN2012/000069 (5 pages).
International Preliminary Report on Patentability dated Dec. 1, 2015 for International Patent Application No. PCT/IN2014/000367 (9 pages).
International Preliminary Report on Patentability dated Jul. 9, 2015 for International Application No. PCT/IN2013/000391 (9 pages).
International Preliminary Report on Patentability dated Mar. 1, 2016 for Application No. PCT/IN2014/000551 (7 pages).
International Preliminary Report on Patentability dated Mar. 8, 2016 for International Patent Application No. PCT/IN2014/000584 (10 pages).
International Preliminary Report on Patentability dated Oct. 6, 2015 for International Patent Application No. PCT/IN2014/000445 (7 pages).
International Preliminary Report on Patentability dated Oct. 9, 2015 for International Application No. PCT/IN2014/000489 (7 pages).
International Search Report and Written Opinion dated Dec. 19, 2014 for Application No. PCT/IN2014/000551 (11 pages).
International Search Report and Written Opinion dated Dec. 23, 2014 for International Patent Application No. PCT/IN2014/000445 (10 pages).
International Search Report and Written Opinion dated Feb. 2, 2015 for International Patent Application No. PCT/IN2014/000367 (14 pages).
International Search Report and Written Opinion dated Mar. 23, 2015 for Application No. PCT/IN2014/000584 (14 pages).
International Search Report and Written Opinion dated Nov. 20, 2013 for International Application No. PCT/IN2013/000391 (13 pages).
International Search Report and Written Opinion dated Nov. 20, 2014 for International Application No. PCT/IN2014/000489 (10 pages).
International Search Report dated May 9, 2012 for International Application No. PCT/IN2012/000069 (3 pages).
Jain et al. "Saroglitazar Shows Therapeutic Benefits in Mouse Model of Non-alcoholic Fatty Liver Disease (NAFLD) and Non-alcoholic Steatohepatitis (NASH)" Poster No. 1957-P, 75th Scientific Session—ADA, Jun. 5-9, 2015, Boston, MA, USA.
Jani, R. H. et al. "Pharmacokinetics, Safety, and Tolerability of Saroglitazar (ZYH1), a Predominantly PPARα Agonist with Moderate PPARγ Agonist Activity in Healthy Human Subjects" *Clin. Drug Investig.* (2013) vol. 33, pp. 809-816.
Jani, R. H. et al. "A Multicenter, Prospective, Randomized, Double-Blind Study to Evaluate the Safety and Efficacy of Saroglitazar 2 and 4 mg Compared with Placebo in Type 2 Diabetes Mellitus Patients Having Hypertriglyceridemia Not Controlled with Atorvastatin Therapy (Press VI)," Diabetes Technology & Therapeutics, (2014) vol. 16, No. 2, pp. 63-71.
Jani, R. H. etal. "A Prospective Randomized, Double Blind, Placebo Controlled Study to Evaluate the Safety,Tolerability and Pharmacokinetics of ZYH1 Following Once a Day (OD) Oral Administrations up to 10 Days in Healthy Volunteers," *Diabetes* (2009) vol. 58, No. Suppl. 1, p. A569.
LaBrecque, D. et al. "World Gastroenterology Organisation, Global Guidelines: Nonalcoholic Fatty Liver disease and Nonalcoholic Steatohepatitis (long version)" World Gastroenterology Organisation (2012) 29 pages.
Lieberman, et al. "Pharmaceutical Dosage Forms: Tablets, vol. 1, 2nd Edition" (1989) Marcel Dekker Inc., pp. 111-114.
Macallan, D. C. et al. "Treatment of Altered Body Composition in HIV Associated Lipodystrophy: Comparison of Rosiglitazone, Pravastatin, and Recombinant Human Growth Hormone," *HIV Clinical Trials*, (2008) vol. 9, Issue 4, pp. 254-268. (Abstract Only).
Package Insert for ACTOS (pioglitazone) tablets for oral use (2013).
Package Insert for AVANDIA (rosiglitazone maleate) Tablets (2008).
Pai, V. et al. "A Multicenter, Prospective, Randomized, Double-blind Study to Evaluate the Safety and Efficacy of Saroglitazar 2 and 4 mg Compared to Pioglitazone 45 mg in Diabetic Dyslipidemia (PRESS V)." *J. Diabetes Sci. Technol.* (2014) vol. 8, No. 1, pp. 132-141.
Palomer et al. (2016) "PPARβ/δ and lipid metabolism in the heart" Biochemica et Biophysica Acta 1861:1569-1578.
Ramirez, T. et al. "Structural Correlates of PPAR Agonist Rescue of Experimental Chronic Alcohol-Induced Steatohepatitis," *J. Clin. Exper. Pathology* (2012) vol. 2, No. 4, pp. 1-9.
Response to Written Opinion filed on May 21, 2015 for International Application No. PCT/IN2014/000489 (6 pages).
Seo, Y. S. et al. "PPAR agonists treatment is effective in a nonalcoholic fatty liver disease animal model by modulating fatty-acid metabolic enzymes" *J. Gatroenterology Hepatology* (2008) vol. 23, No. 1, pp. 102-109.
Tungsiripat, M. et al. "Rosiglitazone improves lipoatrophy in patients receiving thymidine-sparing regimens," *AIDS*, (2010) vol. 24, pp. 1291-1298.
van Wijk, J. P. H. et al. "Comparison of Rosiglitazone and Metformin for Treating HIV Lipodystrophy: A Randomized Trial," *Ann. Internal Med.* (2005) vol. 143, No. 5, pp. 337-346.
Written Opinion of the International Searching Authority dated May 9, 2012 for International Application No. PCT/IN2012/000069 (4 pages).
Yessoufou et al. (2010) "Multifaceted roles of peroxisome proliferator-activated receptors (PPARs) at the cellular and whole organism levels" Swiss Medical Weekly 140:w13071.
Pharmatrans Sanaq AG "LubriSanaq" Dated Feb. 5, 2008. (2 pages).
Lemoine, M. et al. "Steatohepatitis (fatty liver) Is Associated With Increased Hepatic Expression of SREBP-1 in HIV-Infected Patients With Antiretroviral Therapy-Linked Lipodystrophy," Abstract from 55th Annual Meeting of the American Association for the Study of Liver Diseases, Oct. 29 to Nov 2, 2004; Printed from http://www.natap.org/2004/AASLD/aasld_10.htm. (8 pages).
Bugianesi, E. et al. "Insulin Resistance: A Metabolic Pathway to Chronic Liver Disease," *Hepatology* (2005) vol. 42, No. 5, pp. 987-1000.
Angulo, P. "GI Epidemiology: nonalcoholic fatty liver disease," *Aliment. Pharmacol. Ther.* (2007) vol. 25, No. 8, pp. 883-889.
Acdisol Product Overview (year 2005).
USPTO Trademark Database Entry for AEROSIL, 1966.
Boulet, L-P. "Influence of Comorbid Conditions on Asthma" *European Respiratory Journal* (2009) vol. 33, pp. 897-906.
Chatila, W. M. et al. "Comorbidities in Chronic Obstructive Pulmonary Disease" *Proc. Am. Thorac. Soc.* (2008) vol. 5, pp. 549-555.
Jackson, K. "No Benefit from Ezetimibe in NASH" in Medpage Today (Jun. 2015).
Prescribing Information for Zetia® (ezetimibe; year 2012).
Rakoski, M. et al. "Meta-analysis: Insulin Sensitizers for the Treatment of Non-alcoholic Steatohepatitis" *Aliment. Pharmacol. Ther.* (2010) vol. 32, pp. 1211-1221.
Boettcher, E. et al. "Meta-analysis: pioglitazone improves liver histology and fibrosis in patients with non-alcoholic steatohepatitis," *Aliment. Pharmacol. Ther.* (2012) vol. 35, No. 1, pp. 66-75. (Abstract Only, Retrieved from https://www.ncbi.nih.gov/pubmed/22050199).
Herrine, S. K. "Nonalcoholic Steatohepatitis (NASH)" *Merck ManuaL* (Revised May 2016) Retrieved on Sep. 13, 2017 from http://www.merckmanuals.com/professional/hepatic-and-biliary-disorders/approach-to-the-patient-with-liver-disease/nonalcoholic-steatohepatitis-nash. (3 pages).

\* cited by examiner

SYNERGISTIC COMPOSITIONS

CROSS-REFERENCE TO RELATED APPLICATIONS

This application is a divisional of U.S. patent application Ser. No. 14/783,336, filed Oct. 8, 2015, which is the national stage of International (PCT) Patent Application Serial No. PCT/IN2014/000445, filed Jul. 4, 2014, which claims the benefit of and priority to Indian Patent Application No. 2276/MUM/2013, filed Jul. 5, 2013; the contents of U.S. patent application Ser. No. 14/783,336 and International Patent Application Serial No. PCT/IN2014/000445 are hereby incorporated by reference in their entirety.

FIELD OF THE INVENTION

The present invention describes a synergistic composition comprising of one or more statins, or one or more dipeptidyl peptidase IV (DPP IV) inhibitor(s) or one or more biguanide antihyperglycaemic agent and a PPAR agonist of formula (I) for the treatment of diabetes, especially non-insulin dependent diabetes (NIDDM) or Type 2 diabetes and conditions associated with diabetes mellitus and to compositions suitable for use in such conditions. The invention also describes the preparation of such compositions. The present invention also relates to certain novel salts of the PPAR agonist of formula (I), processes for the preparation of these novel salts and use thereof.

BACKGROUND OF THE INVENTION

Hyperlipidemia has been recognized as the major risk factor in causing cardiovascular diseases due to atherosclerosis. Atherosclerosis and other such peripheral vascular diseases affect the quality of life of a large population in the world. The therapy aims to lower the elevated plasma LDL cholesterol, low-density lipoprotein and plasma triglycerides in order to prevent or reduce the risk of occurrence of cardiovascular diseases.

Hypolipidemic agents which are PPAR modulators have been disclosed in WO 91/19702, WO 94/01420, WO 94/13650, WO 95/03038, WO 95/17394, WO 96/04260, WO 96/04261, WO 96/33998, WO 97/25042, WO 97/36579, WO 98/28534, WO 99/08501, WO 99/16758, WO 99/19313, WO99/20614, WO 00/23417, WO 00/23445, WO 00/23451, WO 01/53257.

WO 03009841 discloses compounds of the following general formula:

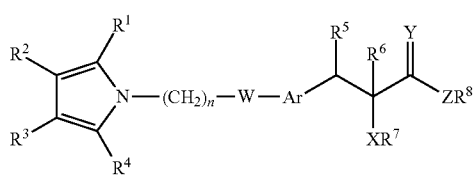

These compounds are reported to be hypolipidemic agents. WO 03009841 also discloses certain salts including the sodium salt of some of the compounds disclosed therein. However, these salts either were difficult to isolate due to rapid degradation or were poorly absorbed limiting their efficacy and possibility of further development or were found to degrade on long term storage thereby also limiting their suitability for further pharmaceutical development. It has surprisingly now been found that certain compounds and their selected salts are effective in further pharmaceutical development and are also efficacious than some of the earlier known salts.

The present invention provides synergistic composition of certain hypolipidemic and hypocholesterolemic compounds of formula (Ia) wherein 'M$^{+}$' represents Calcium, Magnesium, Sodium, Potassium, Zinc and Lithium, preferably Magnesium, in combination with one or more therapeutic agents as described herein after.

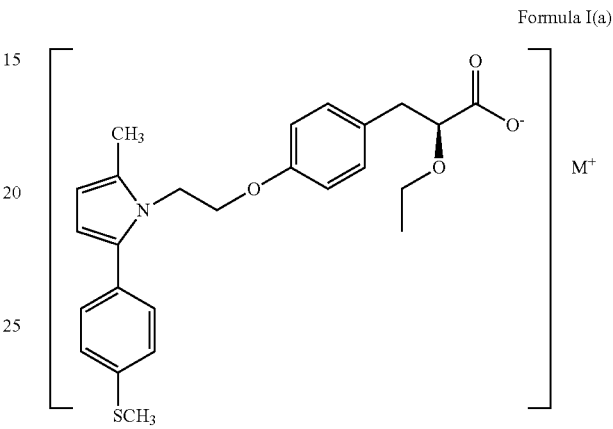

Formula I(a)

In another embodiment the present invention describes compounds of formula (I)

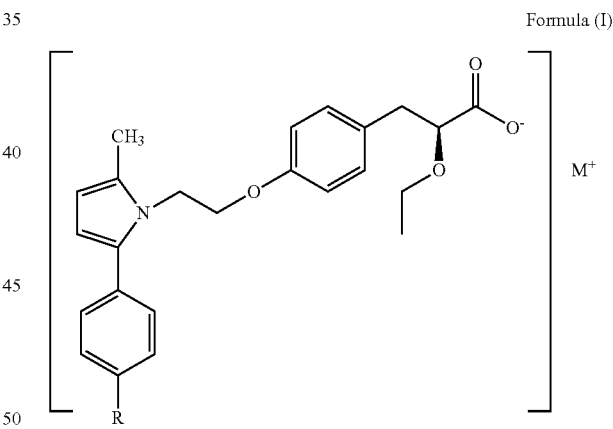

Formula (I)

wherein 'R' is selected from hydroxy, hydroxyalkyl, acyl, alkoxy, alkylthio, thioalkyl, aryloxy, arylthio and M$^{+}$ represents Calcium, Magnesium, Sodium, Potassium, Zinc, Lithium, L-Arginine, Tromethamine, L-Lysine, Meglumine, Benethamine, Piperazine, Benzylamine, Dibenzylamine, Dicyclohexylamine, Diethylamine, Diphenylamine, α-naphthylamine, O-phenylenediamine, 1,3-Diaminopropane, (S)-α-naphthylethylamine, (S)-3-methoxyphenylethylamine, (S)-4-methoxyphenylethylamine, (S)-4-chlorophenylethylamine, (S)-4-methylphenylethylamine, Cinchonine, Cinchonidine, (−)-Quinine, Benzathine, Ethanolamine, Diethanol amine, Triethanolamine, imidazole, Diethylamine, Ethylenediamine, Choline, Epolamine, Morpholine 4-(2-hydroxyethyl), N—N-diethylethanolamine, Deanol, Hydrabamine, Betaine, Ammonia, Adamantanamine, L-Adamantanmethylamine & Tritylamine. Many of these salts also shows certain superior pharmaceutical &/or chemical properties.

In a preferred embodiment, 'R' represents thioalkyl or alkoxy or hydroxyalkyl group; in a still preferred embodiment, 'R' represents —SCH$_3$ or —OCH$_3$ group.

Type 2 diabetes is a chronic and progressive disease arising from a complex pathophysiology involving the dual endocrine defects of insulin resistance and impaired insulin secretion. The treatment of Type 2 diabetes typically begins with diet and exercise, followed by oral antidiabetic monotherapy. For many patients, these regimens do not sufficiently control glycemia during long-term treatment, leading to a requirement for combination therapy within several years following diagnosis. However, co-prescription of two or more oral antidiabetic drugs may result in treatment regimens that are complex and difficult for many patients to follow. Combining two or more oral antidiabetic agents into a single tablet provides a potential means of delivering combination therapy without adding to the complexity of patients daily regimens. Such formulations have been well accepted in other disease indications, such as hypertension (HYZAAR™ which is a combination of losartan potassium and hydrochlorothiazide) and cholesterol lowering (VYTORIN™ which is a combination of simvastatin and ezetimibe). The selection of effective and well-tolerated treatments is a key step in the design of a combination tablet. Moreover, it is essential that the components have complementary mechanisms of action and compatible pharmacokinetic profiles. Examples of marketed combination tablets containing two oral antidiabetic agents include Glucovance™ (Metformin and Glyburide), Avandamet™ (Metformin and Rosiglitazone), Metaglip™ (Metformin and Glipizide), Janumet™ (contains Sitagliptin and Metformin), etc.

Biguanide antihyperglycaemic agents are commonly used in the treatment of NIDDM (or Type II diabetes). 1,1-Dimethylbiguanidine (or Metformin) is an example of a biguanide antihyperglycaemic agent.

Metformin represents the only oral antidiabetic agent proven to reduce the total burden of microvascular and macrovascular diabetic complications and to prolong the lives of Type 2 diabetic patients. Furthermore, metformin treatment is often associated with reductions in body weight in overweight patients and with improvements in lipid profiles in dyslipidemic patients. Metformin hydrochloride is marketed as either immediate-release or extended-release formulations with tablet dosage strengths of 500, 750, 850, and 1000 milligrams. Extended-release formulations of metformin have advantages over immediate-release in terms of affording a more uniform maintenance of blood plasma active drug concentrations and providing better patient compliance by reducing the frequency of administration required.

It has now surprisingly been found that Compound of formula (Ia) in combination with a biguanide antihyperglycaemic agent such as Metformin provides a particularly beneficial effect on glycaemic control with no observed adverse effects; such combination is therefore particularly useful for the treatment of diabetes mellitus, especially Type II diabetes and conditions associated with diabetes mellitus.

Statins (or HMG-CoA reductase inhibitors) are a class of drugs used to lower cholesterol levels by inhibiting the enzyme HMG-CoA reductase, which plays a central role in the production of cholesterol in the liver. Increased cholesterol levels have been associated with cardiovascular diseases and statins are therefore used in the prevention of these diseases. Several statins have been approved for the treatment of cardiovascular diseases including Lovastatin (MEVACOR, U.S. Pat. No. 4,231,938), Simvastatin (ZOCOR; U.S. Pat. No. 4,444,784), Pravastatin sodium salt (PRAVACHOL; U.S. Pat. No. 4,346,227), Fluvastatin sodium salt (LESCOL; U.S. Pat. No. 5,354,772), Atorvastatin calcium salt (LIPITOR; U.S. Pat. No. 5,273,995) and Rosuvastatin calcium (CRESTOR; US RE37314). The above mentioned publications are incorporated herein by reference.

The present invention is also based on the surprising finding that statins can increase the activity of PPAR agonists compound of formula (Ia) and can be used to treat or prevent dyslipidemia and type 2 diabetes and other disorders responsive to PPAR activators or PPAR activation, without increasing the risk for side effects such as rhabdomylosis, fluid retention, edema, or congestive heart failure. Dipeptidyl peptidase-4 (DPP-4) inhibitors represent a novel class of agents that are being developed for the treatment or improvement in glycemic control in patients with Type 2 diabetes. Specific DPP-4 inhibitors currently in clinical trials for the treatment of Type 2 diabetes include sitagliptin phosphate (MK-0431), vildagliptin (LAF-237), saxagliptin (BMS-47718), alogliptin (X), carmegliptin (X), melogliptin (X), dutogliptin (X), denagliptin (X), linagliptin (X), P93/01 (Prosidion), SYR322 (Takeda), GSK 823093, Roche 0730699, TS021 (Taisho), E3024 (Eisai), and PHX-1149 (Phenomix). For example, oral administration of vildagliptin or sitagliptin to human Type 2 diabetics has been found to reduce fasting glucose and postprandial glucose excursion in association with significantly reduced HbA$_{1c}$ levels. Several reviews on the application of DPP-4 inhibitors for the treatment of Type 2 diabetes, have been published such as H.-U. Demuth, et al., "Type 2 diabetes—Therapy with dipeptidyl peptidase IV inhibitors, Biochim. Biophys. Acta, 1751: 33-44 (2005), K. Augustyns, et al., "Inhibitors of proline-specific dipeptidyl peptidases: DPP IV inhibitors as a novel approach for the treatment of Type 2 diabetes," Expert Opin. Ther. Patents, 15: 1387-1407 (2005), etc.

DPP-4 inhibitors currently approved or in clinical trials for the treatment of Type 2 diabetes include sitagliptin phosphate, vildagliptin, saxagliptin, alogliptin, carmegliptin, melogliptin, dutogliptin, denagliptin, linagliptin, P93/01 (Prosidion), SYR322 (Takeda), GSK 823093, Roche 0730699, TS021 (Taisho), E3024 (Eisai), PHX-1149 (Phenomix), etc.

Sitagliptin free base and pharmaceutically acceptable salts thereof are disclosed in U.S. Pat. No. 6,699,871 the contents of which are hereby incorporated by reference in their entirety. Crystalline sitagliptin phosphate monohydrate is disclosed in international patent publication WO 2005/0031335.

Vildagliptin is the generic name for (S)-1-[(3-hydroxy-1-adamantyl)amino]acetyl-2-cyano-pyrrolidine. Vildagliptin is specifically disclosed in U.S. Pat. No. 6,166,063, the contents of which are hereby incorporated by reference in their entirety.

Saxagliptin is a methanoprolinenitrile derivative specifically disclosed in U.S. Pat. No. 6,395,767, the contents of which are hereby incorporated by reference in their entirety.

Alogliptin is a DPP-IV inhibitor under investigation for the treatment of type 2 diabetes, specifically disclosed in EP 1586571 the contents of which are hereby incorporated by reference in their entirety.

Linagliptin is a DPP-IV inhibitor approved for the treatment of type 2 diabetes specifically disclosed in U.S. Pat. No. 7,407,955 the contents of which are hereby incorporated by reference in their entirety.

Other DPP-IV inhibitors useful in the formulation of the present invention include, but are not limited to alogliptin, carmegliptin, melogliptin, dutogliptin, and denagliptin.

The present invention is also based on the surprising finding that DPP IV inhibitors can increase the activity of PPAR agonists of formula (Ia) and can be used to treat or prevent dyslipidemia and type 2 diabetes and other disorders responsive to PPAR activators or PPAR activation, without increasing the risk for side effects such as rhabdomylosis, fluid retention, edema, or congestive heart failure.

Sodium-glucose co-transporter 2 (SGLT2) inhibitors are a new class of diabetic medications indicated only for the treatment of type 2 diabetes. SGLT-2 inhibitors work by reducing the amount of glucose being absorbed in the kidneys so that it is passed out in the urine and also by reducing the amount of glucose in blood. Their use in clinical practice is associated with improved glycaemic control, weight loss and a low risk of hypoglycaemia. Dapagliflozin, Canagliflozin, Empagliflozin are some of the SGLT-2 inhibitors which are either approved or are under clinical trials for the treatment of diabetes and associated disorders.

The present invention is also based on the surprising finding that SGLT-2 inhibitors can increase the activity of PPAR agonist compounds of formula (Ia) and can be used to treat or prevent dyslipidemia and type 2 diabetes and other disorders responsive to PPAR activators or PPAR activation, without increasing the risk for side effects such as rhabdomylosis, fluid retention, edema, or congestive heart failure.

Glucagon-like-peptide-1 agonists or GLP-1 agonists are a class of drugs for the treatment of type 2 diabetes. Glucagon-like peptide-1 (GLP-1) enhances glucose-dependent insulin secretion following its release into the circulation from the gut. GLP-1 receptor agonists enhance glucose-dependent insulin secretion by the pancreatic beta-cell, suppress inappropriately elevated glucagon secretion, and slow gastric emptying. GLP-1 agonists are used for diabetes type 2 combined with other anti-diabetic drugs.

The present invention is also based on the surprising finding that GLP-1 receptor agonists can increase the activity of PPAR agonist compounds of formula (Ia) and can be used to treat or prevent dyslipidemia and type 2 diabetes and other disorders responsive to PPAR activators or PPAR activation, without increasing the risk for side effects such as rhabdomylosis, fluid retention, edema, or congestive heart failure.

The acid of Formula (I) is a thick liquid which is difficult to isolate, purify and develop into a pharmaceutical formulation. It is therefore necessary to isolate the acid in a form that is easy to purify, handle, scale up and develop into suitable pharmaceutical formulation. Conversion into suitable salts represent one such means.

Salts often improve physical and biological characteristics of mother compounds without modifying primary pharmacological activity, based on mechanism of action of the compound. Thus there is a continuing need to obtain new salts of Formula (I) having improved physical and/or chemical properties. The present invention satisfies this need by providing new salts of Formula (I).

In an embodiment, the new salts of Formula (I) provide a new opportunity to improve the performance of the synthesis of the Formula (I) acid in a chemically and chirally pure form. These new salts are produced in solid state, have improved characteristics such as stability and flowability, and are therefore easy to handle in an industrial scale. This makes these new salts suitable as intermediates for preparing the compound of formula (I) in a chemically and chirally pure form, though some of these salts may not be pharmaceutically useful. Some of these salts can also have superior biological properties over one or more of the known salts of Formula (I).

These salts may be present either in substantially crystalline or amorphous forms or may be present as partially crystalline forms. In a preferred embodiment the salts are present in crystalline form. In another preferred embodiment, the salts are present in an amorphous form. In another embodiment, the salts are present in non-solvated/unsolvated form or in a solvent free form. In another embodiment, the salts are present in solvated/hydrated form.

SUMMARY OF THE PRESENT INVENTION

In one embodiment of the present invention is provided a synergistic composition comprising compound of formula (Ia) with one or more DPP IV inhibitors for the treatment of diabetes and its associated diseases.

In a further embodiment of the invention is provided a synergistic composition comprising compound of formula (Ia) with one or more statins for the treatment of diabetes and its associated diseases.

In a still further embodiment of the invention is provided a synergistic composition comprising compound of formula (Ia) with one or more biguanides antihyperglycaemic agent for the treatment of diabetes and its associated diseases.

In another embodiment is provided a pharmaceutical composition comprising the compound of formula (Ia) and one or more therapeutic agents from those described above for the treatment of humans and other mammals in need thereof. In another embodiment is provided a pharmaceutical composition comprising the compound of formula (Ia) and with one or more thiazolidinedione antihyperglycaemic agents for the treatment of humans and other mammals in need thereof.

In another embodiment is provided a pharmaceutical composition comprising the compound of formula (Ia) and with one or more sulfonylureas for the treatment of humans and other mammals in need thereof.

In another embodiment is provided a pharmaceutical composition comprising the compound of formula (Ia) and with one or more SGLT-2 inhibitors for the treatment of humans and other mammals in need thereof.

In another embodiment is provided a pharmaceutical composition comprising the compound of formula (Ia) and with one or more insulin sensitizers for the treatment of humans and other mammals in need thereof.

In a still further embodiment is provided a pharmaceutical composition comprising, the therapeutically effective amount of compound of formula (Ia), prepared according to the present invention, along with at least one suitable pharmaceutically acceptable carrier, diluents, vehicle or excipient.

In another embodiment the present invention also provides novel salts of compound of Formula (I).

In another embodiment the present invention also provides processes for the preparation of novel salts of compound of Formula (I).

DETAILED DESCRIPTION OF THE INVENTION

Figure 1:
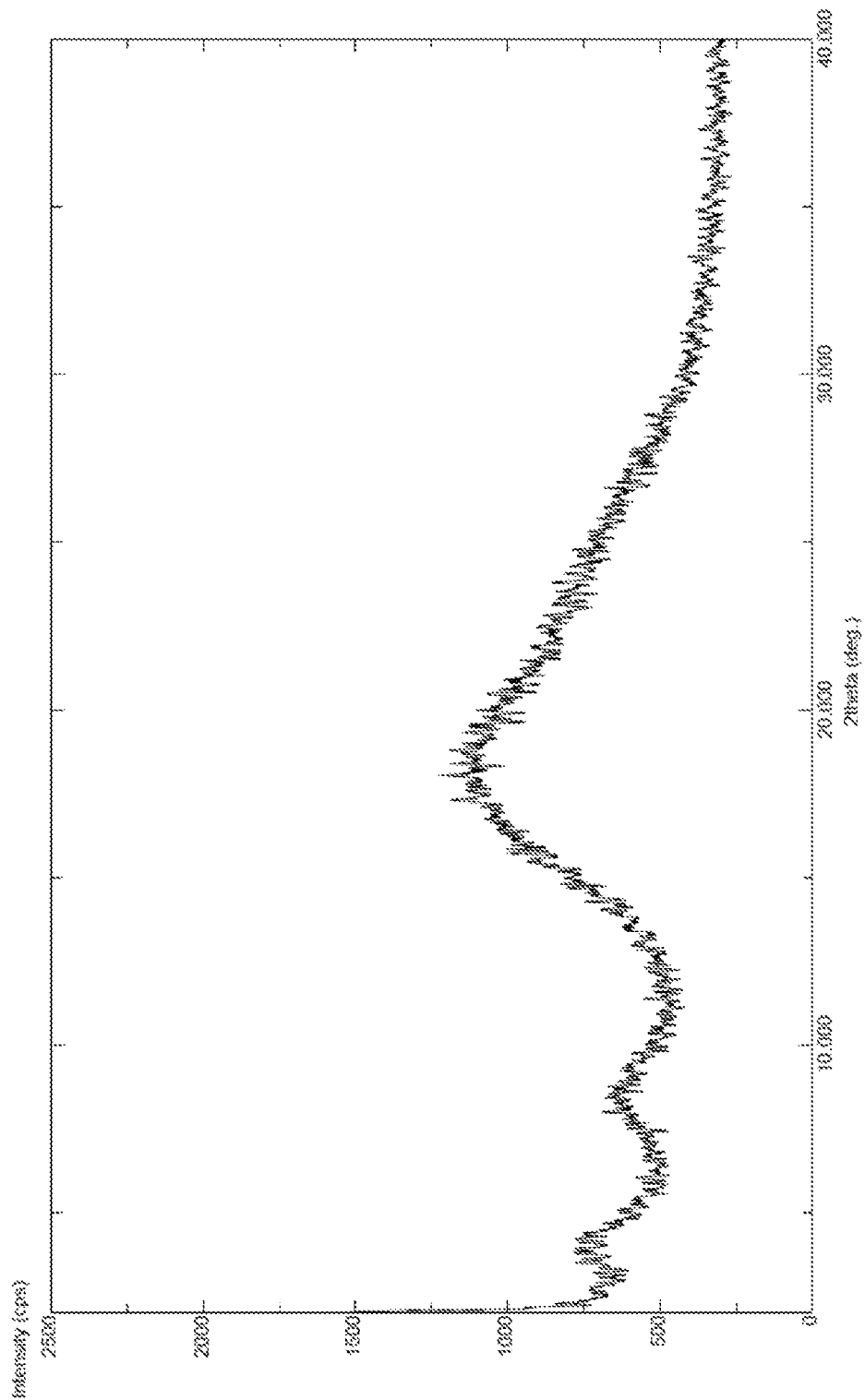
FIG. 1 is a powder X-ray diffraction (XRPD) pattern of amorphous form of (S) 2-Ethoxy-3-(4-{2-[2-methyl-5-(4-methylthiophenyl)-pyrrol-1-yl]-ethoxy}-phenyl)-propionic acid Calcium salt according to the present invention.
Figure 2:
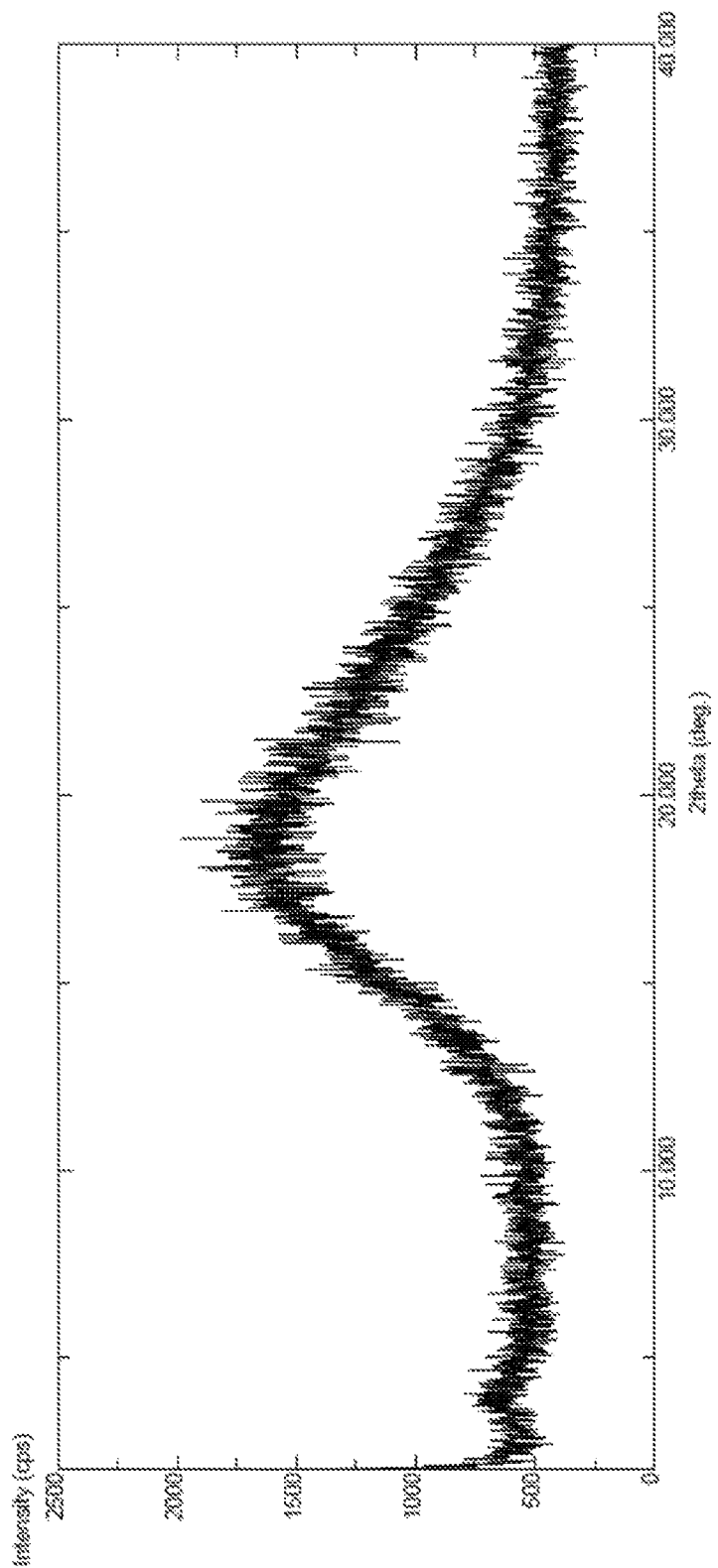
FIG. 2 is a powder X-ray diffraction (XRPD) pattern of amorphous form of (S) 2-Ethoxy-3-(4-{2-[2-methyl-5-(4-methylthiophenyl)-pyrrol-1-yl]-ethoxy}-phenyl)-propionic acid Sodium salt according to the present invention.
Figure 3:
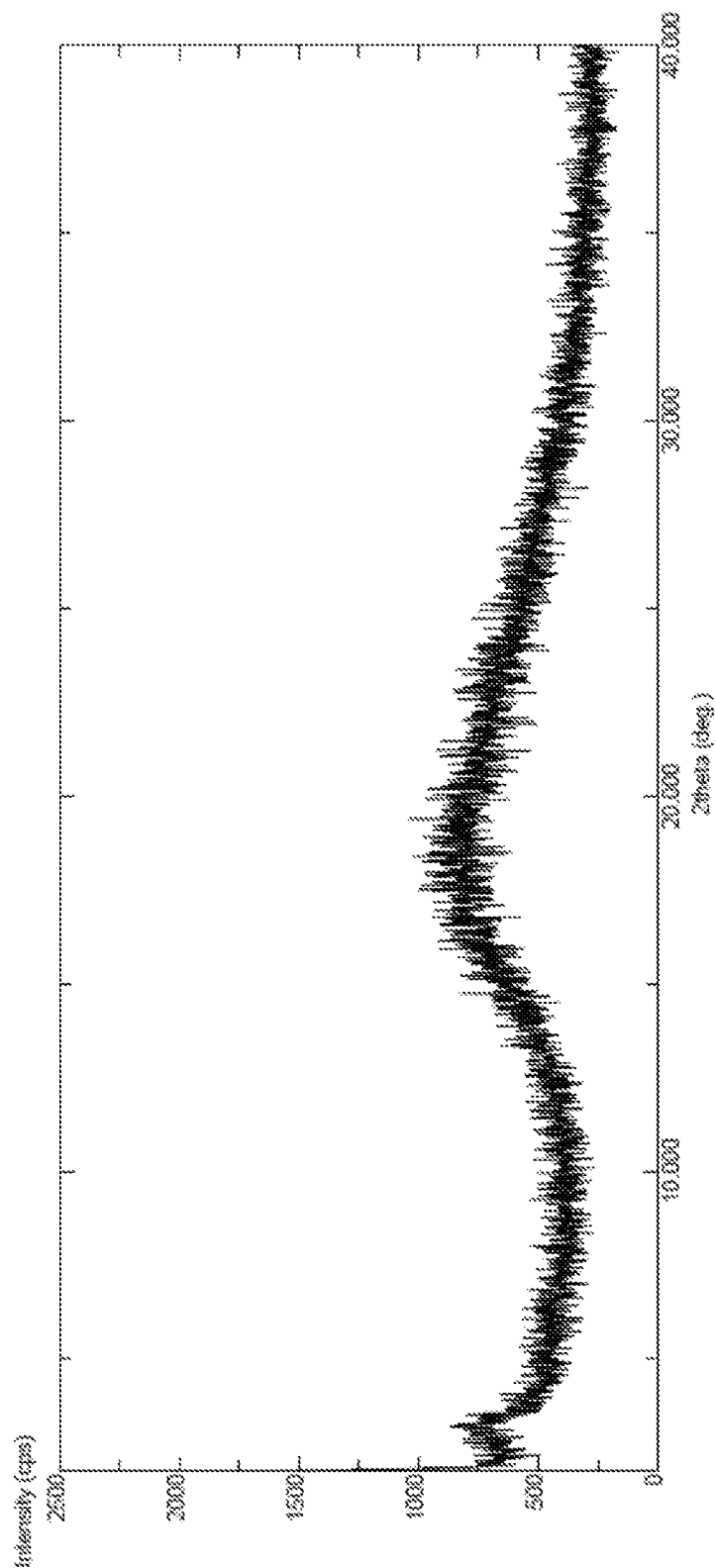
FIG. 3 is a powder X-ray diffraction (XRPD) pattern of amorphous form of (S) 2-Ethoxy-3-(4-{2-[2-methyl-5-(4-methylthiophenyl)-pyrrol-1-yl]-ethoxy}-phenyl)-propionic acid Potassium salt according to the present invention.
Figure 4:
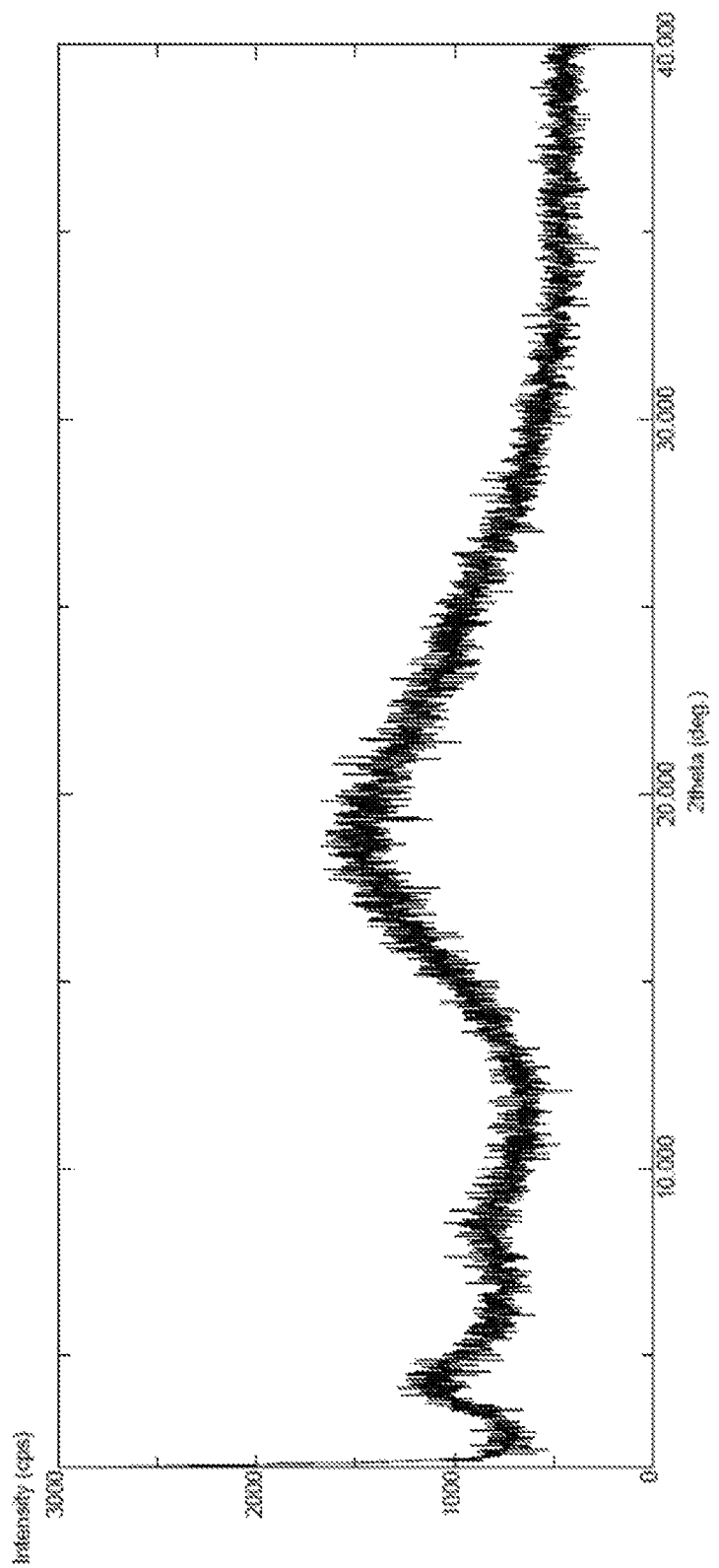
FIG. 4 is a powder X-ray diffraction (XRPD) pattern of amorphous form of (S) 2-Ethoxy-3-(4-{2-[2-methyl-5-(4-methylthiophenyl)-pyrrol-1-yl]-ethoxy}-phenyl)-propionic acid Zinc salt according to the present invention.
Figure 5:
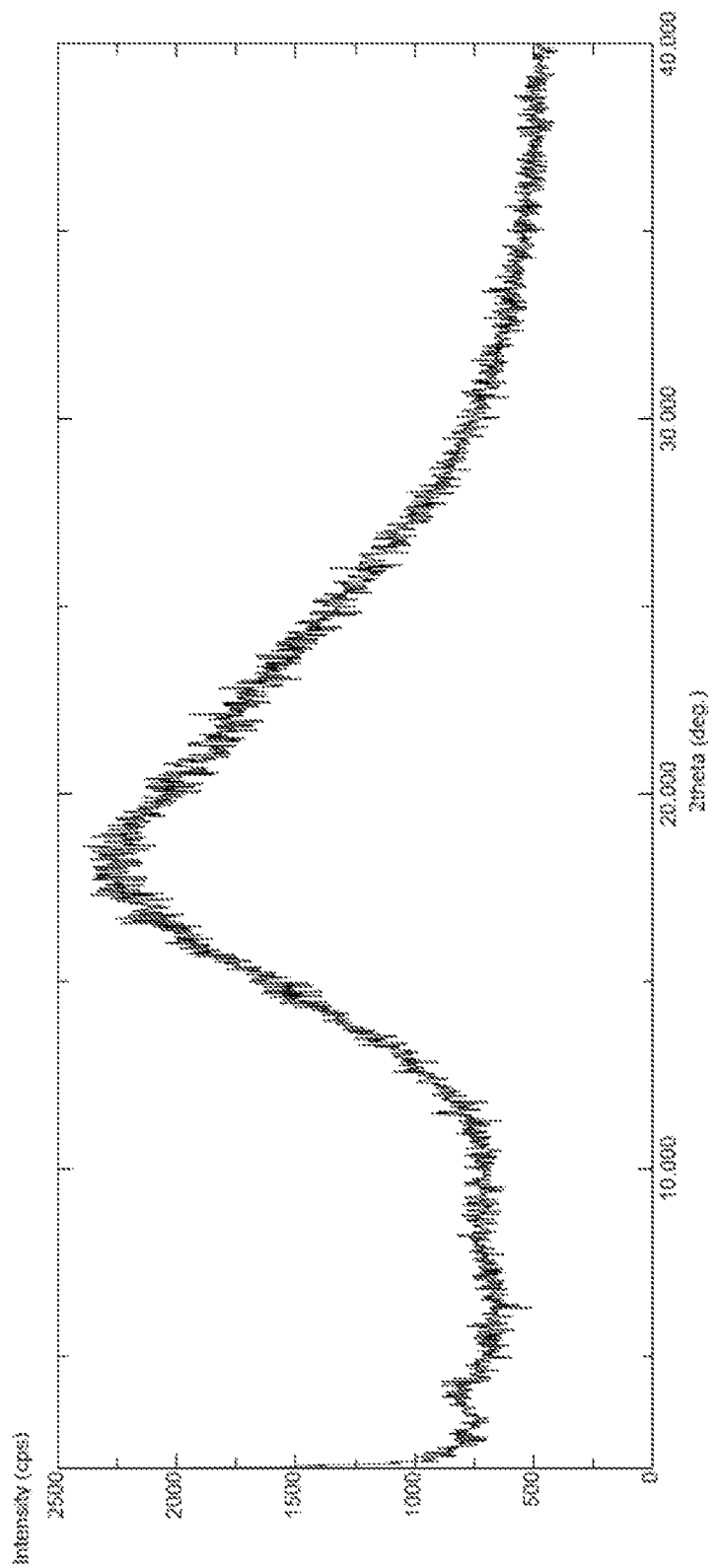
FIG. 5 is a powder X-ray diffraction (XRPD) pattern of amorphous form of (S) 2-Ethoxy-3-(4-{2-[2-methyl-5-(4-methylthiophenyl)-pyrrol-1-yl]-ethoxy}-phenyl)-propionic acid Lithium salt according to the present invention.
Figure 6:
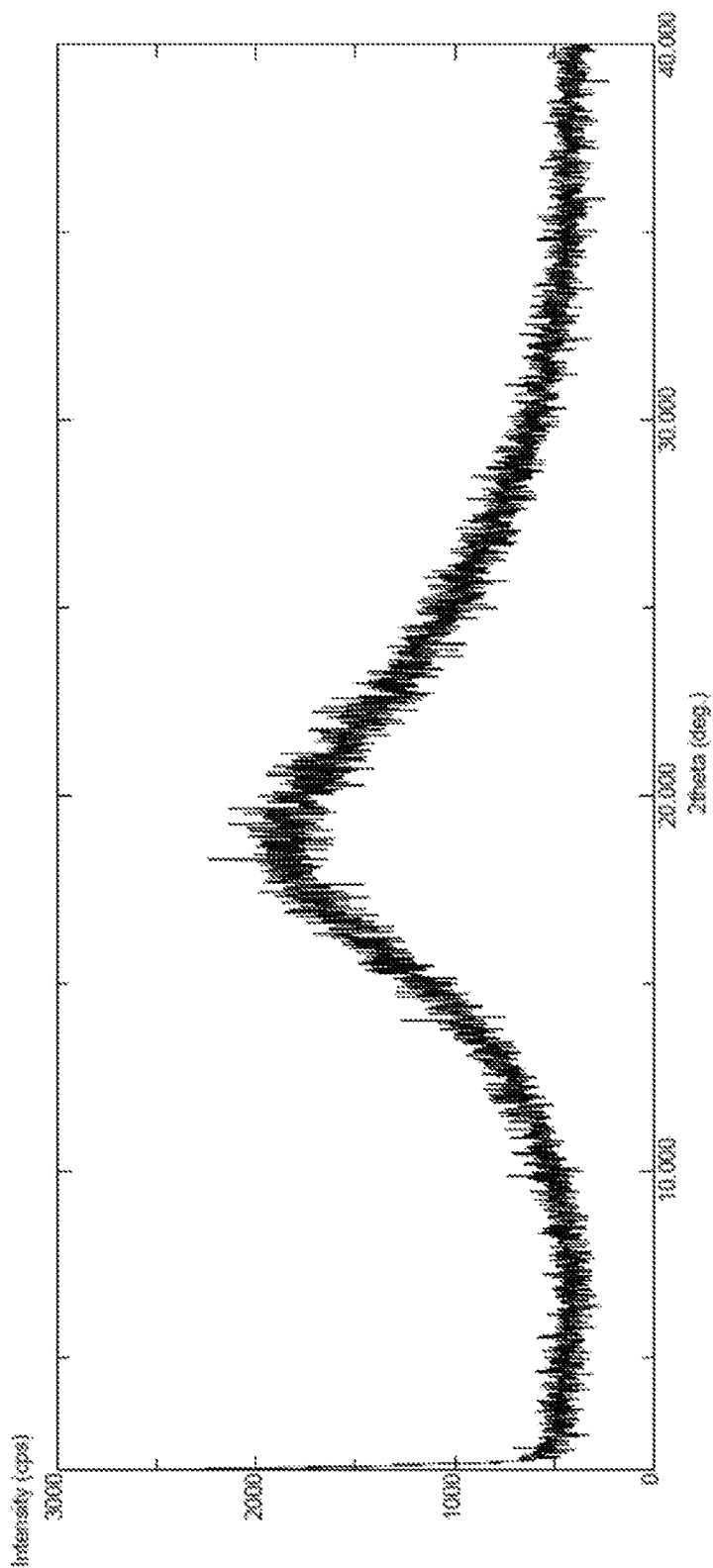
FIG. 6 is a powder X-ray diffraction (XRPD) pattern of amorphous form of (S) 2-Ethoxy-3-(4-{2-[2-methyl-5-(4-methylthiophenyl)-pyrrol-1-yl]-ethoxy}-phenyl)-propionic acid Piperazine salt according to the present invention.
Figure 7:
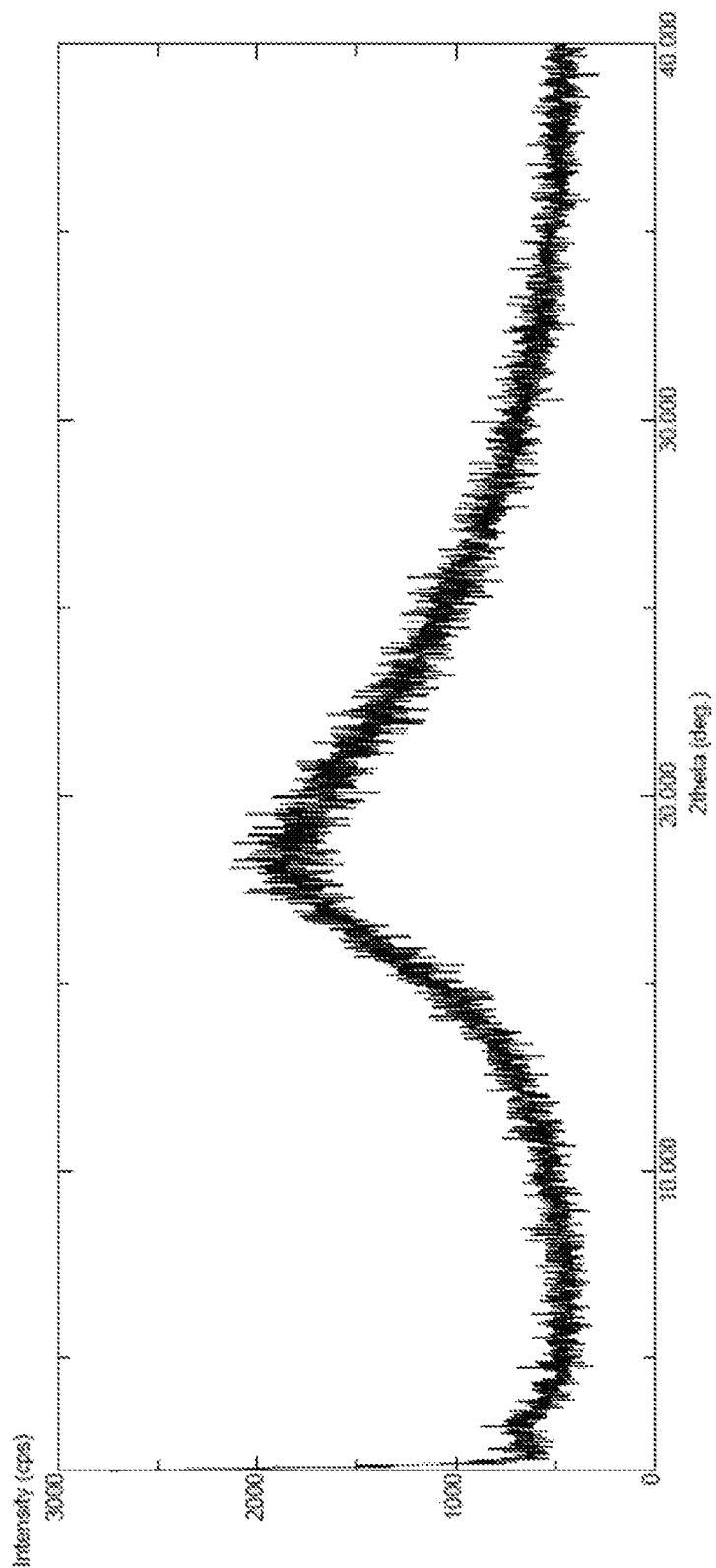
FIG. 7 is a powder X-ray diffraction (XRPD) pattern of amorphous form of (S) 2-Ethoxy-3-(4-{2-[2-methyl-5-(4-methylthiophenyl)-pyrrol-1-yl]-ethoxy}-phenyl)-propionic acid Tromethamine salt according to the present invention.
Figure 8:
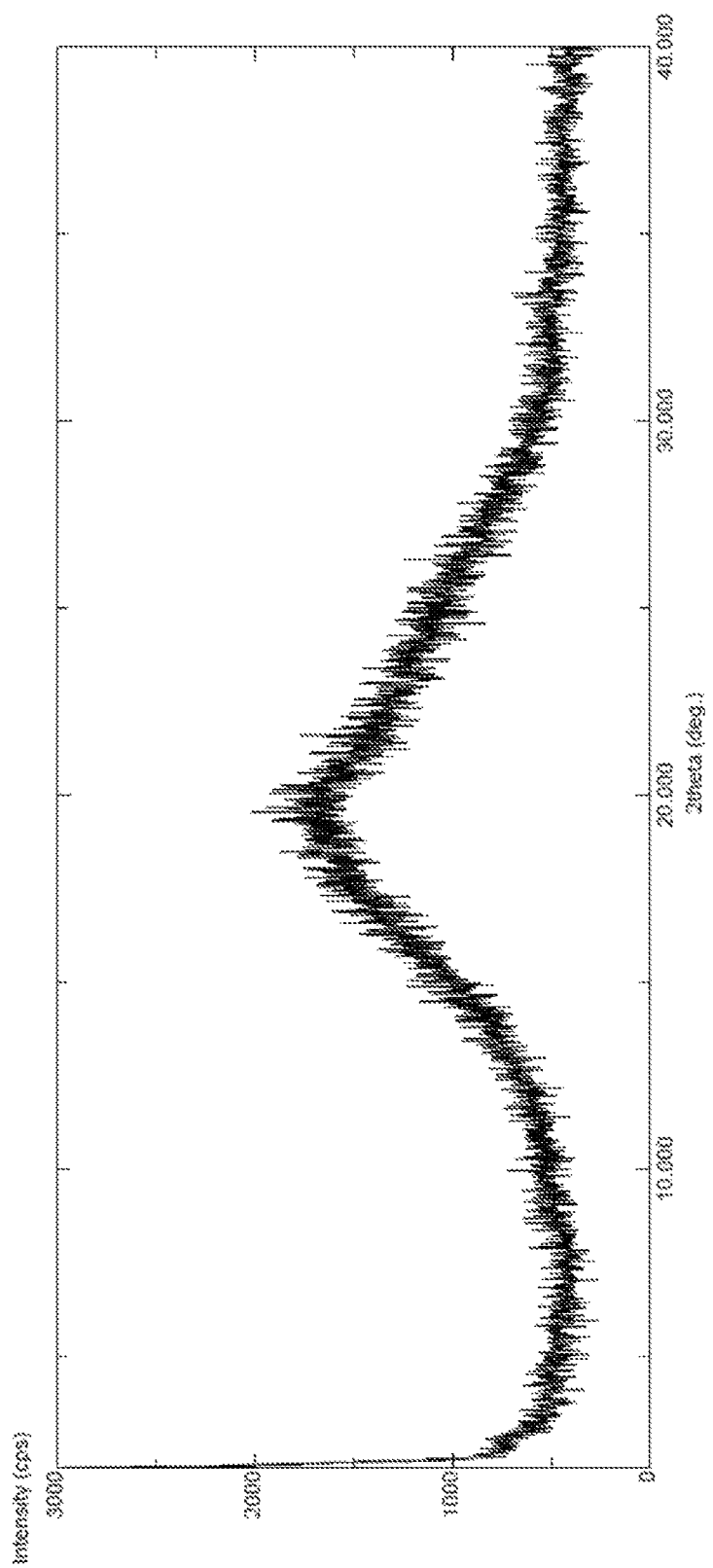
FIG. 8 is a powder X-ray diffraction (XRPD) pattern of amorphous form of (S) 2-Ethoxy-3-(4-{2-[2-methyl-5-(4-methylthiophenyl)-pyrrol-1-yl]-ethoxy}-phenyl)-propionic acid L-Lysine salt according to the present invention.
Figure 9:
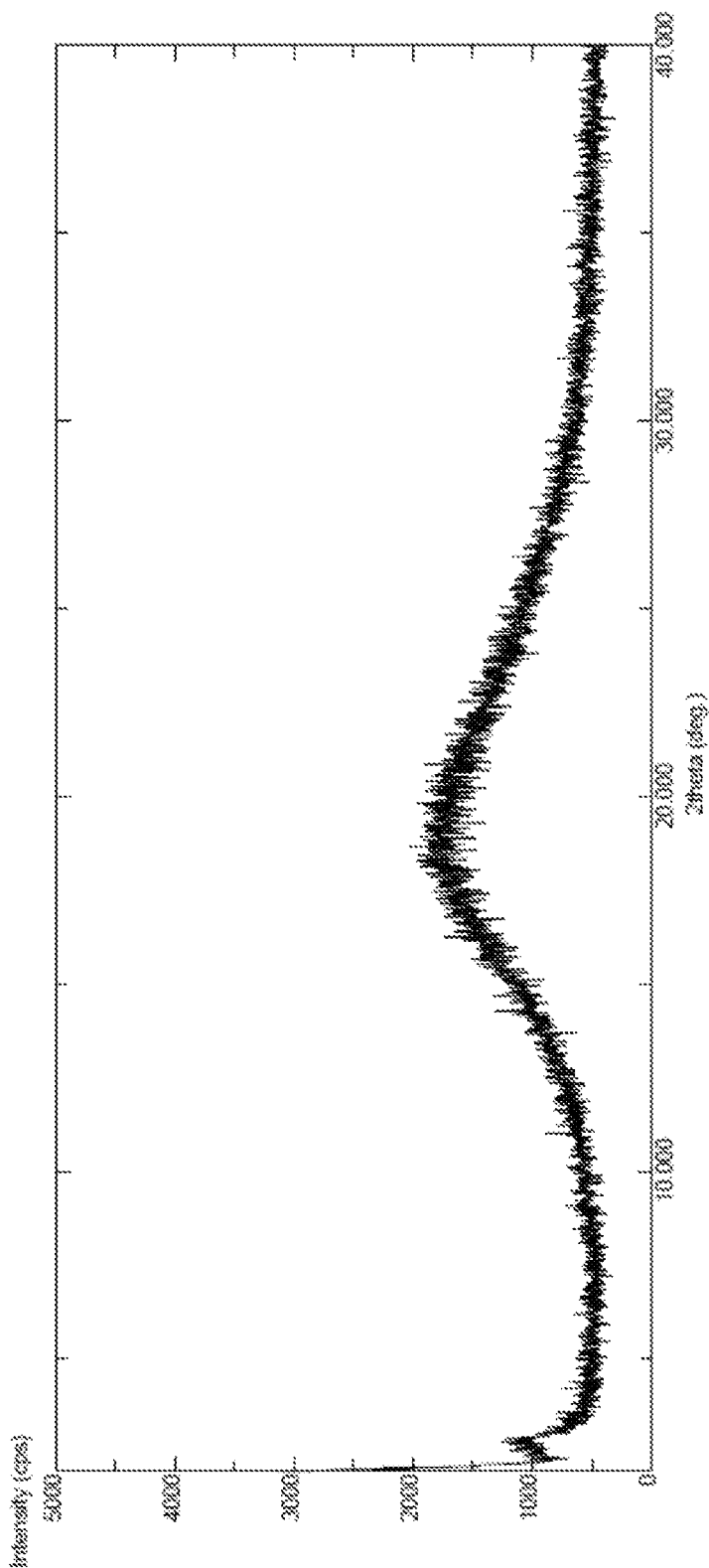
FIG. 9 is a powder X-ray diffraction (XRPD) pattern of amorphous form of (S) 2-Ethoxy-3-(4-{2-[2-methyl-5-(4-methylthiophenyl)-pyrrol-1-yl]-ethoxy}-phenyl)-propionic acid Meglumine salt according to the present invention.

As used herein, the term "DIPE" refers to Diisopropyl ether; as used herein the term "DMSO" refers to Dimethyl sulfoxide; as used herein, the term "MTBE" refers to Methyl-tert Butyl Ether; as used herein, the term "THF" refers to Tetrahydrofuran; as used herein, the term "DMF" refers to N,N-Dimethyl formamide; as used herein, the term "DMA" refers to N,N-Dimethylacetamide; as used herein, the term "MIBK" refers to Methyl Isobutyl Ketone; as used herein, the term "MEK" refers to Methyl ethyl ketone.

In one of the embodiments the present invention describes a synergistic composition comprising a compound of formula (Ia) and at least one more therapeutic agent selected from one or more DPP IV inhibitors or one or more biguanide antihyperglycaemic agents or one or more statins or one or more thiazolidinediones or one or more sulfonylureas or one or more SGLT2 inhibitors or one or more insulin sensitizers or one or more GLP-1 agonists for the treatment of diabetes, dyslipidemia and their associated disorders.

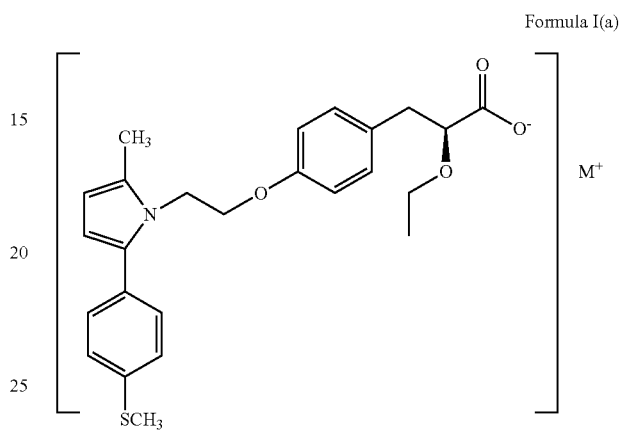

Formula I(a)

wherein 'M⁺' represents Calcium, Magnesium, Sodium, Potassium, Zinc and Lithium preferably Magnesium.

In another embodiment is provided compounds of Formula (I)

wherein 'R' is selected from hydroxy, hydroxyalkyl, acyl, alkoxy, alkylthio, thioalkyl, aryloxy, arylthio and M⁺ represents Calcium, Magnesium, Sodium, Potassium, Zinc, Lithium, L-Arginine, Tromethamine, L-Lysine, Meglumine, Benethamine, Piperazine, Benzylamine, Dibenzylamine, Dicyclohexylamine, Diethylamine, Diphenylamine, α-naphthylamine, O-phenylenediamine, 1,3-Diaminopropane, (S)-α-naphthylethylamine, (S)-3-methoxyphenylethylamine, (S)-4-methoxyphenylethylamine, (S)-4-chlorophenylethylamine, (S)-4-methylphenylethylamine, Cinchonine, Cinchonidine, (−)-Quinine, Benzathine, Ethanolamine, Diethanol amine, Triethanolamine, imidazole, Diethylamine, Ethylenediamine, Choline, Epolamine, Morpholine 4-(2-hydroxyethyl), N—N-diethylethanolamine, Deanol, Hydrabamine, Betaine, Ammonia, Adamantanamine, L-Adamantanmethylamine, Tritylamine, Glucamine N-methyl, Pyrrolidine and the like.

In a preferred embodiment, 'R' represents thioalkyl, alkoxy or hydroxyalkyl group; in a still preferred embodiment, 'R' represents —$SCH_3$ or —$OCH_3$ group.

In a more preferred embodiment, the present invention discloses a synergistic composition comprising at least a second therapeutic agent selected from one or more DPP IV inhibitors or one or more biguanide antihyperglycaemic agents or one or more statins or one or more thiazolidinediones or one or more sulfonylureas or one or more SGLT2 inhibitors and the compound of formula (Ia) wherein $M^+$ represents Magnesium having the name Saroglitazar Magnesium & the chemical name Benzenepropanoic acid, α-ethoxy-4-[2-[2-methyl-5-[4-(methylthio) phenyl]-1H -pyrrol-1-yl] ethoxy]-, magnesium salt.

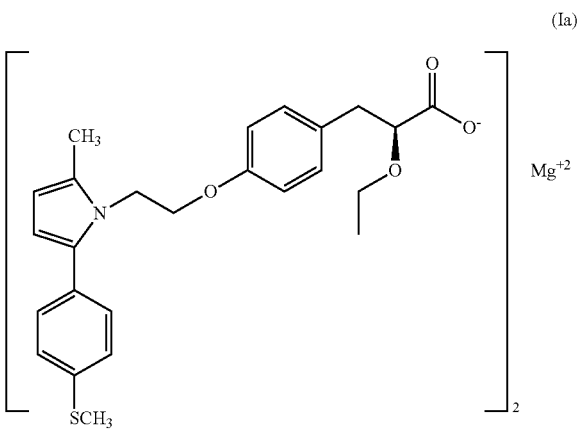

(Ia)

In an embodiment, the DPP IV inhibitors may be selected from Sitagliptin, Vildagliptin, Saxagliptin, Alogliptin and Linagliptin including their pharmaceutically acceptable salts, polymorphs, solvates and hydrates. Other DPP IV inhibitors which may be used include Carmegliptin, Melogliptin, Dutogliptin, Denagliptin, P93/01 (Prosidion), SYR322 (Takeda), GSK 823093, Roche 0730699, TS021 (Taisho), E3024 (Eisai), and PHX-1149 (Phenomix) and the like.

In a preferred embodiment, the DPP IV inhibitor is Sitagliptin.

In another preferred embodiment, the DPP IV inhibitor is Vildagliptin.

In another preferred embodiment, the DPP IV inhibitor is Saxagliptin.

In another preferred embodiment, the DPP IV inhibitor is Alogliptin.

In another preferred embodiment, the DPP IV inhibitor is Linagliptin.

In an embodiment, the statins may be selected from Lovastatin, Pravastatin, Fluvastatin, Simvastatin, Atorvastatin, Rosuvastatin and Pitavastatin.

In a preferred embodiment, the statin is Lovastatin also known by the innovator brand name Mevacor.

In another preferred embodiment, the statin is Pravastatin also known by the brand name Pravachol.

In another preferred embodiment, the statin is Simvastatin also known by the innovator brand name Zocor.

In another preferred embodiment, the statin is Atorvastatin also known by the innovator brand name Lipitor.

In yet another preferred embodiment, the statin is Rosuvastatin also known by the innovator brand name Crestor.

In yet another preferred embodiment, the statin is Fluvastatin also known by the innovator brand name Lescol.

In a still further embodiment, the statin is Pitavastatin also known by the innovator brand name Livalo.

In another embodiment, the suitable biguanide antihyperglycaemic agent is selected from Metformin, Buformin, and Phenformin.

In a preferred embodiment, the biguanide antihyperglycaemic agent is Metformin.

In another embodiment, the SGLT-2 inhibitors are selected from Canagliflozin, Dapagliflozinor Empagliflozin, Ertugliflozin & Ipragliflozin.

In another embodiment, the GLP-1 receptor agonist is selected from Exenatide or Liraglutide & Dulaglutide.

Accordingly, the invention provides a method for the treatment of dyslipidemia, hypertriglyceridemia and diabetes mellitus and conditions associated with these disorders in a mammal such as a human, which method comprises administering an effective, non-toxic and pharmaceutically acceptable amount of a compound of formula (I) and at least one second therapeutic agent selected from one or more DPP IV inhibitors, or a statin or a suitable biguanide antihyperglycaemic agent, to a mammal in need thereof.

The method comprises either co-administration of a compound of formula (I) and one or more DPP IV inhibitors, or a statin or a suitable biguanide antihyperglycaemic agent or other therapeutic agent as described in the specification, or the sequential administration thereof.

Co-administration includes administration of a formulation which includes both a compound of formula (I) and one or more DPP IV inhibitors or a statin or a suitable biguanide antihyperglycaemic agent, or one or more thiazolidinediones or one or more sulfonylureas or one or more SGLT2 inhibitors or one or more insulin sensitizers or the essentially simultaneous administration of separate formulations of each agent.

In another aspect the invention provides the use of a compound of formula (I) and a second therapeutic agent selected from one or more DPP IV inhibitors, or a statin or a suitable biguanide antihyperglycaemic agent, or one or more SGLT2 inhibitors, or one or more GLP-1-receptor agonist along with another suitable therapeutic agent for use in the manufacture of a composition for the treatment of obesity, diabetes mellitus, especially Type 2 diabetes and conditions associated with diabetes mellitus.

Suitably, the other therapeutic agent comprises one or more, generally one or two, of an antidiabetic agent, an alpha glucosidase inhibitor, a biguanide, an insulin secretagogue or an insulin sensitiser or sulphonylureas, DPP IV inhibitor.

A further suitable antidiabetic agent is insulin.

A suitable alpha glucosidase inhibitor is acarbose.

Other suitable alpha glucosidase inhibitors are emiglitate and miglitol. A further suitable alpha glucosidase inhibitor is voglibose.

Suitable DPP IV inhibitors which can be used include Sitagliptin, Vildagliptin, Saxagliptin, Alogliptin, Carmegliptin, Melogliptin, Dutogliptin, Denagliptin, Linagliptin, P93/01 (Prosidion), SYR322 (Takeda), GSK 823093, Roche 0730699, TS021 (Taisho), E3024 (Eisai), and PHX-1149 (Phenomix) and the like.

Suitable biguanides include metformin, buformin or phenformin, especially metformin.

Suitable insulin secretagogues include sulphonylureas.

Suitable sulphonylureas include glibenclamide, glipizide, gliclazide, glimepiride, tolazamide and tolbutamide. Further sulphonylureas include acetohexamide, carbutamide, chlorpropamide, glibomuride, gliquidone, glisentide, glisolamide, glisoxepide, glyclopyamide and glycylamide. Also included is the sulphonylurea glipentide.

A further suitable insulin secretagogue is repaglinide. An additional insulin secretagogue is nateglinide.

Insulin sensitisers also include thiazolidinedione insulin sensitisers.

Suitable thiazolidinedione insulin sensitisers include (RS)-5-[4-(2-[methyl (pyridin-2-yl)amino]ethoxy)benzyl] thiazolidine-2,4-dione (or Rosiglitazone), (+)-5-[[4-[(3,4-dihydro-6-hydroxy-2,5,7,8-tetramethyl-2H-1-benzopyran-2-yl) methoxy]phenyl]methyl]-2,4-thiazolidinedione (or troglitazone), 5-[4-[(1-methylcyclohexyl)methoxy]benzyl] thiazolidine-2,4-dione (or ciglitazone), 5-[4-[2-(5-ethylpyridin-2-yl)ethoxy]benzyl] thiazolidine-2,4-dione (or pioglitazone) or 5-[(2-benzyl-2,3-dihydrobenzopyran)-5-ylmethyl] thiazolidin-2,4-dione (or englitazone)

The present invention is based on the surprising finding that either a DPP IV inhibitor or a statin or a biguanide antihyperglycaemic agent or a sulphonylurea or an SGLT-2 inhibitor increases the activity of the PPAR agonists of formula (I) and can be used to treat or prevent dyslipidemia and type 2 diabetes and other disorders responsive to PPAR activators or PPAR activation, without increasing the risk for side effects such as rhabdomylosis, fluid retention, edema, or congestive heart failure.

It will be understood that compound of formula (I) and one or more DPP IV inhibitors or a statin or a suitable biguanide antihyperglycaemic agent are each administered in a pharmaceutically acceptable form, including pharmaceutically acceptable derivatives such as pharmaceutically acceptable salts, esters and solvates thereof, as appropriate of the relevant pharmaceutically active agent. In certain instances herein the names used for the DPP IV inhibitors or the biguanide antihyperglycaemic agent or statins etc. may relate to a particular pharmaceutical form of the relevant active agent. It will be understood that all pharmaceutically acceptable forms of the active agents per se are encompassed by this invention. Suitable pharmaceutically acceptable forms of the DPP IV inhibitor or the biguanide antihyperglycaemic agent or statins etc. depend upon the particular agent being used but include known pharmaceutically acceptable forms of the particular agent chosen. Such derivatives are found or are referred to in standard reference texts such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) and the likes.

The compounds of formula (I) can be prepared by the general processes and examples disclosed in WO 03009841. The DPP IV inhibitors or the biguanide antihyperglycaemic agent or statins and other therapeutic agents used in the invention may be prepared by processes known in the art including those publications referred to earlier in the specification.

Certain of the compounds mentioned herein may contain one or more chiral carbon atoms and hence can exist in two or more isomeric forms, all of which are encompassed by the invention, either as individual isomers or as mixtures of isomers, including racemates. If any of the compounds mentioned herein, in particular the compounds of (I), exist in one of several tautomeric forms, all of them are encompassed by the invention as individual tautomeric forms or as mixtures thereof.

When used herein the term 'dyslipidemia' include conditions associated with hypertriglyceridemia and/or hypercholesterolemia and/or high LDL-C and/or low HDL-C and complications associated with them.

'Conditions associated with dyslipidemia' include atherosclerosis, hypertension and other disorders known to a person skilled in the art.

When used herein the term 'conditions associated with diabetes' includes those conditions associated with diabetes mellitus itself and complications associated with diabetes mellitus.

'Conditions associated with diabetes mellitus itself' include hyperglycaemia, insulin resistance, including acquired insulin resistance and obesity. Further conditions associated with diabetes mellitus itself include hypertension and cardiovascular disease, especially atherosclerosis and conditions associated with insulin resistance. Conditions associated with insulin resistance include polycystic ovarian syndrome and steroid induced insulin resistance and gestational diabetes.

'Complications associated with dyslipidemia and diabetes mellitus' includes renal disease, neuropathy and retinopathy.

'Renal diseases' include nephropathy, glomerulonephritis, glomerular sclerosis, nephrotic syndrome, hypertensive nephrosclerosis and end stage renal disease.

Diabetes mellitus is preferably Type 2 diabetes.

It is also considered that the treatment of the invention will effect an improvement, relative to the individual agents, of one or more parameters which are therapeutically relevant including in the levels of advanced glycosylation end products (AGEs), and serum lipids including total cholesterol, HDL-cholesterol, LDL-cholesterol including improvements in the ratios thereof in particular an improvement in serum lipids including total cholesterol, HDL-cholesterol, LDL-cholesterol including improvements in the ratios thereof.

In the treatment of the invention, the active medicaments are preferably administered in pharmaceutical composition form. As indicated above, such compositions can include both medicaments and one only one of the medicaments in combination with the compound of formula (I).

Accordingly, in one aspect the present invention also provides a pharmaceutical composition comprising a compound of formula (I) and at least a second therapeutic agent selected from one or more DPP IV inhibitors or one or more biguanide antihyperglycaemic agent or one or more statins or one or more thiazolidinediones or one or more sulfonylureas or one or more SGLT2 inhibitors or one or more insulin sensitizers and pharmaceutically acceptable excipients.

Thus, in a further aspect, the invention also provides a process for preparing a pharmaceutical composition comprising a compound of formula (I) and at least a second therapeutic agent selected from one or more DPP IV inhibitors or one or more biguanide antihyperglycaemic agents or one or more statins or other therapeutic agents as described elsewhere in the specification and pharmaceutically acceptable excipients, which process comprises admixing the compound of formula (I) and a second or optionally a third therapeutically active agent as described in the specification with suitable pharmaceutically acceptable excipients.

The compositions are preferably in a unit dosage form in an amount appropriate for the relevant daily dosage.

As used herein the term 'pharmaceutically acceptable' use embraces both human and veterinary use.

In the treatment the medicaments may be administered from 1 to 6 times a day, but most preferably 1 or 2 times per day.

Also, the dosages of each particular active agent in any given composition can as required vary within a range of doses known to be required in respect of accepted dosage regimens for that compound. Dosages of each active agent can also be adapted as required to take into account advantageous effects of combining the agents as mentioned herein.

It will be understood that the compound of formula (I) and the DPP IV inhibitors, biguanide antihyperglycaemic agents an SGLT-2 inhibitor or a sulphonylurea and statins are in a pharmaceutically acceptable form, including pharmaceutically acceptable derivatives such as pharmaceutically acceptable salts, esters and solvates thereof, as appropriate to the relevant pharmaceutically active agent chosen.

The present invention also provides a pharmaceutical composition comprising a compound of formula (I) and one or more DPP IV inhibitors or biguanide antihyperglycaemic agent or statins or one or more thiazolidinediones or one or more sulfonylureas or one or more SGLT2 inhibitors or one or more insulin sensitizers and pharmaceutically acceptable excipients, for use as an active therapeutic substance.

In particular, the present invention provides a pharmaceutical composition comprising a compound of formula (I) and at least a second therapeutic agent selected from one or more DPP IV inhibitors or biguanide antihyperglycaemic agents or statins or one or more thiazolidinediones or one or more sulfonylureas or one or more SGLT2 inhibitors or one or more insulin sensitizers and pharmaceutically acceptable excipients, for use in the treatment of dyslipidemia and diabetes mellitus, especially Type 2 diabetes and conditions associated with them.

Usually the compositions are adapted for oral administration. However, they may be adapted for other modes of administration, for example parenteral administration, sublingual or transdermal administration.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dosage presentation forms for oral administration may be in tablet or capsule form and may as necessary contain conventional excipients such as binding agents, fillers, lubricants, glidants, disintegrants and wetting agents.

The solid oral compositions may be prepared by conventional methods of blending, filling or tableting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, a preservative and buffering agent can be dissolved in the vehicle. To enhance the stability, the composition can be frozen after filling into the vial and the water removed under vacuum. Parenteral suspensions are prepared in substantially the same manner, except that the active compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Compositions may contain from 0.1% to 99% by weight, preferably from 10-60% by weight, of the active material, depending upon the method of administration. Examples of binding agents include acacia, alginic acid, carboxymethylcellulose calcium, carboxymethylcellulose sodium, dextrates, dextrin, dextrose, ethylcellulose, gelatin, liquid glucose, guar gum, hydroxyethyl cellulose, hydroxypropyl cellulose, hydroxypropyl methylcellulose, magnesium aluminium silicate, maltodextrin, methyl cellulose, polymethacrylates, polyvinylpyrrolidone, pregelatinised starch, sodium alginate, sorbitol, starch, syrup, tragacanth.

Examples of fillers include calcium carbonate, calcium phosphate, calcium sulphate, carboxymethylcellulose calcium, carboxymethylcellulose sodium, compressible sugar, confectioner's sugar, dextrates, dextrin, dextrose, dibasic calcium phosphate dihydrate, dibasic calcium phosphate, fructose, glyceryl palmitostearate, glycine, hydrogenated vegetable oil-type 1, kaolin, lactose, maize starch, magnesium carbonate, magnesium oxide, maltodextrin, mannitol, microcrystalline cellulose, polymethacrylates, potassium chloride, powdered cellulose, pregelatinised starch, sodium chloride, sorbitol, starch, sucrose, sugar spheres, talc, tribasic calcium phosphate, xylitol.

Examples of lubricants include calcium stearate, glyceryl monostearate, glyceryl palmitostearate, magnesium stearate, microcrystalline cellulose, sodium benzoate, sodium chloride, sodium lauryl sulphate, stearic acid, sodium stearyl fumarate, talc, zinc stearate.

Examples of glidants include colloidal silicon dioxide, powdered cellulose, magnesium trisilicate, silicon dioxide, talc.

Examples of disintegrants include alginic acid, carboxymethylcellulose calcium, carboxymethylcellulose sodium, colloidal silicon dioxide, croscarmellose sodium, crospovidone, guar gum, magnesium aluminium silicate, microcrystalline cellulose, methyl cellulose, polyvinylpyrrolidone, polacrilin potassium, pregelatinised starch, sodium alginate, sodium lauryl sulphate, sodium starch glycollate.

An example of a pharmaceutically acceptable wetting agent is sodium lauryl sulphate.

The compositions are prepared and formulated according to conventional methods, such as those disclosed in standard reference texts and are well within the scope of a skilled person. For example, the solid oral compositions may be prepared by conventional methods of blending, filling or tableting. Repeated blending operations may be used to distribute the active agent throughout those compositions employing large quantities of fillers. Such operations are of course conventional in the art. The tablets may be coated according to methods well known in normal pharmaceutical practice.

Compositions may, if desired, be in the form of a pack accompanied by written or printed instructions for use.

No adverse toxicological effects were seen for the compositions or methods of the invention in the above mentioned dosage ranges. Further the composition of the present invention was found suitable for the treatment of diabetes and its associated disorders without increasing the risk for fluid retention, peripheral edema, pulmonary edema, or congestive heart failure.

In one of the embodiment the present invention provides certain new salts of compound of Formula (I)

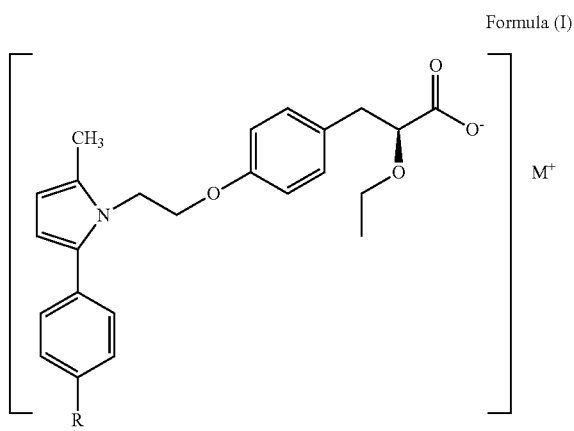

Formula (I)

wherein 'R' is selected from hydroxy, hydroxyalkyl, acyl, alkoxy, alkylthio, thioalkyl, aryloxy, arylthio and $M^+$ represents Calcium, Sodium, Potassium, Zinc, Lithium, L-Arginine, Tromethamine, L-Lysine, Meglumine, Benethamine, Piperazine, Benzylamine, Dibenzylamine, Dicyclohexylamine, Diethylamine, Diphenylamine, α-naphthylamine, O-phenylenediamine, 1,3-Diaminopropane, (S)-α-naphthylethylamine, (S)-3-methoxyphenylethylamine, (S)-4-methoxyphenylethylamine, (S)-4-chlorophenylethylamine, (S)-4-methylphenylethylamine, Cinchonine, Cinchonidine, (−)-Quinine, Benzathine, Ethanolamine, Diethanol amine, Triethanolamine, imidazole, Diethylamine, Ethylenediamine, Choline, Epolamine, Morpholine 4-(2-hydroxyethyl), N—N-diethylethanolamine, Deanol, Hydrabamine, Betaine, Ammonia, Adamantanamine, L-Adamantanmethylamine, Tritylamine, Glucamine N-methyl, Pyrrolidine.

In a preferred embodiment, 'R' represents thioalkyl and alkoxy or hydroxyalkyl group; In a still preferred embodiment, 'R' represents —SCH₃ or —OCH₃ group. In an embodiment these salts may be present either in crystalline or amorphous form or suitable mixtures of crystalline and amorphous forms. In a further embodiment, each of the crystalline and/or amorphous forms may independently exist either in hydrated, solvated, non-solvated, anhydrous, solvent free or desolvated solvates of either the crystalline, amorphous or various mixtures of crystalline and amorphous forms.

In one embodiment the some of the novel salts of the present invention can be used for the purification of free acid of formula (I) by reacting the impure acid with suitable salt in a suitable solvent and then the pure acid is obtained from the salt by suitable techniques. The pure free acid of formula (I) can be further converted to Magnesium & other therapeutic salts of compound of formula (I)

In one embodiment of the invention is provided the (S) 2-Ethoxy-3-(4-{2-[2-methyl-5-(4-methylthiophenyl)-pyrrol-1-yl]-ethoxy}-phenyl)-propionic acid calcium salt. In an embodiment, (S) 2-Ethoxy-3-(4-{2-[2-methyl-5-(4-methylthiophenyl)-pyrrol-1-yl]-ethoxy}-phenyl)-propionic acid calcium salt can be present in either crystalline and/or amorphous form each of which can optionally be present in anhydrous, solvent free, hydrated or solvated forms.

In a preferred embodiment, the calcium salt is present in crystalline form.

In another preferred embodiment, the calcium salt is present in amorphous form.

In an embodiment is provided (S) 2-Ethoxy-3-(4-{2-[2-methyl-5-(4-methylthiophenyl)-pyrrol-1-yl]-ethoxy}-phenyl)-propionic acid sodium salt. In an embodiment, (S) 2-Ethoxy-3-(4-{2-[2-methyl-5-(4-methylthiophenyl)-pyrrol-1-yl]-ethoxy}-phenyl)-propionic acid sodium salt can be present in either crystalline and/or amorphous form each of which can optionally be present in anhydrous, hydrated or solvated forms.

In a preferred embodiment, the sodium salt is present in crystalline form.

In another preferred embodiment, the sodium salt is present in amorphous form.

In an embodiment is provided (S) 2-Ethoxy-3-(4-{2-[2-methyl-5-(4-methylthiophenyl)-pyrrol-1-yl]-ethoxy}-phenyl)-propionic acid potassium salt. In an embodiment, (S) 2-Ethoxy-3-(4-{2-[2-methyl-5-(4-methylthiophenyl)-pyrrol-1-yl]-ethoxy}-phenyl)-propionic acid potassium salt can be present in either crystalline and/or amorphous form each of which can optionally be present in anhydrous, hydrated or solvated forms.

In a preferred embodiment, the potassium salt is present in crystalline form.

In another preferred embodiment, the potassium salt is present in amorphous form.

In an embodiment is provided (S) 2-Ethoxy-3-(4-{2-[2-methyl-5-(4-methylthiophenyl)-pyrrol-1-yl]-ethoxy}-phenyl)-propionic acid zinc salt. In an embodiment, (S) 2-Ethoxy-3-(4-{2-[2-methyl-5-(4-methylthiophenyl)-pyrrol-1-yl]-ethoxy}-phenyl)-propionic acid zinc salt can be present in either crystalline and/or amorphous form each of which can optionally be present in anhydrous, hydrated or solvated forms.

In a preferred embodiment, the zinc salt is present in crystalline form.

In another preferred embodiment, the zinc salt is present in amorphous form.

In an embodiment is provided (S) 2-Ethoxy-3-(4-{2-[2-methyl-5-(4-methylthiophenyl)-pyrrol-1-yl]-ethoxy}-phenyl)-propionic acid lithium salt. In an embodiment, (S) 2-Ethoxy-3-(4-{2-[2-methyl-5-(4-methylthiophenyl)-pyrrol-1-yl]-ethoxy}-phenyl)-propionic acid lithium salt can be present in either crystalline and/or amorphous form each of which can optionally be present in anhydrous, hydrated or solvated forms.

In one embodiment is provided (S) 2-Ethoxy-3-(4-{2-[2-methyl-5-(4-methylthiophenyl)-pyrrol-1-yl]-ethoxy}-phenyl)-propionic acid L-arginine salt. In an embodiment, (S) 2-Ethoxy-3-(4-{2-[2-methyl-5-(4-methylthiophenyl)-pyrrol-1-yl]-ethoxy}-phenyl)-propionic acid L-arginine salt can be present in either crystalline and/or amorphous form each of which can optionally be present in anhydrous, hydrated or solvated forms.

In an embodiment is provided (S) 2-Ethoxy-3-(4-{2-[2-methyl-5-(4-methylthiophenyl)-pyrrol-1-yl]-ethoxy}-phenyl)-propionic acid Tromethamine salt. In an embodiment, (S) 2-Ethoxy-3-(4-{2-[2-methyl-5-(4-methylthiophenyl)-pyrrol-1-yl]-ethoxy}-phenyl)-propionic acid Tromethamine salt can be present in either crystalline and/or amorphous form each of which can optionally be present in anhydrous, hydrated or solvated forms.

In an embodiment is provided (S) 2-Ethoxy-3-(4-{2-[2-methyl-5-(4-methylthiophenyl)-pyrrol-1-yl]-ethoxy}-phenyl)-propionic acid L-Lysine salt. In an embodiment, (S) 2-Ethoxy-3-(4-{2-[2-methyl-5-(4-methylthiophenyl)-pyrrol-1-yl]-ethoxy}-phenyl)-propionic acid L-Lysine salt can be present in either crystalline and/or amorphous form each of which can optionally be present in anhydrous, hydrated or solvated forms.

In an embodiment is provided (S) 2-Ethoxy-3-(4-{2-[2-methyl-5-(4-methylthiophenyl)-pyrrol-1-yl]-ethoxy}-phenyl)-propionic acid Meglumine salt.

In an embodiment, (S) 2-Ethoxy-3-(4-{2-[2-methyl-5-(4-methylthiophenyl)-pyrrol-1-yl]-ethoxy}-phenyl)-propionic acid Meglumine salt can be present in either crystalline and/or amorphous form each of which can optionally be present in anhydrous, hydrated or solvated forms.

In an embodiment is provided (S) 2-Ethoxy-3-(4-{2-[2-methyl-5-(4-methylthiophenyl)-pyrrol-1-yl]-ethoxy}-phenyl)-propionic acid Benethamine salt.

In a further embodiment, (S) 2-Ethoxy-3-(4-{2-[2-methyl-5-(4-methylthiophenyl)-pyrrol-1-yl]-ethoxy}-phenyl)-propionic acid Benethamine salt can be present in either crystalline and/or amorphous form each of which can optionally be present in anhydrous, hydrated or solvated forms.

In a preferred embodiment is provided a crystalline form of (S) 2-Ethoxy-3-(4-{2-[2-methyl-5-(4-methylthiophenyl)-pyrrol-1-yl]-ethoxy}-phenyl)-propionic acid Benethamine salt according to the present invention characterized by its powder X-ray diffraction pattern having peaks expressed as 2θ±0.2 degree at about 10.0, 10.3, 14.5, 15.1, 15.7, 16.7, 17.4, 17.9, 18.6, 19.2, 19.8, 21.3, 23.2 and 25.7.

Figure 10:
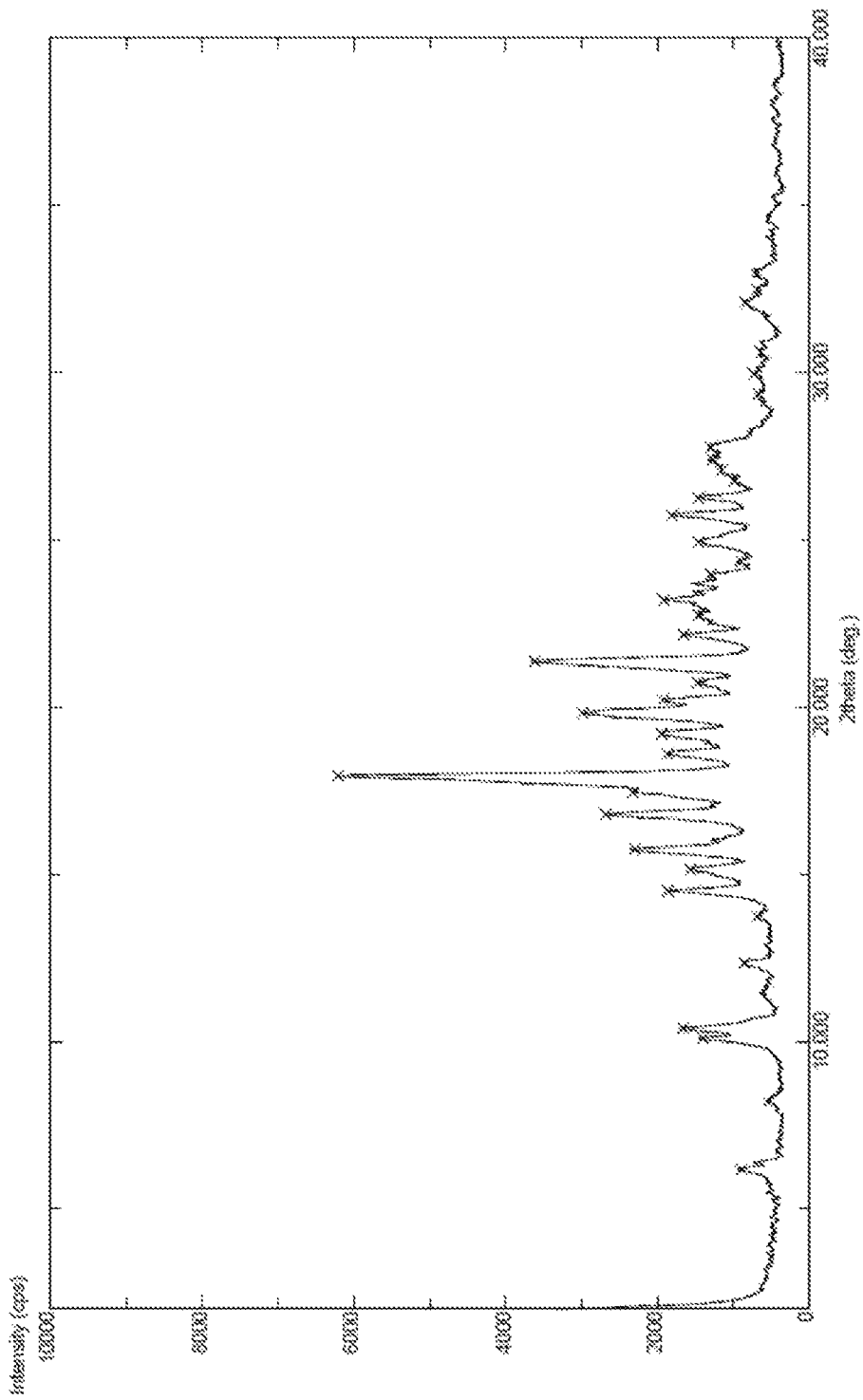
FIG. 10 is a powder X-ray diffraction (XRPD) pattern of crystalline form of (S) 2-Ethoxy-3-(4-{2-[2-methyl-5-(4-methylthiophenyl)-pyrrol-1-yl]-ethoxy}-phenyl)-propionic acid Benethamine salt according to the present invention.

In a still further preferred embodiment the crystalline form of (S) 2-Ethoxy-3-(4-{2-[2-methyl-5-(4-methylthiophenyl)-pyrrol-1-yl]-ethoxy}-phenyl)-propionic acid Benethamine salt is further characterized by its powder X-ray diffraction pattern (PXRD) as depicted in FIG. 10.

In an embodiment is provided (S) 2-Ethoxy-3-(4-{2-[2-methyl-5-(4-methylthiophenyl)-pyrrol-1-yl]-ethoxy}-phenyl)-propionic acid piperazine salt. In an embodiment, (S) 2-Ethoxy-3-(4-{2-[2-methyl-5-(4-methylthiophenyl)-pyrrol-1-yl]-ethoxy}-phenyl)-propionic acid piperazine salt can be present in either crystalline and/or amorphous form each of which can optionally be present in anhydrous, hydrated or solvated forms.

In an embodiment is provided (S) 2-Ethoxy-3-(4-{2-[2-methyl-5-(4-methylthio phenyl)-pyrrol-1-yl]-ethoxy}-phenyl)-propionic acid benzylamine salt. In a further embodiment, (S) 2-Ethoxy-3-(4-{2-[2-methyl-5-(4-methylthiophenyl)-pyrrol-1-yl]-ethoxy}-phenyl)-propionic acid benzylamine salt can be present in either crystalline and/or amorphous form each of which can optionally be present in anhydrous, hydrated or solvated forms.

In a preferred embodiment is provided a crystalline form of (S) 2-Ethoxy-3-(4-{2-[2-methyl-5-(4-methylthiophenyl)-pyrrol-1-yl]-ethoxy}-phenyl)-propionic acid benzylamine salt according to the present invention characterized by its powder X-ray diffraction pattern having peaks expressed as 2θ±0.2 degree at about 14.8, 16.8, 17.5, 18.3, 19.3, 20.8, 22.6 and 24.2.

Figure 11:
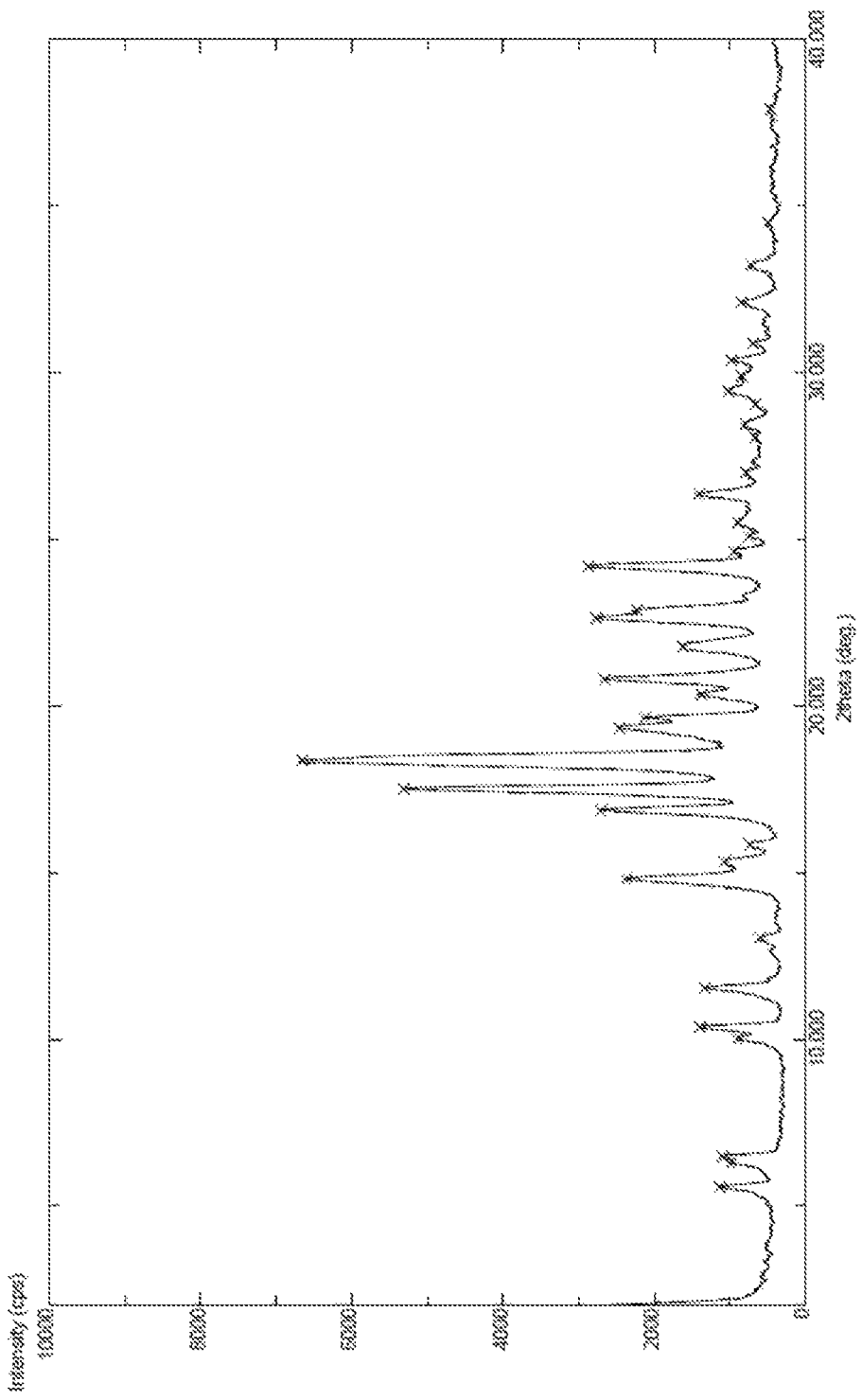
FIG. 11 is a powder X-ray diffraction (XRPD) pattern of crystalline form of (S) 2-Ethoxy-3-(4-{2-[2-methyl-5-(4-methylthiophenyl)-pyrrol-1-yl]-ethoxy}-phenyl)-propionic acid Benzylamine salt according to the present invention.

In a still further preferred embodiment the crystalline form of (S) 2-Ethoxy-3-(4-{2-[2-methyl-5-(4-methylthiophenyl)-pyrrol-1-yl]-ethoxy}-phenyl)-propionic acid benzylamine salt is further characterized by its powder X-ray diffraction pattern (PXRD) as depicted in FIG. 11.

In an embodiment is provided (S) 2-Ethoxy-3-(4-{2-[2-methyl-5-(4-methylthiophenyl)-pyrrol-1-yl]-ethoxy}-phenyl)-propionic acid Dibenzylamine salt. In a further embodiment, (S) 2-Ethoxy-3-(4-{2-[2-methyl-5-(4-methylthiophenyl)-pyrrol-1-yl]-ethoxy}-phenyl)-propionic acid Dibenzylamine salt can be present in either crystalline and/or amorphous form each of which can optionally be present in anhydrous, hydrated or solvated forms.

In a preferred embodiment is provided a crystalline form of (S) 2-Ethoxy-3-(4-{2-[2-methyl-5-(4-methylthiophenyl)-pyrrol-1-yl]-ethoxy}-phenyl)-propionic acid Dibenzylamine salt according to the present invention characterized by its powder X-ray diffraction pattern having peaks expressed as 2θ±0.2 degree at about 8.72, 16.8, 18.5, 19.1, 19.6, 20.6, 21.6, 22.5 and 24.5.

Figure 12:
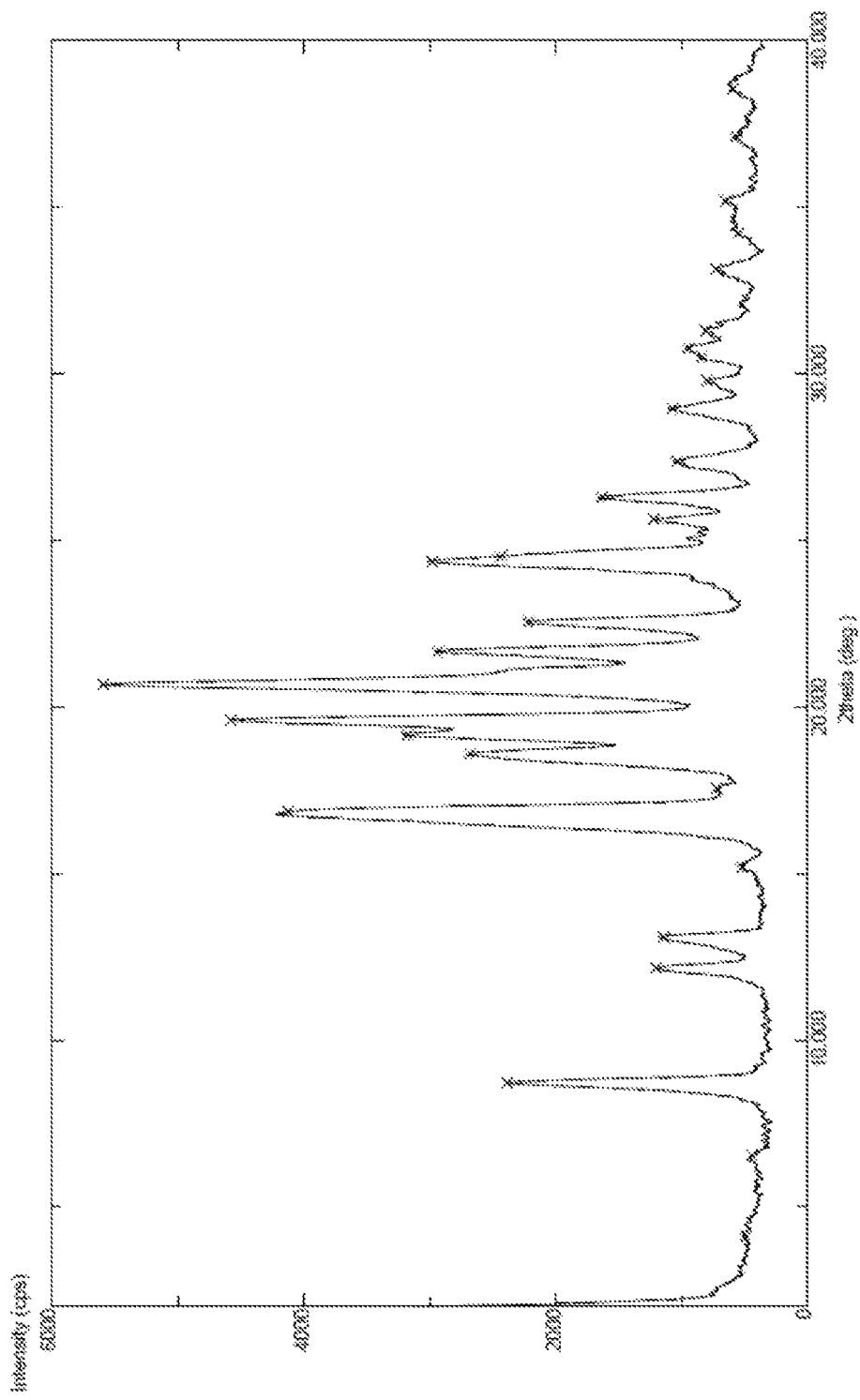
FIG. 12 is a powder X-ray diffraction (XRPD) pattern of crystalline form of (S) 2-Ethoxy-3-(4-{2-[2-methyl-5-(4-methylthiophenyl)-pyrrol-1-yl]-ethoxy}-phenyl)-propionic acid Dibenzylamine salt according to the present invention.
Figure 13:
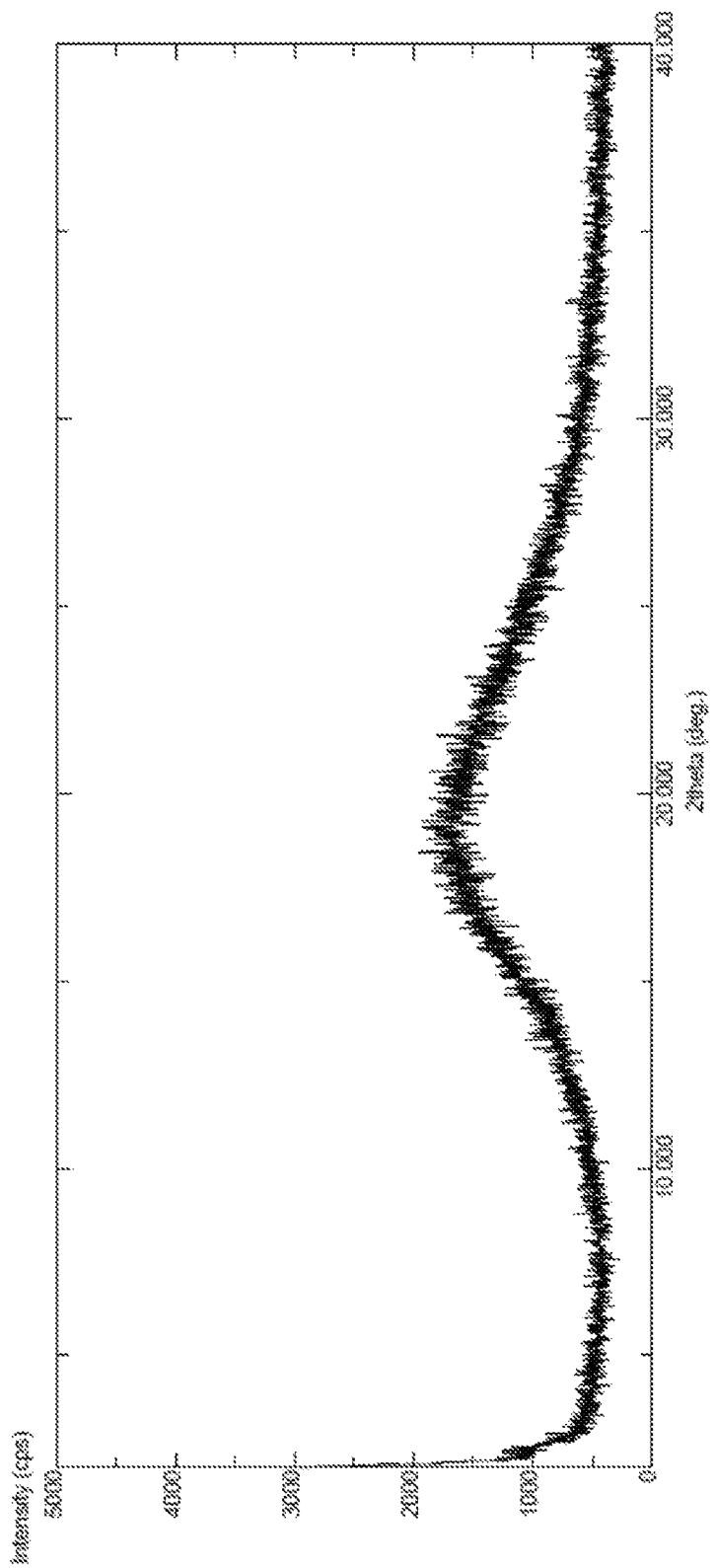
FIG. 13 is a powder X-ray diffraction (XRPD) pattern of amorphous form of (S) 2-Ethoxy-3-(4-{2-[2-methyl-5-(4-methylthiophenyl)-pyrrol-1-yl]-ethoxy}-phenyl)-propionic acid Arginine salt according to the present invention.

In a still further preferred embodiment the crystalline form of (S) 2-Ethoxy-3-(4-{2-[2-methyl-5-(4-methylthiophenyl)-pyrrol-1-yl]-ethoxy}-phenyl)-propionic acid Dibenzylamine salt is further characterized by its powder X-ray diffraction pattern (PXRD) as depicted in FIG. 12.

In an embodiment is provided (S) 2-Ethoxy-3-(4-{2-[2-methyl-5-(4-methylthiophenyl)-pyrrol-1-yl]-ethoxy}-phenyl)-propionic acid imidazole salt. In a further embodiment, (S) 2-Ethoxy-3-(4-{2-[2-methyl-5-(4-methylthiophenyl)-pyrrol-1-yl]-ethoxy}-phenyl)-propionic acid imidazole salt can be present in either crystalline and/or amorphous form each of which can optionally be present in anhydrous, hydrated or solvated forms.

In a preferred embodiment is provided a crystalline form of (S) 2-Ethoxy-3-(4-{2-[2-methyl-5-(4-methylthiophenyl)-pyrrol-1-yl]-ethoxy}-phenyl)-propionic acid imidazole salt according to the present invention characterized by its powder X-ray diffraction pattern having peaks expressed as 2θ±0.2 degree at about 9.40, 14.7, 15.6, 17.3, 21.0, 21.5, 22.5 and 26.2.

Figure 14:
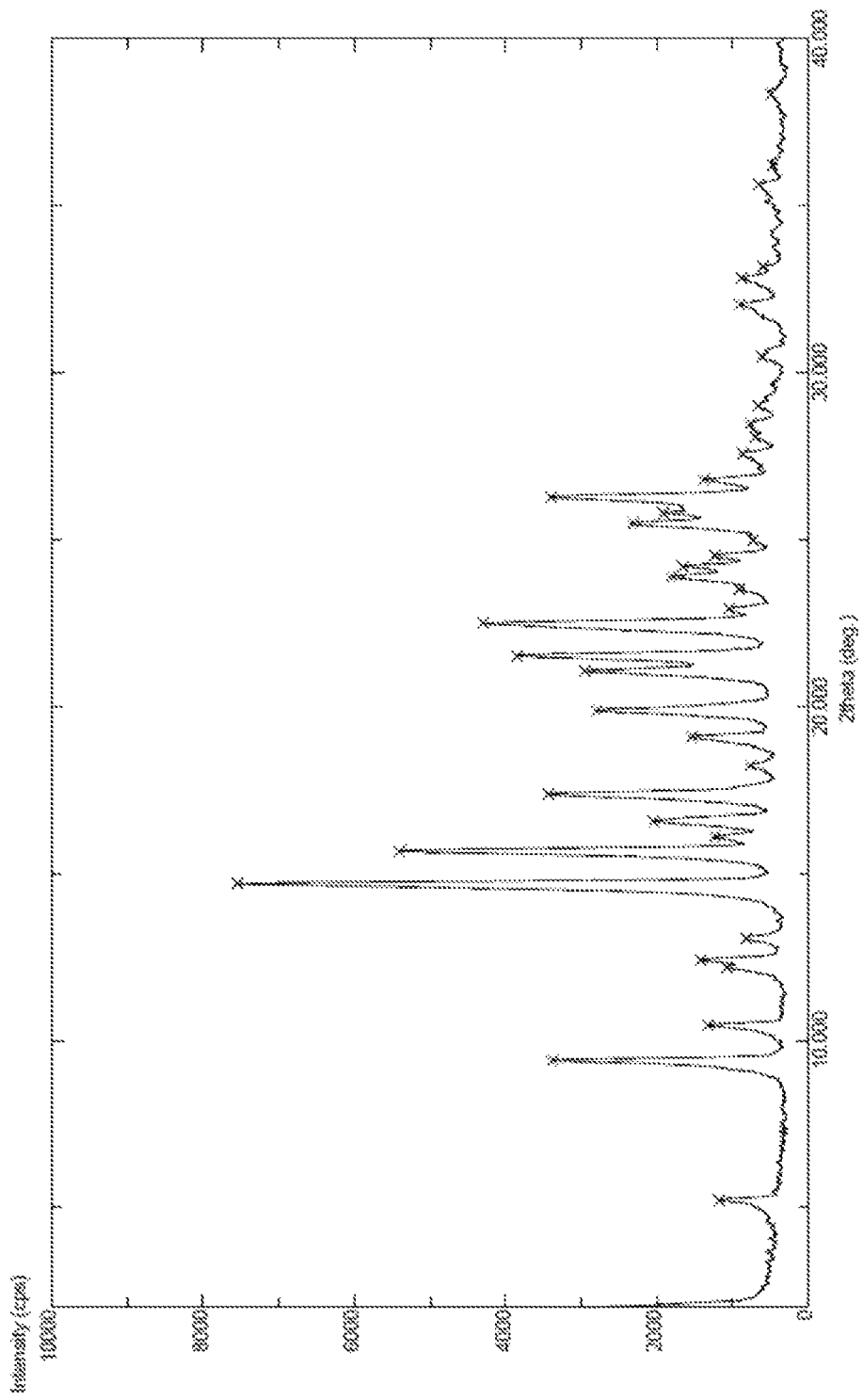
FIG. 14 is a powder X-ray diffraction (XRPD) pattern of crystalline form of (S) 2-Ethoxy-3-(4-{2-[2-methyl-5-(4-methylthiophenyl)-pyrrol-1-yl]-ethoxy}-phenyl)-propionic acid Imidazole salt according to the present invention.

In a still further preferred embodiment the crystalline form of (S) 2-Ethoxy-3-(4-{2-[2-methyl-5-(4-methylthiophenyl)-pyrrol-1-yl]-ethoxy}-phenyl)-propionic acid Imidazole salt is further characterized by its powder X-ray diffraction pattern (PXRD) as depicted in FIG. 14.

Analytical Methods:
i) Chromatographic Purity/Related Substance (by HPLC)
    Column: YMC-pack ODS-AM (type $L_1$) or equivalent; 250×4.6 mm, 5 μm
    Wave length: 294 nm
    Column temp.: 30° C.
    Mobile phase: [Ammonium acetate buffer: Acetonitrile]/[55:45]
    Flow rate: 1 ml/min
    Injection vol.: 5 μl
    Retention time: About 10 mints.
    Run time: 60 mints.
ii) Chromatographic Purity Chiral (by HPLC)
    Column: chiralcel OJ-H: 250×4.6 mm, 5 μm
    Wave length: 294 nm
    Column temp.: 35° C.
    Mobile phase: 0.05%TFA in EtOH:Hexane/(12:88)
    Flow rate: 0.8 ml/min
    Injection vol.: 5 μl
    Run time: 60 mints.

iii) DSC (Differential Scanning Calorimeter):

Weight accurately 2mg to 3mg of sample in a clean aluminum pan, place the lid and seal it with the help of sealing process.

Instrument Detail:
Make: Perkin Elmer
Model: Pyris 1
Software: Pyris 1
Follow the method as describe below:
Initial temperature: 50° C.
Final temperature: 300° C.
Heating rate: 10° C./min
Gas: Nitrogen
Gas Flow: 20 ml/min
Blank Run: Run the blank for baseline correction by placing empty aluminum pans in both sample and reference compartments of the DSC furnace and run a scan using the temperature range and at a heating rate mentioned in Instrumental parameters.

Sample Run: Place the sample preparation in the sample compartment and blank aluminum pan in the reference compartment of the DSC furnace and run a scan using the temperature range and heating rate mentioned as in instrumental parameters using the base line file obtained in the blank run above for the baseline correction.

iv) XRPD Method

Sample Preparation: Place a Sufficient quantity of sample to be analyzed on the sample holder plate and flatten it with the help of another plate to achieve a smooth surface. Record the diffraction pattern as per below instrumental parameters Instrument used: 2 k W XRD
Model: MF2100
Make: Rigaku
Instrument Parameters:
1. X-ray: Cu/40 kV/30 mA
2. Diversion slit: 1°
3. Scattering slit: 1°
4. Receiving slit: 0.15 mm
5. Filter: Ni-kβ filter
6. Counter: Scintillation counter
7. Scan mode: Continuous
8. Scan speed: 4.000°/minute
9. Sampling width: 0.010°
10. Scan axis: 2theta\theta
11. Scan range: 2.0° to 40.0°
12. Theta offcet: 0.000° v) NMR Analysis:

The 1H NMR spectrum & 13C NMR spectrum was obtained for Saroglitazar salts in DMSO-d6 solvent by using Bruker AVANCE II 400 MHz spectrometer instrument.

vi) Mass Spectrum Analysis:

The mass spectrum for Saroglitazar salts were obtained using LCMS 2010 A SHIMADZU instrument by positive/negative chemical ionization mass spectrometry.

In one of the embodiments the salts of Formula (I) prepared according to the present invention, preferably have a purity of at least 98%, more preferably at least 99%.

In one embodiment, some of the salts of the present invention may be used as an intermediate to obtain highly pure acid in Formula (I)

In another embodiment, the salts of the present invention can be formulated to their suitable pharmaceutical compositions for use in humans and other suitable species.

Accordingly, the invention provides a method for the treatment of dyslipidemia, hypertriglyceridemia and diabetes mellitus and conditions associated with these disorders in a mammal such as a human, which method comprises administering an effective, non-toxic and pharmaceutically acceptable amount of a compound of formula (I) and one or more DPP IV inhibitors, to a mammal in need thereof.

In an embodiment the present invention provides an improved process for preparing compound of formula (I) using novel intermediates.

The invention is further exemplified by the following non-limiting examples, which are illustrative representing the preferred modes of carrying out the invention. The invention's scope is not limited to these specific embodiments only but should be read in conjunction with what is disclosed anywhere else in the specification together with those information and knowledge which are within the general understanding of a person skilled in the art.

EXAMPLE-1

Preparation of (S)-α-1-phenylethylamine salt of (S)-α-ethoxy-4-[2-[-methyl-5-[4-(methylthio) phenyl]-1H-pyrrol-1-yl] ethoxy] benzenepropanoic acid In a dry, 100 mL round bottom flask methanol (25 L) was taken and racemic α-ethoxy-4-[2-[-methyl-5-[4-(methylthio) phenyl]-1H-pyrrol-1-yl] ethoxy] benzene propanoic acid ethyl ester (6.3 g) was added at room temperature, under nitrogen. Sodium hydroxide (0.591 g) dissolved in water (6 mL) was added into the reaction mixture and stirred at room temperature for 3 hours to complete hydrolysis. Solvent was removed under reduced pressure. Water (65 mL) was added to concentrate the material. Impurity was removed by solvent washing. Aqueous layer was acidified with acetic acid and extracted with isopropyl acetate. The layer of isopropyl acetate was dried over sodium sulfate. Subsequently (S)-α-phenyl ethylamine (0.965 g) was added to the reaction. Solvent was distilled off to remove maximum isopropyl acetate. To this acetonitrile (55 mL) was added and stirred at room temperature for 4 hours. Solid filtered and dried.

Yield: 2.55 g, HPLC Purity: 97.17%, Chiral purity: 94.19%.

EXAMPLE-2

Preparation of (S)-α-1-phenylethylamine salt of (S)-α-ethoxy-4-[2-[-methyl-5-[4-(methylthio) phenyl]-1H-pyrrol-1-yl] ethoxy] benzenepropanoic acid In a dry, 20 L round bottom flask methanol (6.868 L) was taken and racemic α-ethoxy-4-[2-[-methyl-5-[4-(methylthio)phenyl]-1H-pyrrol-1-yl] ethoxy] benzene-propanoic acid ethyl ester (1.717 g) was added at room temperature under nitrogen. Sodium hydroxide (153.95 g) dissolved in water (1.717 L) was added into the reaction mixture and stirred at room temperature for 3 hours to complete hydrolysis. Solvent was removed under reduced pressure. Water (17.17 L) was added to concentrated material. Impurity was removed by solvent washing. Aqueous layer was acidified with acetic acid and extracted with isopropyl acetate. Isopropyl acetate layer was dried over sodium sulfate. Subsequently (R)-α-phenyl ethylamine (287 g) was added to the reaction. Solvent was distilled off to remove maximum isopropyl acetate. To this, acetonitrile (27.22 L) was added and stirred at room temperature for 24 hours. Solid was filtered. To filtrate added (S)-α-phenyl ethylamine (269.07 g). Reaction mixture was stirred at room temperature for 4.5 hours. Solid was filtered and dried.

Yield: 603 g (72.76% yield), HPLC Purity: 99.21%, Chiral purity: 94.00%.

EXAMPLE-3

Preparation of (S)-α-1-phenylethylamine salt of (S)-α-ethoxy-4-[2-[-methyl-5-[4-(methylthio) phenyl]-1H-pyrrol-1-yl] ethoxy] benzenepropanoic acid In a dry, 20 L round bottom flask 3.640 L methanol was taken and 910 g racemic α-ethoxy-4-[2-[-methyl-5-[4-(methylthio)phenyl]-1H-pyrrol-1-yl]ethoxy] benzene propanoic acid ethyl ester was added into the reaction mixture at room temperature under nitrogen. 84.38 g sodium hydroxide was dissolved in 910 mL water and added into the reaction mixture and stirred at room temperature for 3 hours to complete hydrolysis. Solvent was removed under reduced pressure. 9.1 L water was added to concentrate the material. Impurity was removed by solvent washing. Aqueous layer was acidified with acetic acid and extracted with isopropyl acetate. Isopropyl acetate layer was dried over sodium sulfate. Subsequently 196.65 g (R)-α-phenyl ethylamine was added to the reaction. Solvent was distilled off to remove maximum isopropyl acetate. To this 6.570 L acetonitrile was added and stirred at room temperature for 24 hours. Solid was filtered. To the filtrate added 26.96 g (S)-1-(4-nitrophenyl) ethylamine and 176.98 g (S)-α-phenyl ethylamine. Reaction mixture was stirred at room temperature for 4.5 hr. Solid was filtered and dried.

Yield: 338 g (74.38%), HPLC Purity: 98.16%, Chiral purity: 98.76%.

Similarly, (S)-α-1-phenylethylamine salt of (S)-α-ethoxy-4-[2-[-methyl-5-[4-(methylthio) phenyl]-1H-pyrrol-1-yl] ethoxy] benzenepropanoic acid is prepared in different batches and the results are summarized in table 1 given below.

TABLE 1

| No. | Input | Output | % Yield | Chemical purity | Chiral purity |
|---|---|---|---|---|---|
| 4 | 6.5 g | 2.35 g | 78.48% | 99.43% | 98.23% |
| 5 | 6.5 g | 2.3 g | 76.82% | 99.19% | 97.94% |
| 6 | 829 g | 355.7 g | 97.56% | 99.30% | 92.61% |

Purity (HPLC): 99.70%, Chiral purity: 99.57%

$^1$H NMR: 1.04 (3H, t, J=7.0 Hz, —CH$_3$), 1.49 (3H,d, J=6.8 Hz, —CH$_3$), 2.35 (3H,s, —CH$_3$), 2.50 (3H,s, —SCH$_3$), 2.85 & 2.74 (2H,m, CH$_2$), 3.46 & 3.18 (2H,m, CH$_2$), 3.76 (2H, m, —CH), 4.17 (1H, q, —CH), 4.25 & 3.89 (4H, t, —CH$_2$ & t, —CH$_2$), 6.08 & 5.95 (d, J=3.27 Hz, 2×CH (pyrrole)), 6.58 (dd, J=8.8 Hz, 2×—ArH), 7.04 (dd, J=8.8 Hz, 2×ArH), 7.24 (m, 2×ArH), 7.26 (m, 2×ArH), 7.28 (m, 2×ArH), 7.31 (m, 2×ArH), 7.38 (m, 2×ArH).

$^{13}$C NMR: 12.95, 15.28, 15.89, 22.13, 38.77 43.28, 51.20, 65.50, 66.97, 82.31, 107.25, 108.54, 113.86, 126.65, 128.32, 128.94, 129.69, 130.29, 130.42, 130.86, 132.09, 133.47, 137.22, 140.29, 156.62, 179.15.

ESIMS: 438.2 (M−1) (molecular ion peak of (S)-α-ethoxy-4-[2-[-methyl-5-[4-(methylthio) phenyl]-1H-pyrrol-1-yl] ethoxy] benzenepropanoic acid.

IR: Frequency (cm$^{-1}$): 3441.12, 2970.48, 2920.32, 1624

EXAMPLE-7

Preparation of (S) 2-Ethoxy-3-(4-{2-[2-methyl-5-(4-methylthiophenyl)-pyrrol-1-yl]-ethoxy}-phenyl)-propionic acid Calcium Salt In 250 ml round bottom flask, (S,S)(−,−)-α-Methyl benzylamine (10.0 g, 0.017 mole) salt of 2-ethoxy-3-(4-{2-[2-methyl-5-(4-methylthiophenyl)-pyrrol-1-yl]-ethoxy}-phenyl)-propionic acid was charged. A solution of ethyl acetate (72 ml) and water (50 ml) was added at RT under N$_2$ atm., 50% HCl (4.8 ml) solution was added and stirred for 10 minutes. The organic layer was separated and washed with water. The solvent was distilled out at rotavapor under vacuum at 50-55° C. Free acid compound was obtained. In a 250 ml three necked flask, above oily mass (free acid compd.) was charged and dissolved in methanol (39 ml), added a solution of Sodium hydroxide (0.929 g in 39 ml water) (0.023 mole) and stirred for 15 minutes at RT. The reaction mass was cooled at 10-15° C. and added a solution of calcium acetate (2.05 g in 39 ml water) (0.011 mole) within 5 minutes. Salt was precipitated out and stirred it for 30 minutes. The solid was filtered and washed with water. Dried the solid under vacuum. Yield: 8.0 g (97.8%), HPLC: purity: 98.82%, Chiral purity: 99.52%.

M.P.: 175.7° C.

EXAMPLE-8

Preparation of (S) 2-Ethoxy-3-(4-{2-[2-methyl-5-(4-methylthiophenyl)-pyrrol-1-yl ethoxy phenyl propionic acid Sodium Salt In 250 ml round bottom flask, (S,S)(−,−)α-methyl benzylamine (10.0 g, 0.017 mole) salt of 2-ethoxy-3-(4-{2-[2-methyl-5-(4-methylthiophenyl)-pyrrol-1-yl]-ethoxy}-phenyl)-propionic acid was charged. A solution of Ethyl acetate (72 ml) and water (50 ml) was added at RT under N$_2$ atm., 50% HCl (4.8 ml) solution was added and stirred for 10 minutes. The organic layer was separated and washed with water. The solvent was distilled out using rotavapor under vacuum at 50-55° C. Free acid compound was obtained. In a 250 ml three necked flask, above oily mass (free acid compd.) charged and dissolved in Methanol (50 ml), added Sodium methoxide (0.868 g, 0.016 mole) under nitrogen atmosphere and stirred for 30 minutes at RT. The solvent was distilled out using rotavapor. Solid material was obtained. Triturated the solid material with n-Heptane and stirred for 15 minute. N-Heptane layer was decanted and dissolved the solid again in methanol (40 ml). The solvent was distilled out and dried the solid using rotavapor under vacuum. Yield: 7.9 g, HPLC: purity: 98.50%, Chiral purity: 99.50%.

M.P.: 63.6° C.

EXAMPLE-9

Preparation of (S) 2-Ethoxy-3-(4-{2-[2-methyl-5-(4-methylthiophenyl)-pyrrol-1-yl ethoxy phenyl propionic acid Potassium Salt In 250 ml round bottom flask, (S,S)(−,−)α-Methyl benzylamine (10.0 g, 0.017 mole) salt of 2-ethoxy-3-(4-{2-[2-methyl-5-(4-methylthiophenyl)-pyrrol-1-yl]-ethoxy}-phenyl)-propionic acid was charged. A solution of Ethyl acetate (72 ml) and water (50 ml) was added at RT under N$_2$ atm., 50% HCl (4.8 ml) solution was added and stirred for 10 minutes. The organic layer was separated and washed with water. The solvent was distilled out using rotavapor under vacuum at 50-55° C. Free acid compound was obtained. In a 250 ml three necked flask, above oily mass (free acid compd.) charged and dissolved in Methanol (39 ml), added potassium tert-butoxide (1.81 g, 0.016 mole) under nitrogen atmosphere and stirred for 30 minutes at RT. The solvent was distilled out using rotavapor. Solid material was obtained. Triturated the solid material with n-Hexane (50 ml) and stirred for 15 minute. N-Heptane layer was decanted and dissolved the solid again in methanol (40 ml). The solvent was distilled out and dried the solid using rotavapor under vacuum. Yield: 7.6 g (89.2%) HPLC: purity: 98.60%, Chiral purity: 99.56%.

M.P.: 60.4° C.

EXAMPLE-10

Preparation of (S) 2-Ethoxy-3-(4-{2-[2-methyl-5-(4-methylthiophenyl)-pyrrol-1-yl]-ethoxy}-phenyl)-propionic acid Zinc Salt In 250 ml round bottom flask, (5,5)-α-Methyl benzylamine (10.0 g, 0.017 mole) salt of 2-ethoxy-3-(4-{2-[2-methyl-5-(4-methylthiophenyl)-pyrrol-1-yl]-ethoxy}-phenyl)-propionic acid was charged. A solution of Ethyl acetate (72 ml) and water (50 ml) was added at RT under $N_2$ atm., 50% HCl (4.8 ml) solution was added and stirred for 10 minutes. The organic layer was separated and washed with water. The solvent was distilled out using rotavapor under vacuum 50-55° C. Free acid compound was obtained. In a 250 ml three necked flask, charged above oily mass (free acid compd) and dissolved in Methanol, added a solution of sodium hydroxide (0.929 g in 40 ml water, 0.023 mole) and stirred for 15 minute at RT. The reaction mass was cooled at 10-15° C. and added a solution of Zinc acetate (2.55 g in 40 ml water, 0.011 mole) in 5 minutes. Salt was precipitated out and stirred for further 30 minutes. The solid was filtered and washed with water. Dried the solid under vacuum. Yield: 8.2 g (97.5%), HPLC: purity: 98.97%, Chiral purity: 99.55%.

M.P.: 78.5° C.

EXAMPLE-11

Preparation of (S) 2-Ethoxy-3-(4-{2-[2-methyl-5-(4-methylthiophenyl)-pyrrol-1-yl ethoxy phenyl propionic acid Lithium Salt In 250 ml round bottom flask, (S,S)-α-Methyl benzylamine (10.0 g, 0.017 mole) salt of 2-ethoxy-3-(4-{2-[2-methyl-5-(4-methylthiophenyl)-pyrrol-1-yl]-ethoxy}-phenyl)-propionic acid was charged. A solution of Ethyl acetate (72 ml) and water (50 ml) was added at RT under $N_2$ atm., 50% HCl (4.8 ml) solution was added and stirred for 10 minutes. The organic layer was separated and washed with water. The solvent was distilled out using rotavapor under vacuum at 50-55° C. Free acid compound was obtained. In a 250 ml three necked flask, charged above oily mass (free acid compd.) and dissolved in Methanol (50 ml), added a solution of Lithium hydroxide monohydrate (0.676 g in 4 ml water, 0.016 mole) at RT under nitrogen atmosphere and stirred for 30 minute. The solvent was distilled out using rotavapor. Solid material was obtained. Treated the solid material with n-Hexane (50 ml) and stirred for 15 minute. N-Hexane layer was decanted and dissolved the solid again in methanol (40 ml). The solvent was distilled out and dried the solid using rotavapor under vacuum. Yield: 8.0 g (Quantitative), HPLC: purity: 98.31%, Chiral purity: 99.60%.

M.P.: 85.5° C.

EXAMPLE-12

Preparation of (S) 2-Ethoxy-3-(4-{2-[2-methyl-5-(4-methylthiophenyl)-pyrrol-1-yl ethoxy phenyl propionic acid L-arginine Salt In 250 ml round bottom flask, (S,S)-α-methyl benzylamine (10.0 g, 0.017 mole) salt of 2-ethoxy-3-(4-{2-[2-methyl-5-(4-methylthiophenyl)-pyrrol-1-yl]-ethoxy}-phenyl)-propionic acid was charged. A solution of Ethyl acetate (72 ml) and water (50 ml) was added at RT under $N_2$ atm., 50% HCl (4.8 ml) solution was added and stirred for 10 minutes. The organic layer was separated and washed with water. The solvent was distilled out using rotavapor under vacuum at 50-55° C. Free acid compound was obtained. In a 250 ml three necked flask, charged above oily mass (free acid compd) and dissolved in Methanol (50 ml), added a solution of Lithium arginine (2.8 g in 12 ml water, 0.016 mole) at RT under nitrogen atmosphere and stirred for 30 minutes. The solvent was distilled out using rotavapor. Sticky material was obtained. Treated the sticky material with n-Hexane (50 ml) and stirred for 15 minutes. N-Hexane layer was decanted and dissolved the solid again in methanol (40 ml). The solvent was distilled out and dried the solid using rotavapor under vacuum. Yield: 10.0 g (91.3%), HPLC: purity: 98.67%, Chiral purity: 99.48%.

M.P.: 108.6° C.

EXAMPLE-13

Preparation of (S) 2-Ethoxy-3-(4-{2-[2-methyl-5-(4-methylthiophenyl)-pyrrol-1-yl ethoxy phenyl propionic acid Tromethamine salt In 250 ml round bottom flask, (S,S)-α-Methyl benzylamine (10.0 g, 0.017 mole) salt of 2-ethoxy-3-(4-{2-[2-methyl-5-(4-methylthiophenyl)-pyrrol-1-yl]-ethoxy}-phenyl)-propionic acid was charged. A solution of Ethyl acetate (85 ml) and water (60 ml) was added at RT under $N_2$ atm., 50% HCl (5.2 ml) solution was added and stirred for 10 minutes. The organic layer was separated and washed with water. The solvent was distilled out using rotavapor under vacuum. Free acid compound was obtained. In a 250 ml three necked flask, charged above oily mass (free acid compd) and dissolved in Methanol (70 ml), added a solution of Tromethamine (2.34 g in 5 ml water, 0.019 mole) at RT under nitrogen atmosphere and stirred for 30 minutes. The solvent was distilled out at rotavapor. Solid material was obtained. Treated the solid material with n-Hexane (50 ml) and stirred for 15 minute. N-Hexane layer was decanted and dissolved the solid again in DCM (50 ml). The solvent was distilled out and dried the solid using rotavapor under vacuum. Yield: 11.2 g (93.3%), HPLC: purity: 98.40%, Chiral purity: 99.43

M.P.: 69.0° C.

EXAMPLE-14

Preparation of (S) 2-Ethoxy-3-(4-{2-[2-methyl-5-(4-methylthiophenyl)-pyrrol-1-yl ethoxy phenyl propionic acid L-Lysine salt In 250 ml round bottom flask, (10.0 g, 0.017 mole) (S,S)-α-Methyl benzylamine salt of 2-ethoxy-3-(4-{2-[2-methyl-5-(4-methylthiophenyl)-pyrrol-1-yl]-ethoxy}-phenyl)-propionic acid was charged. A solution of Ethyl acetate (72 ml) and water (50 ml) was added at RT under $N_2$ atm., 50% HCl (4.8 ml) solution was added and stirred for 10 minutes. The organic layer was separated and washed with water. The solvent was distilled out using rotavapor under vacuum. Free acid compound was obtained. In a 250 ml three necked flask, charged above oily mass (free acid compd.) and dissolved in Methanol (50 ml), added a solution of L-lysine (2.4 g in 8 ml water, 0.016 mole) at RT under nitrogen atmosphere and stirred for 30 minute. The solvent was distilled out at rotavapor. Sticky material was obtained.

Treated the solid material with n-Hexane (50 ml) and stirred for 15 minutes. N-Hexane layer was decanted and dissolved the solid again in methanol. The solvent was distilled out and dried the solid using rotavapor under vacuum. Yield: 8.8 g (84.2%), HPLC: purity: 98.91%, Chiral purity: 99.46%. M.P.: 82.4° C.

EXAMPLE-15

Preparation of Meglumine salt (i.e. N-Methyl-D-glucamine) of (S) 2-Ethoxy-3-(4-{2-[2-methyl-5-(4-methylthiophenyl)-pyrrol-1-yl ethoxy phenyl propionic acid In 100 ml round bottom flask, (S,S)-α-Methyl benzylamine (5.0 g, 8.93 mmol) salt of 2-ethoxy-3-(4-{2-[2-methyl-5-(4-methylthiophenyl)-pyrrol-1-yl]-ethoxy}-phenyl)-propionic acid was charged. A solution of Ethyl acetate (35 ml) and water (25 ml) was added at RT under $N_2$ atm. To the suspension 4 ml dilute HCl (2 ml water+2 ml HCl) solution was added and stirred for 10 minutes. The organic layer was separated and washed with water followed by sodium chloride solution and dried over sodium sulphate. The solvent was distilled out using rotavapor under vacuum. Free acid compound was obtained. To the oily mass (free acid compd.) methanol (25 ml) was added and stirred to dissolve completely. To the clear reddish solution added a solution of meglumine (1.6 g dissolved in 10 ml methanol+3 ml water, 8.0 mmol) at RT under nitrogen atmosphere. Clear solution was stirred for 10 minutes under nitrogen atmosphere. The solvent was distilled out using rotavapor. Sticky material was obtained. Again added 25 ml methanol to the sticky material. After getting clear solution, solvent was distilled out under vacuum at 45-50° C. Solid was obtained. To the solid n-Hexane was added and stirred for 15 minutes. N-Hexane was decanted. This operation was repeated for another two times to get free flowing solid. The solid was dried under vacuum at 40° C. for two hours.

Yield: 4.850 g (85.56%), HPLC: purity: 99.15%, Chiral purity: 99.40 M.P.: 72.7° C.

EXAMPLE-16

Preparation of Benethamine salt (i.e. N-Benzyl-2-phenylethylamine) of (S) 2-Ethoxy-3-(4-{2-[2-methyl-5-(4-methylthiophenyl)-pyrrol-1-yl ethoxy phenyl propionic acid In 250 ml round bottom flask, (5,5)-α-Methyl benzylamine (0.500 g, 0.892 mmole) salt of 2-ethoxy-3-(4-{2-[2-methyl-5-(4-methylthiophenyl)-pyrrol-1-yl]-ethoxy}-phenyl)-propionic acid was charged. A solution of Ethyl acetate (3.5 ml) and water (2.5 ml) was added at RT under $N_2$ atm. To the suspension 1 ml dilute HCl solution was added and stirred for 10 minutes to dissolved the solid completely. The organic layer was separated and washed with water. Dried the layer over sodium sulphate and the solvent was distilled out using rotavapor under vacuum. Free acid compound was obtained. To the oily mass (free acid compound) acetonitrile (2 ml) was added and stirred to dissolve completely. To the clear reddish solution added benethamine (0.188 g, 0.982 mmol) at RT under $N_2$ atmosphere. Hazy solution was stirred for 3 hours at room temperature under $N_2$ atmosphere. Kept at 0-5° C. overnight. Solvent was distilled out under vacuum. Sticky material was obtained. Added n-Hexane (10 ml) and stirred for 15 minute. N-Hexane was decanted. The solid was dried under vacuum at 40° C. for 2 hours.

Yield: 0.530 g (91.0%), HPLC: purity: 96.97%, Chiral purity: 100%. M.P.: 103.1° C.

EXAMPLE-17

Preparation of (S) 2-Ethoxy-3-(4-{2-[2-methyl-5-(4-methylthiophenyl)-pyrrol-1-yl ethoxy phenyl propionic acid Piperazine Salt In a 50 ml round bottom flask, (S,S)-α-Methyl benzylamine (10.0 g, 0.017 mole) salt of 2-ethoxy-3-(4-{2-[2-methyl-5-(4-methylthiophenyl)-pyrrol-1-yl]-ethoxy}-phenyl)-propionic acid was charged. A solution of Ethyl acetate (21 ml) and water (15 ml) was added at RT under $N_2$ atm., 50% HCl (2.0 ml) solution was added and stirred for 10 minutes. The organic layer was separated and washed with water. The solvent was distilled out using rotavapor under vacuum at. Free acid compound was obtained. In a 50 ml three necked flask, charged above oily mass (free acid compd.) and dissolved in Methanol (25 ml), added a solution of piperazine (0.415 g in 10 ml methanol, 0.004 mole) at RT under nitrogen atmosphere and stirred for 30 minute. The solvent was distilled out under vacuum. Sticky material was obtained. Treated the sticky material with n-Hexane (50 ml) and stirred for 15 minute. N-Hexane layer was decanted and dissolved the solid again in acetone (10 ml). The solvent was distilled out and dried the solid using rotavapor under vacuum.

Yield: 2.8 g, HPLC: purity: 97.62%, Chiral purity: 99.62%.

M.P.: 74.5° C.

EXAMPLE-18

Preparation of Benzylamine salt of (S) 2-Ethoxy-3-(4-{2-[2-methyl-5-(4-methylthiophenyl)-pyrrol-1-yl ethoxy phenyl propionic acid In 250 ml round bottom flask, (S,S)(−,−) Methyl benzylamine (10.0 g, 17.8 mmole) salt of 2-ethoxy-3-(4-{2-[2-methyl-5-(4-methylthiophenyl)-pyrrol-1-yl]-ethoxy}-phenyl)-propionic acid was charged. A solution of Ethyl acetate (70 ml) and water (50 ml) was added at RT under $N_2$ atm. To the suspension added 7 ml dilute HCl solution and stirred for 10 minutes. The organic layer was separated and washed with water. Dried the layer over sodium sulphate. The solvent was distilled out using rotavapor under vacuum. Free acid compound was obtained. To the oily mass (free acid compd.) added acetonitrile (100 ml) and stirred to dissolved completely. To the clear reddish solution, added benzylamine (1.9 g, 17.8 mmol) at RT under $N_2$ atmosphere. Hazy solution was stirred for 1 hour at RT under $N_2$ atmosphere. Precipitated solid was filtered, washed with acetonitrile. Free flowing solid was dried at 50-55° C.

Yield: 8.5 g (85.56%), HPLC: purity: 97.44%, Chiral purity: ND, M.P.: 123° C.

ESI-MS: (M+H): 547.4

EXAMPLE-19

Preparation of (S) 2-Ethoxy-3-(4-{2-[2-methyl-5-(4-methylthiophenyl)-pyrrol-1-yl ethoxy phenyl propionic acid Dibenzylamine Salt In 250 ml round bottom flask, (S,S)(−,−)α-Methyl benzylamine salt (10.0 g, 17.8 mmole) salt of 2-ethoxy-3-(4-

{2-[2-methyl-5-(4-methylthiophenyl)-pyrrol-1-yl]-ethoxy}-phenyl)-propionic acid was charged. A solution of Ethyl acetate (70 ml) and water (50 ml) was added at RT under $N_2$ atm. To the suspension added 7 ml dilute HCl solution and stirred for 10 minutes. The organic layer was separated and washed with water. Dried the layer over sodium sulphate. The solvent was distilled out using rotavapor under vacuum. Free acid compound was obtained. To the oily mass (free acid compd.) added acetonitrile (35 ml) and stirred to dissolved completely. To the clear reddish solution, added Dibenzylamine (3.5 g, 17.8 mmol) at RT under $N_2$ atmosphere. Hazy solution was stirred for 1 hour at RT under $N_2$ atmosphere. Precipitated solid was filtered, washed with acetonitrile. Free flowing solid was dried at 50-55° C.

Yield: 9.2 g (81.0%), HPLC: purity: 97.16%, Chiral purity: 100%
M.P.: 61.5° C.

EXAMPLE-20

Preparation of Epolamine [i.e 2-(pyrrolidine-1-yl) ethanol] Salt of (S) 2-Ethoxy-3-(4-{2-[2-methyl-5-(4-methylthiophenyl)-pyrrol-1-yl ethoxy phenyl propionic acid In 50 mL round bottom flask, charged (5.0 g) (8.9 mmole) (S,S)(−,−)α-Methyl benzylamine salt of 2-ethoxy-3-(4-{2-[2-methyl-5-(4-methylthiophenyl)-pyrrol-1-yl]-ethoxy}-phenyl)-propionic acid, 35 mL Ethyl acetate followed by 25 mL water at RT under $N_2$ atm. To the suspension added 3.5 mL dilute HCl solution and stirred for 10 mints, to dissolve the solid completely. Layer was separated. Organic layer was washed with water (20 ml×2) followed by brine wash (20 ml×1), dried over sodium sulphate and distilled out solvent under vacuum. (Free acid compd obtd as an oil). To the oily mass (free acid compd) added acetonitrile (30 ml) and stirred to dissolved completely. To the clear reddish solution, added 2-(pyrrolidine-1-yl)ethanol (1.03 g, 8.92 mmol) at RT under $N_2$ atm., hazy solution was stirred for 3 hours at room temperature under $N_2$ atmosphere. Kept at 0-5° C. for overnight. Solid do not precipitate, distilled out solvent under vacuum. Sticky material obtained. Triturated with n-Hexane (2×50 ml), decanted n-Hexane layer, then again dissolved in methylene chloride (10 ml), added into n-heptane under stirring, solid do not precipitate, distilled out solvent under vacuum at 50-55° C.

Yield: 5.1 g (quantitative), HPLC: purity: 96.76%, Chiral purity: 99.82%

EXAMPLE-21

Preparation of Imidazole [i.e 1H-Imidazole] salt of (S) 2-Ethoxy-3-(4-{2-[2-methyl-5-(4-methylthiophenyl)-pyrrol-1-yl ethoxy phenyl propionic acid In 100 ml round bottom flask, charged (5.0 g) (8.92 mmole) (S,S)(−,−)α-Methyl benzylamine salt of 2-ethoxy-3-(4-{2-[2-methyl-5-(4-methylthiophenyl)-pyrrol-1-yl]-ethoxy}-phenyl)-propionic acid, 35 ml Ethyl acetate followed by 25 ml water at RT under $N_2$ atm. To the suspension added 3.4 ml dilute HCl solution and stirred for 10 mints, to dissolve the solid completely. layer was separated. Organic layer was washed with water (20 ml×2), dried over sodium sulphate and distilled out solvent under vacuum. (Free acid compd. obtd. as an oil-4.2 g). To the oily mass (free acid compd) added acetonitrile (30 ml) and stirred to dissolved completely. To the clear reddish solution, added 1H imidazole (0.608 g, 8.92 mmol) dissolved in 10 ml acetonitrile at RT under $N_2$ atm., hazy solution was stirred for 2 hours at room temperature under $N_2$ atmosphere. Kept at 0-5° C. for overnight. Solvent distilled off completely under vacuum, added n-hexane (2×50 ml) and stirred for 10 minutes, decanted n-hexane, oily material dissolved in methylene chloride (10 ml), dumped into 100 ml n-heptane under stirring, sticky semi solid was scratched and stirred for 1 hour at room temperature. Free flowing solid was filtered, washed with n-heptane (2×20 ml), suck dried. Solid was dried under vacuum at 50-55° C.

Yield: 4.2 g (93%), HPLC: purity: 97.00%, Chiral purity: 100%, M.P.: 106.6° C.

EXAMPLE-22

Preparation of Triethanolamine Salt of (S) 2-Ethoxy-3-(4-{2-[2-methyl-5-(4-methylthiophenyl)-pyrrol-1-yl ethoxy phenyl propionic acid In 250 ml round bottom flask, charged (5.0 g) (8.92 mmole) (S,S)(−,−)α-Methyl benzylamine of 2-ethoxy-3-(4-{2-[2-methyl-5-(4-methylthiophenyl)-pyrrol-1-yl]-ethoxy}-phenyl)-propionic acid, 35 ml Ethyl acetate followed by 25 ml water at RT under $N_2$ atm. To the suspension added 3.5 ml dilute HCl solution and stirred for 10 mints to dissolve the solid completely. Layer was separated. Organic layer was washed with water (30 ml×2) followed by brine wash (30 ml×1). Dried over sodium sulphate and distilled out solvent under vacuum. (Free acid compound obtained as oil-4.3 g). To the oily mass (free acid compd) added acetonitrile (30 ml) and stirred to dissolved completely. To the clear reddish solution, added triethanol amine (1.34 g, 8.92 mmol) diluted with 10 ml acetonitrile at RT under $N_2$ atm., clear solution was stirred for 2-3 hours at room temperature under $N_2$ atmosphere. Kept at 0-5° C. for overnight. Solvent distilled off completely under vacuum, added n-hexane (10 ml) and stirred for 10 minutes, distilled off n-hexane, oily material dissolved in methylene chloride (10 ml), dumped into 100 ml n-heptane under stirring, sticky oily material was scratched and stirred for 2 hours at room temperature. Solid was not precipitated, distilled out solvent under vacuum at 50-55° C. Oily /pasty material was obtained.

Yield: 5.8 g (Quantitative yield), HPLC: purity: 96.80%, Chiral purity: 100%

EXAMPLE-23

Preparation of Ethanolamine Salt of (S) 2-Ethoxy-3-(4-{2-[2-methyl-5-(4-methylthiophenyl)-pyrrol-1-yl ethoxy phenyl propionic acid In 50 ml round bottom flask, charged (5.0 g) (8.92 mmole) (S,S)(−,−)α-Methyl benzylamine salt of 2-ethoxy-3-(4-{2-[2-methyl-5-(4-methylthiophenyl)-pyrrol-1-yl]-ethoxy}-phenyl)-propionic acid, 35 ml Ethyl acetate followed by 25 ml water at RT under $N_2$ atm. To the suspension added 3.5 ml dilute HCl solution (1.7 ml HCl+1.7 ml water) and stirred for 10 mints, to dissolve the solid completely. Layer was separated. Organic layer was washed with water (20 ml×2) followed by brine wash (20 ml×1), dried over sodium sulphate and distilled out solvent under vacuum. (Free acid compd obtd as an oil). To the oily mass (free acid compd) added acetonitrile (30 ml) and stirred to dissolved completely. To the clear reddish solution, added monoethanol amine (0.546g, 8.92 mmol) diluted with 10 ml acetonitrile at RT under $N_2$ atm., hazy solution was stirred for 2 hours at room temperature under N₂ atmosphere. Solvent distilled off completely under vacuum, oily material dissolved in methylene chloride (10 ml), dumped into 100 ml n-heptane under stirring, sticky oily material was scratched and stirred for 1 hour at room temperature. Solid was not precipitated, distilled out solvent under vacuum at 50-60° C. Oily/pasty material obtained.

Yield: 4.7 g (Quantitative yield), HPLC purity: 97.06%, Chiral purity: 100%

EXAMPLE-24

Preparation of Choline Salt (i.e 2-Hydroxy-N,N,N-trimethylethanaminium hydroxide or choline hydroxide) of (S) 2-Ethoxy-3-(4-{2-[2-methyl-5-(4-methylthiophenyl)-pyrrol-1-yl ethoxy phenyl propionic acid In 50 ml round bottom flask, charged (3.0 g) (5.35 mmole) (S,S)(−,−)α-Methyl benzylamine salt of 2-ethoxy-3-(4-{2-[2-methyl-5-(4-methylthiophenyl)-pyrrol-1-yl]-ethoxy}-phenyl)-propionic acid, 21 ml Ethyl acetate followed by 15 ml water at RT under N₂ atm. To the suspension added 2 ml dilute HCl solution (1 ml HCl+1 ml water) and stirred for 10 mints to dissolve the solid completely. The layer was separated. Organic layer was washed with water (15 ml×2), dried over sodium sulphate and distilled out solvent under vacuum. (Free acid compd. obtd as an oil-2.4 g). To the oily mass (free acid compd-2.4 g) added acetonitrile (15 ml) and stirred to dissolved completely. To the clear reddish solution, added 3.24 ml of 20% choline hydroxide solution (0.649 g, 5.35 mmol) at RT under N₂ atm., hazy solution was stirred for 2 hours at room temperature under N₂ atmosphere. Kept in freeze for overnight. Solvent distilled off completely under vacuum, gummy material obtained, added n-hexane (30 ml), stirred & decanted, again added n-hexane (30 ml), stirred & decanted, dissolved gummy material in methylene chloride (10 ml), dumped into 100 ml n-heptane under stirring, sticy oily material was scratched and stirred for 2 hour at room temperature. Solid was not precipitated, distilled out solvent under vacuum at 50-60° C.

Yield: 2.9 g (100%), HPLC: purity: 94.01%, Chiral purity: 100%

EXAMPLE-25

Preparation of (s)-☐-phenyl ethylamine salt (S)-2-Ethoxy-3-(4-{2-[2-methyl-5-(4-methylthiophenyl)pyrrol-1-yl]-ethoxy}-phenyl)propanoic acid In a 50 mL flask (S)-☐-phenyl ethylamine salt of (S)-2-Ethoxy-3-(4-{2-[2-methyl-5-(4-methylthiophenyl)pyrrol-1-yl]-ethoxy}-phenyl)propanoic acid (5 g), water (5 mL) and isopropyl acetate (25 mL) were mixed under N₂ atmosphere at 25-30° C. To the mixture 35% Conc. HCl (1.11 mL) was added slowly with stirring. It was stirred vigorously up to solid dissolved completely at 25-30° C. It was transferred into the separating funnel. The organic layer was collected and washed with water (2.5 mL). It was dried over anhydrous sodium sulfate. The solvent was distilled out under reduced pressure on Buchi Rota vapour to obtain thick liquid. (Wt.: 3.9 g)

EXAMPLE-26

Preparation of free acid of (S)-2-Ethoxy-3-(4-{2-[2-methyl-5-(4-methylthiophenyl)pyrrol-1-yl]-ethoxy}-phenyl)propanoic acid In a 25 mL flask Magnesium salt of (S)-2-Ethoxy-3-(4-{2-[2-methyl-5-(4-methylthiophenyl)pyrrol-1-yl]-ethoxy}-phenyl)propanoic acid (2 g), water (2 mL) and ethyl acetate (10 mL) were mixed under N₂ atmosphere at 25-30° C. To the mixture 35% Conc. HCl (0.55 mL) was added slowly with stirring. It was stirred vigorously till solid dissolved completely at 25-30° C. It was transferred into the separating funnel. The organic layer was collected and washed with water (2×2 mL). It was dried over anhydrous sodium sulfate. The solvent was distilled out under reduced pressure on Buchi Rota vapour to obtain thick liquid free acid. (Wt.: 1.9 g)

EXAMPLE-27

Preparation of Dicyclohexylamine salt of (S)-2-Ethoxy-3-(4-{2-[2-methyl-5-(4-methylthiophenyl)pyrrol-1-yl]-ethoxy}-phenyl)propanoic acid (S)-2-Ethoxy-3-(4-{2-[2-methyl-5-(4-methylthiophenyl)pyrrol-1-yl]-ethoxy}-phenyl)propanoic acid (3.9 g) was freshly prepared and dissolved in acetonitrile (25 mL) at 25-30° C. To the clear solution dicyclohexylamine (1.61 g) was added with stirring and stirred for 24 h at 25-30° C., solid salt was precipitated. It was diluted with acetonitrile (15 mL). The dicyclohexylamine salt was filtered and washed with acetonitrile (3×5 mL). It was dried under vacuum in the flask.

Wt.: 2.3 g, % Y-41.6%, % Purity by HPLC-98.9%, m.p. 98-100° C.

$^1$H NMR (CDCl₃, 300 MHz): δ 1.08 (t, 3H), 1.11-1.1.24 (m, 5H), 1.40-1.44 (m, 5H), 1.60 (m, 2H), 1.75-1.79 (m, 4H), 1.97-2.00 (m, 4H), 2.36 (s, 3H), 2.50 (s, 3H), 2.83-2.95 (m,4H), 3.27 (m, 1H), 3.62 (m, 1H), 3.76 (m, 1H), 3.89 (t, 2H), 4.24 (t, 2H), 5.94 (d, 1H, J=3.3 Hz), 6.08 (d, 1H, J=3.3 Hz), 6.59 (d, 2H, J=8.7 Hz), 7.15 (d, 2H, J=8.7 Hz), 7.26-7.34 (m, 4H).

EXAMPLE-28

Preparation of (S)-α-naphthylethylamine salt of (S)-2-Ethoxy-3-(4-{2-[2-methyl-5-(4-methylthiophenyl)pyrrol-1-yl]-ethoxy}-phenyl)propanoic acid S)-2-Ethoxy-3-(4-{2-[2-methyl-5-(4-methylthiophenyl)pyrrol-1-yl]-ethoxy}-phenyl)propanoic acid (1.95 g) was freshly prepared and dissolved in acetonitrile (20 mL) at 25-30° C. To the clear solution (S)-α-naphthylethylamine (0.763 g) was added with stirring, solid salt was precipitated. It was heated to reflux temperature and stirred for 10 min. at 80-82° C. It was cooled to 25-30° C. and stirred for 15 min. at 25-30° C. The (S)-α-naphthylethylamine salt was filtered and washed with acetonitrile (3×10 mL). It was dried under vacuum in the flask.

Wt.: 2.2 g, % Y-80.9%, % Purity by HPLC-98.9%, m.p. 153-154° C.

$^1$H NMR (CDCl₃, 300 MHz): δ 0.95 (t, 3H), 1.65 (d, 3H), 2.33 (s, 3H), 2.48 (s, 3H), 2.56 (m, 1H), 2.71 (m, 1H), 3.03 (m, 1H), 3.37 (m, 1H), 3.62 (m, 1H), 3.83 (t, 2H), 4.22 (t, 2H), 5.14 (q, 1H), 5.94 (d, 1H, J=3.3 Hz), 6.08 (d, 1H, J=3.3 Hz), 6.48 (d, 2H, J=8.7 Hz), 6.86 (d, 2H, J=8.7 Hz), 7.23-7.31 (m, 4H), 7.44-7.53 (m, 3H), 7.74 (m, 2H), 7.82 (m, 1H), 7.98 (m, 1H)

m/z: 440 (M+H)⁺, 100%.

EXAMPLE-29

Preparation of (S)-α-3-methoxyphenylethylamine salt of (S)-2-Ethoxy-3-(4-{2-[2-methyl-5-(4-methylthiophenyl)pyrrol-1-yl]-ethoxy}-phenyl)propanoic acid (S)-2-Ethoxy-3-(4-{2-[2-methyl-5-(4-methylthiophenyl)pyrrol-1-yl]-ethoxy}-phenyl)propanoic acid (1.56 g) was freshly prepared and dissolved in acetonitrile (15 mL) at 25-30° C. To the clear solution (S)-α-3-methoxyphenylethylamine (0.540 g) was added with stirring and stirred for 30 min. at 25-30° C., solid salt was precipitated. The (S)-α-3-methoxyphenylethylamine salt was filtered and washed with acetonitrile (3×3 mL). It was dried under vacuum in the flask.

Wt.: 1.7 g, % Y-80.9%, % Purity by HPLC-98.5% , m.p. 139-141° C.

$^1$H NMR (CDCl$_3$, 300 MHz): δ 0.98 (t, 3H), 1.51 (d, 3H), 2.35 (s, 3H), 2.49 (s, 3H), 2.61 (m, 1H), 2.76 (m, 1H), 3.06 (m, 1H), 3.40 (m, 1H), 3.63 (m, 1H), 3.71 (s, 3H), 3.89 (t, 2H), 4.15 (q, 1H), 4.25 (t, 2H), 5.37 (s,br, —NH$_2$, 2H), 5.94 (d, 1H, J=3.3 Hz), 6.07 (d, 1H, J=3.3 Hz), 6.55 (d, 2H, J=8.7 Hz), 6.77 (m, 1H), 6.99 (m, 4H), 7.18-7.33 (m, 5H).

m/z: 440 (M+H)$^+$, 100%

The following salts were prepared following processes similar to those above along with suitable modifications which are within the scope of a skilled person.

EXAMPLE-30

Preparation of (S)-α-4-mehoxyphenylethylamine salt of (S)-2-Ethoxy-3-(4-{2-[2-methyl-5-(4-methylthiophenyl)pyrrol-1-yl]-ethoxy}-phenyl)propanoic acid (S)-2-Ethoxy-3-(4-{2-[2-methyl-5-(4-methylthiophenyl)pyrrol-1-yl]-ethoxy}-phenyl)propanoic acid (1.56 g) was reacted with (S)-α-4-methoxyphenylethylamine (0.555 g) in acetonitrile.

Wt.: 1.9 g, % Y-90.4%, % Purity by HPLC-98.6%, m.p. 145-147° C.

$^1$H NMR (CDCl$_3$, 300 MHz): δ 0.96 (t, 3H), 1.51 (d, 3H), 2.35 (s, 3H), 2.49 (s, 3H), 2.58 (m, 1H), 2.71 (m, 1H), 2.98 (m, 1H), 3.36 (m, 1H), 3.55 (m, 1H), 3.66 (t, 3H), 3.89 (t, 2H), 4.14 (q, 1H), 4.25 (m, 2H), 5.80 (s, br, 2H, -NH$_2$), 5.94 (d, 1H, J=3.3 Hz), 6.08 (d, 1H, J=3.3 Hz), 6.56 (d, 2H, J=8.7 Hz), 6.76 (d, 2H, J=8.7 Hz), 6.98 (d, 2H), 7.24-7.36 (m, 6H)

m/z: 440 (M+H)$^+$, 100%

EXAMPLE-31

Preparation of (S)-α-4-chlorophenylethylamine salt of (S)-2-Ethoxy-3-(4-{2-[2-methyl-5-(4-methylthiophenyl)pyrrol-1-yl]-ethoxy}-phenyl)propanoic acid (S)-2-Ethoxy-3-(4-{2-[2-methyl-5-(4-methylthiophenyl)pyrrol-1-yl]-ethoxy}-phenyl)propanoic acid (1.56 g) was reacted with (S)-α-4-chlorophenylethylamine (0.555 g) in acetonitrile.

Wt.: 1.9 g, % Y-89.6%, % Purity by HPLC-98.5% , m.p. 161-163° C.

$^1$H NMR (CDCl$_3$, 300 MHz): δ 0.99 (t, 3H), 1.47 (d, 3H), 2.35 (s, 3H), 2.49 (s, 3H), 2.68 (m, 1H), 2.78 (m, 1H), 3.10 (m, 1H), 3.35 (m, 1H), 3.66 (dd, 1H), 3.90 (t, 2H), 4.10 (q, 1H), 4.26 (t, 2H), 4.74 (s,br, 2H, -NH$_2$), 5.94 (d, 1H, J=3.3 Hz), 6.08 (d, 1H, J=3.3 Hz), 6.57 (d, 2H, J=8.7 Hz), 6.99 (d, 2H), 7.24-7.35 (m, 8H).

m/z: 440 (M+H)$^+$, 100%

EXAMPLE-32

Preparation of (S)-α-4-methylphenylethylamine salt of (S)-2-Ethoxy-3-(4-{2-[2-methyl-5-(4-methylthiophenyl)pyrrol-1-yl]-ethoxy}-phenyl)propanoic acid (S)-2-Ethoxy-3-(4-{2-[2-methyl-5-(4-methylthiophenyl)pyrrol-1-yl]-ethoxy}-phenyl)propanoic acid (1.56 g) was reacted with (S)-α-)-α-4-methylphenylethylamine (0.482 g) in acetonitrile.

Wt.: 1.85 g, % Y-90.2%, % Purity by HPLC-98.6% , m.p. 152-154° C.

$^1$H NMR (CDCl$_3$, 300 MHz): δ 0.97 (t, 3H), 1.51 (d, 3H), 2.24 (s, 3H), 2.35 (s, 3H), 2.49 (s, 3H), 2.58 (m, 1H), 2.71 (m, 1H), 2.99 (m, 1H), 3.36 (m, 1H), 3.55 (dd, 1H), 3.90 (t, 2H), 4.17 (q, 1H), 4.25 (m, 2H), 5.60 (s, br, -NH$_2$), 5.94 (d, 1H, J=3.3 Hz), 6.08 (d, 1H, J=3.3 Hz), 6.56 (d, 2H, J=8.7 Hz), 6.97 (d, 2H, J=8.7 Hz), 7.06 (d, 2H), 7.24-7.33 (m, 6H).

m/z: 440 (M+H)$^+$, 100%

EXAMPLE-33

Preparation of 1-Adamantanamine salt of (S)-2-Ethoxy-3-(4-{2-[2-methyl-5-(4-methylthiophenyl)pyrrol-1-yl]-ethoxy}-phenyl)propanoic acid (S)-2-Ethoxy-3-(4-{2-[2-methyl-5-(4-methylthiophenyl)pyrrol-1-yl]-ethoxy}-phenyl)propanoic acid (1.95 g) was freshly prepared from Mg salt of (S)-2-Ethoxy-3-(4-{2-[2-methyl-5-(4-methylthiophenyl)pyrrol-1-yl]-ethoxy}-phenyl)propanoic acid (2 g) and dissolved in ethylacetate (10mL) at 25-30° C. To the clear solution 1-adamantanamine (0.670 g) was added with stirring and stirred for 1.5 h at 25-30° C., solid salt was precipitated. It was diluted with 40 mL ethyl acetate. The 1-adamantanamine salt was filtered and washed with ethylacetate (2×10 mL). It was dried under vacuum in the flask.

Wt.: 1.9 g, % Y-72.0%, % Purity by HPLC-98.7%

EXAMPLE-34

Preparation of 1-adamantanemethylamine salt of (S)-2-Ethoxy-3-(4-{2-[2-methyl-5-(4-methylthiophenyl)pyrrol-1-yl]-ethoxy}-phenyl)propanoic acid 1-Adamantanemethylamine salt of (S)-2-Ethoxy-3-(4-{2-[2-methyl-5-(4-methylthiophenyl)pyrrol-1-yl]-ethoxy}-phenyl)propanoic acid was prepared following above procedure from (S)-2-Ethoxy-3-(4-{2-[2-methyl-5-(4-methylthiophenyl)pyrrol-1-yl]-ethoxy}-phenyl)propanoic acid (0.975 g)

Wt.: 0.7 g, % Y-52.0%, % Purity by HPLC-99.1%

EXAMPLE-35

Preparation of Diphenylamine salt of (S)-2-Ethoxy-3-(4-{2-[2-methyl-5-(4-methylthiophenyl)pyrrol-1-yl]ethoxy}phenyl)propanoic acid (S)-2-Ethoxy-3-(4-{2-[2-methyl-5-(4-methylthiophenyl)pyrrol-1-yl]ethoxy}phenyl)propanoic acid (3.9 g) was freshly prepared and dissolved in acetonitrile (40 mL) at 25-30° C. To the clear solution diphenylamine (1.5 g) was added with stirring and stirred for 2 h at 25-30° C. It was cooled to 0-5° C. and stirred for 20 h. Solid was not precipitated. The solvent was distilled out under reduced pressure on Buchi Rota vapour to obtain thick liquid.

Wt.: 5.1 g, % Y-94.0%.

EXAMPLE-36

Preparation of Diethylamine salt of (S)-2-Ethoxy-3-(4-{2-[2-methyl-5-(4-methylthiophenyl)pyrrol-1-yl]ethoxy}phenyl)propanoic acid (S)-2-Ethoxy-3-(4-{2-[2-methyl-5-(4-methylthiophenyl)pyrrol-1-yl]ethoxy} phenyl)propanoic acid (1.95 g) was freshly prepared and dissolved in isopropylacetate (20 mL) at 25-30° C. To the clear solution diethylamine (0.46 g) was added with stirring and stirred for 18 h at 25-30° C., solid did not precipitated. The solvent was distilled out under reduced pressure on Buchi Rota vapour to obtain thick liquid.

Wt.: 2.2 g, % Y-96.9%.

EXAMPLE-37

Preparation of α-naphthylamine salt of (S)-2-Ethoxy-3-(4-{2-[2-methyl-5-(4-methylthiophenyl)pyrrol-1-yl]ethoxy}phenyl)propanoic acid (S)-2-Ethoxy-3-(4-{2-[2-methyl-5-(4-methylthiophenyl)pyrrol-1-yl]ethoxy} phenyl)propanoic acid (3.9 g) was freshly prepared and dissolved in acetonitrile (40 mL) at 25-30° C. To the clear solution α-naphthylamine (1.27 g) was added with stirring and stirred for 2 h at 25-30° C. It was cooled to 0-5° C. and stirred for 20 h, solid was not precipitated. The solvent was distilled out under reduced pressure on Buchi Rota vapour to obtain thick liquid.

Wt.: 4.8 g, % Y-92.8%.

EXAMPLE-38

Preparation of O-phenylenediamine salt of (S)-2-Ethoxy-3-(4-{2-[2-methyl-5-(4-methylthiophenyl)pyrrol-1-yl]-ethoxy}-phenyl)propanoic acid (S)-2-Ethoxy-3-(4-{2-[2-methyl-5-(4-methylthiophenyl)pyrrol-1-yl]ethoxy} phenyl)propanoic acid (3.9 g) was freshly prepared and dissolved in acetonitrile (20 mL) at 25-30° C. To the clear solution O-phenylenediamine (0.970 g) was added with stirring and stirred for 3 h at 25-30° C. It was cooled to 0-5° C. and stirred for 20 h, solid was not precipitated. The solvent was distilled out under reduced pressure on Buchi Rota vapour to obtain thick liquid.

Wt.: 4.6 g, % Y-94.0%.

EXAMPLE-39

Preparation of 1,3-diaminopropane salt of (S)-2-Ethoxy-3-(4-{2-[2-methyl-5-(4-methylthiophenyl)pyrrol-1-yl]-ethoxy}-phenyl)propanoic acid (S)-2-Ethoxy-3-(4-{2-[2-methyl-5-(4-methylthiophenyl)pyrrol-1-yl]ethoxy} phenyl)propanoic acid (1.95 g) was freshly prepared and dissolved in acetonitrile (10 mL) at 25-30° C. To the clear solution 1,3-diaminopropane (0.330 g) was added with stirring and stirred for 1 h at 25-30° C. It was cooled to 0-5° C. and stirred for 1 h, liquid separated. The solvent was distilled out under reduced pressure on Buchi Rota vapour to obtain thick liquid.

Wt.: 1.95 g, % Y-85.1%.

EXAMPLE-40

Preparation of tritylamine salt of (S)-2-Ethoxy-3-(4-{2-[2-methyl-5-(4-methylthiophenyl)pyrrol-1-yl]-ethoxy}-phenyl)propanoic acid (S)-2-Ethoxy-3-(4-{2-[2-methyl-5-(4-methylthiophenyl)pyrrol-1-yl]ethoxy} phenyl)propanoic acid (1.95 g) was freshly prepared and dissolved in ethylacetate (10 mL) at 25-30° C. To the clear solution tritylamine (1.15 g) was added with stirring and stirred for 24 h at 25-30° C., solid did not precipitate. The solvent was distilled out under reduced pressure on Buchi Rota vapour to obtain thick liquid.

Wt.: 3.0 g, % Y-96.7%.

Similarly the following salts of compound of formula (I) with following base were also prepared. Cinchonine, Cinchonidine, (−)-Quinine, Ethylenediamine, Morpholine-4-(2-hydroxyethyl), N,N-Diethyl ethanolamine, Deanol (i.e. N,N-Dimethyl ethanolamine), Hydrabmine, Betaine, Ammonia.

The salts of the invention can be used either for the chemical & chiral purification of the compounds of formula (I) or whenever possible, as pharmaceutically acceptable compounds. When used as pharmaceutically acceptable compounds, the compound of formula (I) is formulated into suitable pharmaceutical formulations using suitable binders and other excipients. Such pharmaceutical compositions may be suitable for the treatment of suitable mammals when such mammals are in need of such treatment. The dosing regimen will be decided based on the therapeutic intervention, the species being treated and the severity of the disease. A skilled person can decide on these based on his knowledge and expertise.

Biological Studies:

Comparative Efficacy Study of (Triglyceride Lowering Effects) of Various Salts of Compound (Ia) in Swiss Albino Mice.

The in-vivo efficacy of compound (I) was evaluated in Swiss albino mice. Anti-dyslipidemic drugs have been reported to lower circulating levels of triglyceride in Swiss albino mice through their effect on genes involved in the peroxisomal fatty acid beta oxidation via PPAR alpha agonism. Therefore, this species is preferred for evaluation of their efficacy in lowering circulating triglyceride (TG) levels.

In this experiment, six to eight week old male Swiss albino mice were issued and kept for acclimatization. Near the end of the acclimatization period, animals judged to be suitable for testing were bled under light ether anesthesia and serum samples were analyzed for Serum triglyceride levels. Animals were selected according to triglyceride levels in the range of 70-180 mg/dl and divided into groups of 6 animals each such that the average TG levels of animals in each group were not significantly different from the others.

Test compound was formulated at specified doses in vehicle (10% Polyethylene glycol (PEG) 400+90% of 0.5% Sodium Carboxy methyl cellulose). The animals were dosed orally, once daily in the morning during six days, starting from next day of grouping with vehicle or test compound. The animals were weighed prior to dosing, and based on these weights; the volume of administration was calculated. The volume of formulation administered to each mouse was 10 ml/kg body weight.

On day 6 one hr after the dose administration, blood (0.25 ml) was collected from retro-orbital sinus of the anaesthetized animals. Serum was separated by centrifugation. Serum was analyzed for triglyceride levels. Analysis for serum triglyceride levels was performed using a Spectrophotometer and commercially available kit. Calculations for determination of % change and % reduction in serum TG levels were performed using MS Excels sheet.

TABLE NO. 2

Treatment groups and dose levels

| Group | Treatment | Dose (mg/kg) | Number of Animals |
|---|---|---|---|
| 1 | Vehicle Control [10% PEG400 + 90% Na-CMC(0.5%)] | 0 mg/kg | 6 |
| 2 | Magnesium salt of formula (I) at 1.0252 mg/kg equivalent to 1 mg/kg of corresponding free acid | 1 mg/kg | 6 |
| 3 | Calcium Salt of Formula (I) at 1.0437 mg/kg equivalent to 1 mg/kg of corresponding free acid | 1 mg/kg | 6 |
| 4 | Sodium Salt of Formula (I) at 1.0498 mg/kg equivalent to 1 mg/kg of corresponding free acid | 1 mg/kg | 6 |
| 5 | Potassium Salt of Formula (I) at 1.0818 mg/kg equivalent to 1 mg/kg of corresponding free acid | 1 mg/kg | 6 |
| 6 | Zinc Salt of Formula (I) at 1.0664 mg/kg equivalent to 1 mg/kg of corresponding free acid | 1 mg/kg | 6 |

TABLE NO. 4

Treatment groups and dose levels

| Group | Treatment | Dose (mg/kg) | Number of Animals |
|---|---|---|---|
| 1 | Vehicle Control [10% PEG400 + 90% Na-CMC(0.5%)] | 0 mg/kg | 6 |
| 2 | Mg salt of formula (I) at 1.0252 mg/kg equivalent to 1 mg/kg of corresponding free acid | 1 mg/kg | 6 |
| 3 | L-arginine salt of Formula (I)) at 1.284 mg/kg equivalent to 1 mg/kg of corresponding free acid | 1 mg/kg | 6 |
| 4 | Tromethamine salt of Formula (I) at 1.2162 mg/kg equivalent to 1 mg/kg of corresponding free acid | 1 mg/kg | 6 |
| 5 | L-lysine salt of Formula (I) at 1.2498 mg/kg equivalent to 1 mg/kg of corresponding free acid | 1 mg/kg | 6 |
| 6 | Piperazine salt of Formula (I) at 1.1638 mg/kg equivalent to 1 mg/kg of corresponding free acid | 1 mg/kg | 6 |
| 7 | Dibenzylamine salt of Formula (I) at 1.3097 mg/kg equivalent to 1 mg/kg of corresponding free acid | 1 mg/kg | 6 |
| 8 | Benethamine salt of Formula (I) at 1.3246 mg/kg equivalent to 1 mg/kg of corresponding free acid | 1 mg/kg | 6 |
| 9 | Benzylamine salt of Formula (I) at 1.196 mg/kg equivalent to 1 mg/kg of corresponding free acid | 1 mg/kg | 6 |

TABLE NO. 3

Effect on triglyceride levels after 6 days of treatment.

| Compound | Serum triglycerides (mg/dl) Day 0 | Serum triglycerides (mg/dl) Day 6 | % Change Day 6 vs Day 0 | % Change Vs control |
|---|---|---|---|---|
| Vehicle Control [10% PEG400 + 90% Na-CMC(0.5%)] | 119.7 ± 10.2 | 118.2 ± 7.8 | 1.4 ± 9.6 | |
| Magnesium salt of formula (I) at 1.0252 mg/kg equivalent to 1 mg/kg of corresponding free acid | 117.7 ± 13.8 | 38.2 ± 4.1 | −66.5 ± 4.1 | −66.1 ± 4.2 |
| Calcium Salt of Formula (I) at 1.0437 mg/kg equivalent to 1 mg/kg of corresponding free acid | 119.2 ± 11.1 | 38.8 ± 3.2 | −66.8 ± 2.5 | −66.4 ± 2.5 |
| Sodium Salt of Formula (I) at 1.0498 mg/kg equivalent to 1 mg/kg of corresponding free acid | 119.4 ± 11.9 | 41.6 ± 1.8 | −63.5 ± 3.6 | −63.1 ± 3.6 |
| Potassium Salt of formula (I) at 1.0818 mg/kg equivalent to 1 mg/kg of corresponding free acid | 119.0 ± 9.2 | 44.8 ± 4.6 | −60.7 ± 6.0 | −60.2 ± 6.0 |
| Zinc Salt of Formula (I) at 1.0664 mg/kg equivalent to 1 mg/kg of corresponding free acid | 119.1 ± 7.6 | 68.6 ± 7.5 | −42.7 ± 4.2 | −42.0 ± 4.2 |

TABLE NO. 5

Effect on triglyceride levels after 6 days of treatment.

| Compound | Serum triglycerides (mg/dl) Day 0 | Serum triglycerides (mg/dl) Day 6 | % Change Day 6 vs Day 0 | % Change Vs control |
|---|---|---|---|---|
| Vehicle Control [10% PEG400 + 90% Na-CMC(0.5%)], po | 91.6 ± 5.0 | 96.8 ± 8.3 | 6.7 ± 9.6 | |
| Mg salt of formula (I) at 1.0252 mg/kg equivalent to 1 mg/kg of corresponding free acid | 91.4 ± 8.8 | 37.4 ± 3.2 | −58.3 ± 3.7 | −60.5 ± 3.5 |
| L-arginine salt of Formula (I) at 1.284 mg/kg equivalent to 1 mg/kg of corresponding free acid | 91.6 ± 7.9 | 37.2 ± 2.1 | −58.0 ± 4.2 | −60.2 ± 3.9 |
| Tromethamine salt of Formula (I) at 1.2162 mg/kg equivalent to 1 mg/kg of corresponding free acid | 91.2 ± 7.8 | 47.9 ± 4.9 | −43.9 ± 9.0 | −46.9 ± 8.5 |
| L-lysine salt of Formula (I) at 1.2498 mg/kg equivalent to 1 mg/kg of corresponding free acid | 91.2 ± 6.8 | 48.7 ± 3.3 | −45.8 ± 3.8 | −48.7 ± 3.6 |
| Piperazine salt of Formula (I) at 1.1638 mg/kg equivalent to 1 mg/kg of corresponding free acid | 91.0 ± 6.5 | 44.1 ± 1.9 | −50.2 ± 4.0 | −52.8 ± 3.7 |
| Dibenzylamine salt of Formula (I) at 1.3097 mg/kg equivalent to 1 mg/kg of corresponding free acid | 91.0 ± 6.7 | 42.1 ± 2.9 | −51.8 ± 6.1 | −54.4 ± 5.8 |
| Benethamine salt of Formula (I) at 1.3246 mg/kg equivalent to 1 mg/kg of corresponding free acid | 91.6 ± 6.4 | 56.0 ± 4.9 | −38.3 ± 5.7 | −41.6 ± 5.4 |
| Benzylamine salt of Formula (I) at 1.196 mg/kg equivalent to 1 mg/kg of corresponding free acid | 91.1 ± 10.8 | 36.5 ± 4.0 | −57.9 ± 6.2 | −60.2 ± 5.8 |

TABLE NO. 6

Treatment groups and dose levels

| Group | Treatment | Dose (mg/kg) | Number of Animals |
|---|---|---|---|
| 1 | Vehicle Control [10% PEG400 + 90% Na-CMC(0.5%)] | 0 mg/kg | 6 |
| 2 | Mg salt of compound of formula (I) at 1.0252 mg/kg, po equivalent to 1 mg/kg of corresponding free acid | 1 mg/kg | 6 |
| 3 | Compound Ia at 1.3075 mg/kg, po equivalent to 1 mg/kg of corresponding free acid | 1 mg/kg | 6 |
| 4 | Triethanolamine salt of Formula (I) at 1.25 mg/kg, po equivalent to 1 mg/kg of corresponding free acid | 1 mg/kg | 6 |
| 5 | Ethanolamine salt of Formula (I) at 1.12 mg/kg, po equivalent to 1 mg/kg of corresponding free acid | 1 mg/kg | 6 |
| 6 | Epolamine salt of Formula (I) at 1.2 mg/kg, po equivalent to 1 mg/kg of corresponding free acid | 1 mg/kg | 6 |
| 7 | Imidazole salt of Formula (I) at 1.13 mg/kg, po equivalent to 1 mg/kg of corresponding free acid | 1 mg/kg | 6 |
| 8 | Choline salt of Formula (I) at 1.22 mg/kg, po equivalent to 1 mg/kg of corresponding free acid | 1 mg/kg | 6 |

TABLE NO. 7

Effect on triglyceride levels after 6 days of treatment

| Compound | Serum triglycerides (mg/dl) Day 0 | Serum triglycerides (mg/dl) Day 6 | % Change Day 6 vs Day 0 | % Change Vs control |
|---|---|---|---|---|
| Vehicle Control [10% PEG400 + 90% Na-CMC(0.5%)] | 111.0 ± 8.0 | 99.6 ± 8.8 | −9.8 ± 5.8 | |

TABLE NO. 7-continued

Effect on triglyceride levels after 6 days of treatment

| Compound | Serum triglycerides (mg/dl) | | % Change Day 6 vs | % Change |
|---|---|---|---|---|
| | Day 0 | Day 6 | Day 0 | Vs control |
| Mg salt of formula (I) at 1.0252 mg/kg, po equivalent to 1 mg/kg of corresponding free acid | 111.1 ± 8.4 | 36.9 ± 2.9 | −65.5 ± 4.2 | −61.5 ± 4.6 |
| Maglumine salt of Formula (I) at 1.3075 mg/kg, po equivalent to 1 mg/kg of corresponding free acid | 110.6 ± 9.1 | 32.4 ± 1.5 | −70.0 ± 2.2 | −66.5 ± 2.5 |
| Triethanolamine salt of Formula (I) at 1.25 mg/kg, po equivalent to 1 mg/kg of corresponding free acid | 110.3 ± 7.5 | 33.0 ± 2.6 | −68.9 ± 3.9 | −65.3 ± 4.4 |
| Ethanolamine salt of Formula (I) at 1.12 mg/kg, po equivalent to 1 mg/kg of corresponding free acid | 110.5 ± 7.5 | 42.5 ± 3.6 | −61.3 ± 3.2 | −56.9 ± 3.6 |
| Epolamine salt of Formula (I) at 1.2 mg/kg, po equivalent to 1 mg/kg of corresponding free acid | 110.5 ± 7.5 | 39.6 ± 3.8 | −64.2 ± 2.3 | −60.1 ± 2.6 |
| Imidazole salt of Formula (I) at 1.13 mg/kg, po equivalent to 1 mg/kg of corresponding free acid | 110.5 ± 7.2 | 43.5 ± 2.5 | −59.8 ± 3.2 | −55.3 ± 3.6 |
| Choline salt of Formula (I) at 1.22 mg/kg, po equivalent to 1 mg/kg of corresponding free acid | 110.9 ± 7.7 | 47.6 ± 3.4 | −56.0 ± 4.3 | −51.0 ± 4.8 |

Efficacy studies of Synergistic Combination Containing Compound of Formula (I) where $M^+$ is $Mg^{+2}$:

I) Antidiabetic Activity of Compound (Ia), Sitagliptin (a Dipeptidyl Peptidase IV Inhibitor) and Co-Administration of Compound (Ia)+Sitagliptin in db/db Mice Model II) Antidiabetic Activity of Compound (Ia), Metformin and Co-Administration of Compound (Ia)+Metformin in db/db mice Model The in-vivo efficacy for antidiabetic activity was done for (I) and (II) individually with db/db mice of 13-14 weeks of age. Generally obese and diabetic animals are insulin resistant and have abnormalities in glucose and lipid metabolism. The development of diabetes and beta cell dysfunction in these animal models closely parallels the pathophysiology of the disease condition in humans. The db/db mouse exhibits an initial phase of hyperinsulinemia, hyperphagia and obesity. They progressively develop into insulinopenia with age, a feature commonly observed in last stage of type-2 diabetes, when blood sugar levels are insufficiently controlled. Therefore, this genetic model proves to be suitable for predicting the likely therapeutic benefit of novel euglycemic agents in human type-2 diabetes.

In this experiment, 48 female db/db mice of 13-14 week were divided into 6 groups and as per their day 0 serum glucose levels per Table no. 8. Vehicle Control group was treated with vehicle (5% Polyethylene glycol (PEG) 400+ 5% Tween 80+90% of 0.5% Sodium Carboxy methyl cellulose) and other five groups with treatment mentioned in Table no. 8. The treatment was given oral gavages once daily for 14 days.

TABLE NO. 8

| Sr. no | Treatment Group | Dosage Level | Sex | Number of Animals |
|---|---|---|---|---|
| 1 | Vehicle Control | 0 mg/kg | Female | 8 |
| 2 | Compound (Ia) | 0.1 mg/kg | Female | 8 |
| 3 | Sitagliptin | 3 mg/kg | Female | 8 |
| 4 | Compound (Ia) (0.1 mg/kg) + Sitagliptin (3 mg/kg) | 0.1 mg/kg + 3 mg/kg | Female | 8 |
| 5 | Metformin | 150 mg/kg | Female | 8 |
| 6 | Compound (Ia) (0.1 mg/kg) + Metformin (150 mg/kg) | 0.1 mg/kg + 150 mg/kg | Female | 8 |

The blood was collected by retro-orbital sinus puncture method under light ether anesthesia on day 0 (pretreatment) and on day 12 for non-fasting glucose analysis and oral glucose tolerance test (OGTT) was performed on day 14 of the treatment in fasting condition. After blood collection serum was separated and analyzed glucose analysis using Spectra max and commercial diagnostic kits. The OGTT procedure followed is as given below—

Oral Glucose Tolerance Test (OGTT):

One day before OGTT all animals were kept on overnight fasting and on the day of OGTT, day 14 of the treatment each animal was dosed with a single dose of vehicle/test compounds administered orally and 60-min post dosing blood was collected (0 min) and glucose load (2 gm/kg/10 ml) administered per orally. Blood was then collected at time points corresponding to 30, 60 and 120 min after glucose load administration. Serum was separated and analyzed for glucose using Spectra max and commercial diagnostic kits.

The calculation for antidiabetic activity i.e. effect on serum glucose and improvement in glucose Area Under Curve (AUC) was calculated using the excel sheet and Graph Pad Prism software. The day 0 and day 12 glucose values of vehicle control and treatment were considered for calculating the effect on serum glucose. The effect on glucose AUC was calculated using the OGTT glucose levels at different time points and the improvement in glucose AUC were the reduction in glucose AUC after the treatment during OGTT.

The effect on serum glucose levels in different treatment groups and % change Vs Vehicle Control is depicted in Table no. 9.

TABLE NO. 9

| Compound | Serum Glucose (mg/dl) Day 0 | Serum Glucose (mg/dl) Day 12 | % Change Day 12 vs Day 0 | % Change Vs control |
|---|---|---|---|---|
| Vehicle control | 406.7 ± 27.1 | 405.7 ± 39.1 | 1.3 ± 9.4 | |
| Compound (Ia)- 0.1 mg/kg, p.o. | 407.8 ± 28.9 | 276.9 ± 39.4 | −33.0 ± 5.9 | −32.8 ± 6.0 |
| Sitagliptin- 3 mg/kg, p.o. | 407.9 ± 34.5 | 485.3 ± 50.5 | 18.3 ± 5.0 | 18.5 ± 5.0 |
| Compound (Ia)- 0.1 mg/kg, p.o.+ Sitagliptin- 3 mg/kg, p.o. | 393.2 ± 27.9 | 161.5 ± 20.1 | −59.1 ± 3.1 | −59.0 ± 3.1 |

The treatment with Compound (Ia) at 0.1 mg/kg showed 32.8% reduction in serum glucose and Sitagliptin (dipeptidyl peptidase IV inhibitor) treatment does not show any reduction rather it has shown slight increase in serum glucose whereas co-administration of Compound (Ia) at 0.1 mg/kg+Sitagliptin (dipeptidyl peptidase IV inhibitor) at 3 mg/kg has shown synergistically 59% reduction in serum glucose.

The effect on glucose area under curve in OGTT in different treatment groups and % change Vs Vehicle Control is depicted in Table no. 10

TABLE NO. 10

| Compounds | AUC Glucose (mg/dl · min) | % improvement in AUC glucose vs control |
|---|---|---|
| Vehicle control | 56845.5 ± 4313.6 | |
| Compound (Ia)- 0.1 mg/kg, p.o. | 51757.3 ± 3366.3 | 9.0 ± 5.9 |
| Sitagliptin- 3 mg/kg, p.o. | 64655.9 ± 6300.6 | −13.7 ± 11.1 |
| Compound (Ia)- 0.1 mg/kg, p.o. + Sitagliptin- 3 mg/kg, p.o. | 38516.4 ± 4515.3 | 32.2 ± 7.9 |

In oral glucose tolerance test, Compound (Ia) at 0.1 mg/kg showed only 9% improvement in glucose area under curve and Sitagliptin treatment does not show any improvement rather it has shown slight increase in glucose intolerance whereas co-administration of Compound (Ia) at 0.1 mg/kg+ Sitagliptin at 3 mg/kg has shown synergistically 32.2% improvement in glucose area under curve during the OGTT done after 14 days of treatment, so it indicates that co-administration of Compound (Ia) and Sitagliptin has shown synergistic activity in both the antidiabetic parameters evaluated i.e. serum glucose and oral glucose tolerance test.

The effect on serum glucose levels in different treatment groups and % change Vs Vehicle Control is depicted in Table no. 11.

TABLE NO. 11

| Compound | Serum Glucose (mg/dl) Day 0 | Serum Glucose (mg/dl) Day 12 | % Change Day 12 vs Day 0 | % Change Vs control |
|---|---|---|---|---|
| Vehicle control | 406.7 ± 27.1 | 405.7 ± 39.1 | 1.3 ± 9.4 | |
| Compound (Ia)- 0.1 mg/kg, p.o. | 407.8 ± 28.9 | 276.9 ± 39.4 | −33.0 ± 5.9 | −32.8 ± 6.0 |
| Compound (Ia)- 0.1 mg/kg, p.o. + Metfomin- 150 mg/kg, p.o. | 405.8 ± 26.9 | 217.5 ± 26.4 | −45.5 ± 4.1 | −45.4 ± 4.4 |

The treatment with Compound (Ia) at 0.1 mg/kg showed 32.8% reduction in serum glucose whereas co-administration of Compound (Ia) at 0.1 mg/kg+Metformin at 150 mg/kg has shown increased 45% reduction in serum glucose. The effect on glucose area under curve in OGTT in different treatment groups and % change Vs Vehicle Control is depicted in Table no. 12

TABLE NO. 12

| Compounds | AUC Glucose (mg/dl · min) | % improvement in AUC glucose vs control |
|---|---|---|
| Vehicle control | 56845.5 ± 4313.6 | |
| Compound (Ia)- 0.1 mg/kg, p.o. | 51757.3 ± 3366.3 | 9.0 ± 5.9 |
| Metfomin- 150 mg/kg, p.o. | 45255.9 ± 4361.1 | 20.4 ± 7.7 |
| Compound (Ia)- 0.1 mg/kg, p.o. + Metformin- 150 mg/kg, p.o. | 28176.3 ± 2548.9 | 50.4 ± 4.5 |

In oral glucose tolerance test, Compound (Ia) at 0.1 mg/kg showed only 9% improvement in glucose area under curve and Metformin at 150 mg/kg showed 20.4% improvement glucose tolerance whereas co-administration of Compound (Ia) at 0.1 mg/kg+Metformin at 150 mg/kg has shown synergistically 50.4% improvement in glucose area under curve during the OGTT done after 14 days of treatment, so it indicates that co-administration of Compound (Ia) and Metformin has shown synergistic activity in the antidiabetic parameters evaluated.

III) Lipid Lowering Effects of Compound (Ia), Rosuvastatin Calcium and Co-Administration of Compound (Ia)+Rosuvastatin Calcium, in Syrian Golden Hamsters The in-vivo efficacy was done in high fat high cholesterol fed Syrian golden hamster. It is an excellent model to investigate hepatic assembly and secretion of lipoprotein since its lipoprotein metabolism closely resembles that of humans as they have cholesteryl ester transfer protein (CETP) as like human. Feeding high fat high cholesterol diet to Syrian golden hamster causes hypercholesterolemia and hypertriglyceridemia which causes an increase in LDL levels and decrease in HDL-C/TC ratio.

In this experiment, 21 Syrian golden hamsters which were kept on high fat-high cholesterol (HF-HC) fructose diet were divided into 3 treatment groups and one group was on normal diet control which was NIN (National Institute of Nutrition, NIN diet) control, the treatment given was as per Table no. 1. NIN control and HF-HC fructose diet vehicle control groups were treated with vehicle (10% Polyethylene glycol (PEG) 400+90% of 0.5% methyl cellulose) and other three groups with treatment mentioned in Table no. 13. The treatment was given oral gavages once daily for 7 days.

TABLE NO. 13

| Sr. no | Treatment Group | Dosage Level | Sex | Number of Animals |
|---|---|---|---|---|
| 1 | NIN control | 0 mg/kg | M | 7 |
| 2 | HF-HC fructose diet vehicle control | 0 mg/kg | M | 7 |
| 3 | Compound (Ia) | 3 mg/kg | M | 7 |
| 4 | Compound (Ia) (3 mg/kg) + Rosuvastatin Calcium (0.3 mg/kg) | 3 mg/kg + 0.3 mg/kg | M | 7 |

The blood was collected by retro-orbital sinus puncture method under light ether anesthesia on day 0 (pretreatment) and on day 7 of the treatment, serum was separated and analyzed for Low density cholesterol (LDL-C) and High density cholesterol (CDL-C) levels using Cobas C 311 clinical chemistry autoanalyser from Roche Diagnostics using commercial diagnostic kits.

Calculations of the % change in LDL-C levels, HDL-C and LDL-C/HDL-C ratio (Vs HF-HC fructose diet control) were performed using MS Excel.

The serum LDL-C levels in different treatment groups and % change Vs HF-HC Fructose Control is depicted in Table no. 14

TABLE NO. 14

| Treatment | Serum LDL-C (mg/dl) Day 0 | Serum LDL-C (mg/dl) Day 7 | LDL-C % Change vs Day 0 | % Change vs HF-HC Fructose Control |
|---|---|---|---|---|
| NIN control | 17.6 ± 1.2 | 15.2 ± 1.2 | −13.6 ± 4.5 | — |
| HF-FC-Fructose control | 111.2 ± 6.6 | 134.8 ± 13.5 | 24.1 ± 15.2 | — |
| Compound (Ia) (3 mg/kg) | 114.8 ± 14.4 | 123.7 ± 15.5 | 9.2 ± 7.8 | −9.9 ± 6.5 |
| Compound (Ia) (3 mg/kg) + Rosuvastatin calcium (0.3 mg/kg) | 115.3 ± 17.5 | 97.9 ± 13.8 | −13.9 ± 3.9 | −29.0 ± 3.2 |

The treatment with Compound (Ia) at 3 mg/kg showed only 9.9% reduction in LDL-C and whereas co-administration of Compound (Ia) (3 mg/kg)+Rosuvastatin calcium (0.3 mg/kg) has shown 29% reduction in LDL-C.

The serum HDL-C levels in different treatment groups and % change Vs HF-HC Fructose Control is depicted in Table no. 15

TABLE NO. 15

| Treatment | Serum HDL-C (mg/dl) Day 0 | Serum HDL-C (mg/dl) Day 7 | HDL-C % Change vs Day 0 | % Change vs HF-HC Fructose Control |
|---|---|---|---|---|
| NIN control | 64.0 ± 3.1 | 64.5 ± 3.8 | 1.1 ± 4.9 | — |
| HF-FC-Fructose control | 101.0 ± 5.6 | 115.2 ± 5.4 | 15.1 ± 5.4 | — |
| Compound (Ia) (3 mg/kg) | 101.8 ± 3.2 | 111.5 ± 4.3 | 9.8 ± 4.5 | −3.7 ± 3.9 |
| Compound (Ia) (3 mg/kg) + Rosuvastatin calcium (0.3 mg/kg) | 101.4 ± 4.5 | 142.8 ± 10.7 | 40.0 ± 5.4 | 22.7 ± 4.7 |

The treatment with Compound (Ia) at 3 mg/kg does not show any increase HDL-C whereas co-administration of Compound (Ia) (3 mg/kg)+Rosuvastatin calcium (0.3 mg/kg) has shown 22.7% increase in HDL-C.

The serum LDL-C/HDL-C ratio, atherogenic index in different treatment groups and % change Vs HF-HC Fructose Control are depicted in Table no. 16

TABLE NO. 16

| Treatment | Serum LDL-C/HDL-C Ratio | | | | | | LDL/HDL % Change Vs Day 0 | | | % Change vs HF-HC Fructose Control | | |
|---|---|---|---|---|---|---|---|---|---|---|---|---|
| | Day 0 | | | Day 7 | | | | | | | | |
| NIN control | 0.28 | ± | 0.0 | 0.24 | ± | 0.0 | −14.3 | ± | 2.8 | — | | |
| HF-FC-Fructose control | 1.11 | ± | 0.0 | 1.16 | ± | 0.1 | 6.3 | ± | 9.4 | — | | |
| Compound (Ia) (3 mg/kg) | 1.13 | ± | 0.1 | 1.09 | ± | 0.1 | −0.3 | ± | 6.7 | −4.9 | ± | 6.4 |
| Compound (Ia) (3 mg/kg) + Rosuvastatin calcium (0.3 mg/kg) | 1.12 | ± | 0.1 | 0.67 | ± | 0.0 | −38.1 | ± | 3.4 | −41.0 | ± | 3.3 |

The treatment with Compound (Ia) at 3 mg/kg showed only 4.9% reduction in LDL-C/HDL-C ratio, atherogenic index whereas co-administration of Compound (Ia) (3 mg/kg) +Rosuvastatin calcium (0.3 mg/kg) has shown synergistically 41.0% reduction in LDL-C/HDL-C ratio, atherogenic index.

In clinical trials, Compound of Formula Ia and Atorvastatin combination showed significantly better reduction in triglyceride and LDL-C levels as compared to placebo group.

Further, no side effects associated with PPARs have been seen.

IV) Antidiabetic Activity of Compound (Ia), Co-Administration of Compound (Ia)+Vildagliptin (Dipeptidyl Peptidase IV Inhibitor) and Co-Administration of Compound (Ia)+Vildagliptin (Dipeptidyl Peptidase IV Inhibitor)+Metformin in db/db Mice Model The in-vivo efficacy for antidiabetic activity was done female db/db mice of 10-15 weeks of age. Generally obese and diabetic animals are insulin resistant and have abnormalities in glucose and lipid metabolism. The development of diabetes and beta cell dysfunction in these animal models closely parallels the pathophysiology of the disease condition in humans. The db/db mouse exhibits an initial phase of hyperinsulinemia, hyperphagia and obesity. They progressively develop into insulinopenia with age, a feature commonly observed in last stage of type-2 diabetes, when blood sugar levels are insufficiently controlled. Therefore, this genetic model proves to be suitable for predicting the likely therapeutic benefit of novel euglycemic agents in human type-2 diabetes.

In this experiment, 28 female db/db mice of 10-15 week were divided into 4 groups and as per their day 0 serum glucose levels per Table no. 1. Vehicle Control group was treated with vehicle (5% Polyethylene glycol (PEG) 400+ 5% Tween 80+90% of 0.5% Sodium Carboxy methyl cellulose) and other four groups with treatment mentioned in Table no. 17. The treatment was given oral gavages once daily for 14 days.

TABLE NO. 17

| Sr. no | Treatment Group | Dosage Level | Sex | Number of Animals |
|---|---|---|---|---|
| 1 | Vehicle Control | 0 mg/kg | Female | 7 |
| 2 | Compound (Ia) | 0.1 mg/kg | Female | 7 |

TABLE NO. 17-continued

| Sr. no | Treatment Group | Dosage Level | Sex | Number of Animals |
|---|---|---|---|---|
| 3 | Compound (Ia) (0.1 mg/kg) + Vildagliptin (1 mg/kg) | 3 mg/kg | Female | 7 |
| 4 | Compound (Ia) (0.1 mg/kg) + Vildagliptin (1 mg/kg) + Metformin (100 mg/kg) | 0.1 mg/kg + 1 mg/kg + 100 mg/kg | Female | 7 |

The blood was collected by retro-orbital sinus puncture method under light ether anesthesia on day 0 (pretreatment) and on day 12 (one hour after dose administration) for non-fasting glucose analysis and oral glucose tolerance test (OGTT) was performed on day 14 of the treatment in fasting condition. After blood collection serum was separated and analyzed glucose analysis using Spectra max and commercial diagnostic kits. The OGTT procedure followed is as given below—

Oral Glucose Tolerance Test (OGTT): One day before OGTT all animals were kept on overnight fasting and on the day of OGTT, day 14 of the treatment each animal was dosed with a single dose of vehicle/test compounds administered orally and 60-min post dosing blood was collected (0 min) and glucose load (2 gm/kg/10 ml) administered per orally. Blood was then collected at time points corresponding to 30, 60 and 120 min after glucose load administration. Serum was separated and analyzed for glucose using Spectra max and commercial diagnostic kits.

The calculation for antidiabetic activity i.e. effect on serum glucose and improvement in glucose Area Under Curve (AUC) was calculated using the excel sheet and Graph Pad Prism software. The day 0 and day 12 glucose values of vehicle control and treatment were considered for calculating the effect on serum glucose. The effect on glucose AUC was calculated using the OGTT glucose levels at different time points and the improvement in glucose AUC were the reduction in glucose AUC after the treatment during OGTT.

The effect on serum glucose levels in different treatment groups and % change Vs Vehicle Control is depicted in Table no. 18

TABLE NO. 18

| Compound | Serum Glucose (mg/dl) | | | | | | % Change Day 12 vs Day 0 | | | % Change Vs control | | |
|---|---|---|---|---|---|---|---|---|---|---|---|---|
| | Day 0 | | | Day 12 | | | | | | | | |
| Vehicle Control | 372.7 | ± | 31.8 | 318.9 | ± | 30.8 | −11.9 | ± | 3.8 | | | |
| Compound Ia (0.1 mg/kg) | 375.4 | ± | 26.8 | 209.0 | ± | 18.1 | −43.8 | ± | 3.9 | −34.3 | ± | 4.5 |
| Compound Ia(0.1 mg/kg, p.o) + Vildagliptin (1 mg/kg, p.o) | 389.1 | ± | 28.0 | 195.2 | ± | 12.6 | −49.0 | ± | 3.8 | −40.4 | ± | 4.4 |
| Compound Ia(0.1 mg/kg, p.o) + Vildagliptin (1 mg/kg, p.o) + Metformin (100 mg/kg) | 365.5 | ± | 35.2 | 146.8 | ± | 7.9 | −57.2 | ± | 5.3 | −49.9 | ± | 6.2 |

The treatment with Compound (Ia) at 0.1 mg/kg showed 34.3% reduction in serum glucose and co-administration of Compound (Ia) at 0.1 mg/kg+Vildagliptin (dipeptidyl peptidase IV inhibitor) at 1 mg/kg has shown 40% reduction in serum glucose whereas co-administration of Compound (Ia) at 0.1mg/kg+Vildagliptin (dipeptidyl peptidase IV inhibitor) at 1 mg/kg+Metformin at 100 mg/kg showed 49.9% reduction in serum glucose.

The effect on glucose area under curve in OGTT in different treatment groups and % change Vs Vehicle Control is depicted in Table no. 19

TABLE NO. 19

| Compounds (mg/kg) | AUC Glucose (mg/dl · min) | | | % improvement in AUC glucose vs control | | |
|---|---|---|---|---|---|---|
| Vehicle Control | 62132.2 | ± | 3749.0 | | | |
| Compound Ia (0.1 mg/kg) | 69613.3 | ± | 2547.9 | −12.0 | ± | 4.1 |
| Compound Ia(0.1 mg/kg, p.o) + Vildagliptin (1 mg/kg, p.o) | 42351.0 | ± | 3087.4 | 31.8 | ± | 5.0 |
| Compound Ia(0.1 mg/kg, p.o) + Vildagliptin (1 mg/kg, p.o) + Metformin (100 mg/kg) | 23963.3 | ± | 2048.7 | 61.4 | ± | 3.3 |

In oral glucose tolerance test, Compound (Ia) at 0.1 mg/kg showed does no show any improvement in glucose area under curve and co-administration of Compound (Ia) at 0.1 mg/kg+Vildagliptin at 1 mg/kg has shown synergistically 31.8% improvement in glucose area under curve (AUC) during the OGTT done after 14 days of treatment, whereas and co-administration of Compound (Ia) at 0.1 mg/kg+Vildagliptin at 1 mg/kg+Metformin at 100 mg/kg has shown synergistically 61.4% improvement in glucose AUC during the OGTT, so it indicates that co-administration of Compound (Ia) and Vildagliptin and metformin has shown synergistic activity antidiabetic parameters evaluated i.e. serum glucose and oral glucose tolerance test.

V) Lipid Lowering Effects of Compound (Ia), and Co-Administration of Compound (Ia)+Atorvastatin, in Syrian Golden Hamsters The in-vivo efficacy was done in high fat high cholesterol fed Syrian golden hamster. It is an excellent model to investigate hepatic assembly and secretion of lipoprotein since its lipoprotein metabolism closely resembles that of humans as they have cholesteryl ester transfer protein (CETP) as like human. Feeding high fat high cholesterol diet to Syrian golden hamster causes hypercholesterolemia and hypertriglyceridemia which causes an increase in LDL levels and decrease in HDL-C/TC ratio.

In this experiment, 18 Syrian golden hamsters which were kept on high fat-high cholesterol (HF-HC) fructose diet were divided into 3 treatment groups and one group was on normal diet control which was NIN (National Institute of Nutrition, NIN diet) control, the treatment given was as per Table no. 1. NIN control and HF-HC fructose diet vehicle control groups were treated with vehicle (5% Polyethylene glycol (PEG) 400+5% Tween 80+90% of 0.5% Sodium Carboxy methyl cellulose) and other three groups with treatment mentioned in Table no. 20. The treatment was given oral gavages once daily for 13 days.

TABLE NO. 20

| Sr. no | Treatment Group | Dosage Level | Sex | Number of Animals |
|---|---|---|---|---|
| 1 | NIN control | 0 mg/kg | M | 6 |
| 2 | HF-HC fructose diet vehicle control | 0 mg/kg | M | 6 |
| 3 | Compound (Ia) | 3 mg/kg | M | 6 |
| 4 | Compound (Ia) (3 mg/kg) + Atorvastatin (0.5 mg/kg) | 3 mg/kg + 0.5 mg/kg | M | 6 |

The blood was collected by retro-orbital sinus puncture method under light ether anesthesia on day 0 (pretreatment) and on day 13 of the treatment, serum was separated and analyzed for Low density cholesterol (LDL-C) and High density cholesterol (CDL-C) and triglyceride levels using Cobas C 311 clinical chemistry autoanalyser from Roche Diagnostics using commercial diagnostic kits.

Calculations of the % change in LDL-C levels, triglyceride and LDL-C/HDL-C ratio (Vs HF-HC fructose diet control) were performed using MS Excel.

The serum LDL-C levels in different treatment groups and % change Vs HF-HC Fructose Control is depicted in Table no. 21

TABLE NO. 21

| Treatment | Serum LDL-C (mg/dl) | | | | | | LDL-C % Change vs Day 0 | | | % Change vs HF-HC Fructose Control | | |
|---|---|---|---|---|---|---|---|---|---|---|---|---|
| | Day 0 | | | Day 13 | | | | | | | | |
| NIN control | 11.3 | ± | 0.6 | 10.7 | ± | 0.7 | −5.5 | ± | 3.9 | | | |
| HF-HC-Fructose control | 74.1 | ± | 4.0 | 87.1 | ± | 10.0 | 16.1 | ± | 8.4 | | | |
| Compound Ia (3 mg/kg) | 75.1 | ± | 6.9 | 73.1 | ± | 4.3 | 0.1 | ± | 7.6 | −14.8 | ± | 6.5 |
| Compound Ia (3 mg/kg) + Atorvastatin 0.5 mg/kg | 79.3 | ± | 5.4 | 55.6 | ± | 5.1 | −28.0 | ± | 9.1 | −38.7 | ± | 7.7 |

The treatment with Compound (Ia) at 3 mg/kg showed only 14.8% reduction in LDL-C whereas co-administration of Compound (Ia) (3 mg/kg)+Atorvastatin (0.5 mg/kg) has shown 38.7% reduction in LDL-C.

The effect on triglyceride in different treatment groups and % change Vs HF-HC Fructose Control is depicted in Table no. 22

TABLE NO. 22

| Treatment | Serum triglyceride (mg/dl) | | | | | | TG % Change vs Day 0 | | | % Change vs HF-HC Fructose Control | | |
|---|---|---|---|---|---|---|---|---|---|---|---|---|
| | Day 0 | | | Day 13 | | | | | | | | |
| NIN control | 117.7 | ± | 6.1 | 153.5 | ± | 15.4 | 30.2 | ± | 9.6 | | | |
| HF-HC-Fructose control | 446.4 | ± | 32.0 | 461.7 | ± | 48.2 | 6.2 | ± | 13.0 | | | |
| Compound Ia (3 mg/kg) | 418.4 | ± | 35.2 | 149.5 | ± | 25.8 | −64.0 | ± | 5.1 | −65.2 | ± | 4.9 |
| Compound Ia (3 mg/kg) + Atorvastatin 0.5 mg/kg | 434.8 | ± | 35.7 | 79.7 | ± | 9.2 | −81.0 | ± | 2.7 | −81.6 | ± | 2.6 |

The treatment with Compound (Ia) at 3 mg/kg showed 65.2% reduction in triglyceride whereas co-administration of Compound (Ia) (3 mg/kg)+Atorvastatin (0.5 mg/kg) has shown 81.6% reduction in triglyceride The serum LDL-C/HDL-C ratio, atherogenic index in different treatment groups and % change Vs HF-HC Fructose Control are depicted in Table no. 23

TABLE NO. 23

| Treatment | LDL/HDL RATIO | | | | | | Change vs Day 0 | | | % Change vs HF-HC Fructose Control | | |
|---|---|---|---|---|---|---|---|---|---|---|---|---|
| | Day 0 | | | Day 13 | | | | | | | | |
| NIN control | 0.19 | ± | 0.0 | 0.15 | ± | 0.0 | −21.9 | ± | 5.4 | | | |
| HF-HC-Fructose control | 0.78 | ± | 0.1 | 0.77 | ± | 0.1 | −2.4 | ± | 4.8 | | | |
| Compound Ia (3 mg/kg) | 0.79 | ± | 0.1 | 0.82 | ± | 0.0 | 6.4 | ± | 7.4 | 8.5 | ± | 7.6 |
| Compound Ia (3 mg/kg) + Atorvastatin 0.5 mg/kg | 0.88 | ± | 0.1 | 0.61 | ± | 0.1 | −26.6 | ± | 11.1 | −25.1 | ± | 11.4 |

The treatment with Compound (Ia) at 3 mg/kg does not showed any reduction in LDL-C/HDL-C ratio, atherogenic index whereas co-administration of Compound (Ia) (3 mg/kg)+Atorvastatin (0.5 mg/kg) has shown synergistically 25.1% reduction in LDL-C/HDL-C ratio, atherogenic index.

Therefore, the compounds of formula (Ia) shows synergistic effect with several other therapeutic agents as described in the specification.

VI) Antidiabetic Activity of Metformin+Insulin and Co-Administration of Compound (Ia)+Metformin+Insulin in db/db Mice Model.

The in-vivo efficacy for antidiabetic activity was done male db/db mice of 12-15 weeks of age. Generally obese and diabetic animals are insulin resistant and have abnormalities in glucose and lipid metabolism. The development of diabetes and beta cell dysfunction in these animal models closely parallels the pathophysiology of the disease condition in humans. The db/db mouse exhibits an initial phase of hyperinsulinemia, hyperphagia and obesity. They progressively develop into insulinopenia with age, a feature commonly observed in last stage of type-2 diabetes, when blood sugar levels are insufficiently controlled. Therefore, this genetic model proves to be suitable for predicting the likely therapeutic benefit of novel euglycemic agents in human type-2 diabetes.

In this experiment, 21 male db/db mice of 12-15 week were divided into 3 groups and as per their day 0 serum glucose levels. Vehicle Control group was treated with vehicle (5% Polyethylene glycol (PEG) 400+5% Tween 80+90% of 0.5% Sodium Carboxy methyl cellulose) and other 2 groups with treatment mentioned in Table no. 24. Compound (Ia) and metformin was administered per orally and insulin was injected subcutaneously as per dose given in table 24, once in day for 14 days.

TABLE NO. 24

| Sr. no | Treatment Group | Dosage Level | Sex | Number of Animals |
|---|---|---|---|---|
| 1 | Vehicle Control | 0 mg/kg | male | 7 |
| 2 | Metformin (100 mg/kg, p.o) + Insulin (0.1 U/Mouse s.c) | 100 mg/kg, per oral + 0.1 U/mouse, s.c. | male | 7 |

TABLE NO. 24-continued

| Sr. no | Treatment Group | Dosage Level | Sex | Number of Animals |
|---|---|---|---|---|
| 3 | Metformin (100 mg/kg, p.o) + Insulin (0.1 U/Mouse s.c) + Compound (Ia) (0.1 mg/kg, p.o.) + | 100 mg/kg, per oral + 0.1 U/mouse, s.c.+ 0.1 mg/kg per oral | male | 7 |

The blood was collected by retro-orbital sinus puncture method under light ether anesthesia on day 0 (pretreatment) and on day 12 (one hour after dose administration) for non-fasting glucose analysis and oral glucose tolerance test (OGTT) was performed on day 14 of the treatment in fasting condition. After blood collection serum was separated and analyzed glucose analysis using Spectra max and commercial diagnostic kits. The OGTT procedure followed is as given below—

Oral Glucose Tolerance Test (OGTT): One day before OGTT all animals were kept on overnight fasting and on the day of OGTT, day 14 of the treatment each animal was dosed with a single dose of vehicle/test compounds administered orally and 60-min post dosing blood was collected (0 min) and glucose load (2 gm/kg/10 ml) administered per orally. Blood was then collected at time points corresponding to 30, 60 and 120 min after glucose load administration. Serum was separated and analyzed for glucose using Spectra max and commercial diagnostic kits.

The calculation for antidiabetic activity i.e. effect on serum glucose and improvement in glucose Area Under Curve (AUC) was calculated using the excel sheet and Graph Pad Prism software. The day 0 and day 12 glucose values of vehicle control and treatment were considered for calculating the effect on serum glucose. The effect on glucose AUC was calculated using the OGTT glucose levels at different time points and the improvement in glucose AUC were the reduction in glucose AUC after the treatment during OGTT.

The effect on serum glucose levels in different treatment groups and % change Vs Vehicle Control is depicted in Table no. 25

TABLE NO. 25

| Compound | Serum Glucose (mg/dl) Day 0 | Serum Glucose (mg/dl) Day 12 | % Change Day 12 vs Day 0 | % Change Vs control |
|---|---|---|---|---|
| Vehicle (p.o) | 523.8 ± 30.2 | 527.5 ± 36.1 | 1.3 ± 6.4 | |
| Metformin (100 mg/kg, p.o) + Insulin (0.1 U/Mouse s.c) | 522.4 ± 32.4 | 212.5 ± 24.0 | −58.1 ± 5.3 | −58.4 ± 5.3 |
| Metformin (100 mg/kg, p.o) + Insulin (0.1 U/mouse, s.c) + Compound Ia (0.1 mg/kg, p.o) | 532.1 ± 35.8 | 126.0 ± 18.3 | −75.4 ± 4.1 | −75.6 ± 4.0 |

The treatment with Metformin+insulin showed 58.4% reduction in serum glucose and co-administration of Compound (Ia) at 0.1mg/kg along with Metformin+insulin has shown 75.6% reduction in serum glucose. In combination Compound (Ia) has caused significant increase in antidiabetic activity of Metformin+insulin.

The effect on glucose area under curve in OGTT in different treatment groups and % change vs Vehicle Control is depicted in Table no. 26

TABLE NO. 26

| | Day 14 | |
|---|---|---|
| Compounds (mg/kg) | AUC Glucose (mg/dl · min) | % improvement in AUC glucose vs control |
| Vehicle (p.o) | 69455.4 ± 3670.6 | |
| Metformin (100 mg/kg, p.o) + Insulin (0.1 U/Mouse s.c) | 30743.6 ± 3689.9 | 55.7 ± 5.3 |
| Metformin (100 mg/kg, p.o) + Insulin (0.1 U/mouse, s.c) + Compound Ia (0.1 mg/kg, p.o) | 27675.3 ± 1984.3 | 60.2 ± 2.9 |

In oral glucose tolerance test, treatment with Metformin+insulin showed 55.7% improvement in glucose area under curve whereas co-administration of Compound (Ia) at 0.1 mg/kg along with Metformin+insulin has shown 60.2% improvement in glucose area under curve (AUC) during the OGTT done after 14 days of treatment. This indicates that co-administration of Compound (Ia) and Metformin+insulin has increased the antidiabetic activity in parameters evaluated i.e. serum glucose and oral glucose tolerance test.

VII) Antidiabetic Activity of Compound (Ia) and Co-Administration of Compound (Ia)+Exenatide (GLP-1 Receptor Agonist) in db/db Mice Model.

VIII) Antidiabetic Activity of Compound (Ia), Co-Administration of Compound (Ia)+Glimepiride (sulfonylurea) in db/db Mice Model.

The in-vivo efficacy for antidiabetic activity was done in male and female db/db mice of 12-16 weeks of age. Generally obese and diabetic animals are insulin resistant and have abnormalities in glucose and lipid metabolism. The development of diabetes and beta cell dysfunction in these animal models closely parallels the pathophysiology of the disease condition in humans. The db/db mouse exhibits an initial phase of hyperinsulinemia, hyperphagia and obesity. They progressively develop into insulinopenia with age, a feature commonly observed in last stage of type-2 diabetes, when blood sugar levels are insufficiently controlled. Therefore, this genetic model proves to be suitable for predicting the likely therapeutic benefit of novel euglycemic agents in human type-2 diabetes.

In this experiment, 49 db/db mice of 12-16 week were divided into 7 groups and as per their day 0 serum glucose levels. Exenatide was administered intraperitoneally (i.p.) after diluting in phosphate buffer saline (PBS) and Compound Ia and glimepiride was administered per orally so there was two vehicle control group one was intraperitoneally (i.p.) PBS for comparing with exenatide i.p. group and another vehicle control group was treated with vehicle used for oral administration (5% Polyethylene glycol (PEG)

400+5% Tween 80+90% of 0.5% Sodium Carboxy methyl cellulose) of Compound Ia and glimepiride. Detail treatments and routes of administrations were mentioned in Table no. 27. The treatment was given once daily for 7 days.

TABLE NO. 27

| Sr. no | Treatment Group | Dosage Level and route of administration | Number of Animals |
|---|---|---|---|
| 1 | Vehicle Control for I.P, ((PBS-10 ml/kg, i.p) | 0 mg/kg | 3 female + 4 Male = 7 |

TABLE NO. 27-continued

| Sr. no | Treatment Group | Dosage Level and route of administration | Number of Animals |
|---|---|---|---|
| 2 | Exenatide (0. 1 μg/kg, i.p) | 0.1 μg/kg, i.p | 3 female + 4 Male = 7 |
| 3 | Vehicle Control for per oral (10 ml/kg, p.o) | 0 mg/kg, p.o. | 3 female + 4 Male = 7 |
| 4 | Compound Ia (0.1 mg/kg. p.o.) | 0.1 mg/kg. p.o. | 4 female + 3 Male = 7 |
| 5 | Glimepiride (2 mg/kg, p.o.) | 2 mg/kg, p.o. | 3 female + 4 Male = 7 |
| 6 | Compound Ia (0.1 mg/kg, p.o) + Exenatide (0.1 μg/kg, i.p) | 0.1 mg/kg. p.o. + 0.1 μg/kg, i.p | 3 female + 4 Male = 7 |
| 7 | Compound Ia (0.1 mg/kg, p.o) + Glimepiride (2 mg/kg, p.o) | 0.1 mg/kg. p.o.+ 2 mg/kg, p.o. | 3 female + 4 Male = 7 |

The blood was collected by retro-orbital sinus puncture method under light ether anesthesia on day 0 (pretreatment) and on day 6 (one hour after dose administration) for non-fasting glucose analysis and oral glucose tolerance test (OGTT) was performed on day 7 of the treatment in fasting condition. After blood collection serum was separated and analyzed glucose analysis using Spectra max and commercial diagnostic kits. The OGTT procedure followed is as given below—

Oral Glucose Tolerance Test (OGTT): One day before OGTT all animals were kept on overnight fasting and on the day of OGTT, day 7 of the treatment each animal was dosed with a single dose of vehicle/test compounds administered orally and 60-min post dosing blood was collected (0 min) and glucose load (2 gm/kg/10 ml) administered per orally. Blood was then collected at time points corresponding to 30, 60 and 120 min after glucose load administration. Serum was separated and analyzed for glucose using Spectra max and commercial diagnostic kits.

The calculation for antidiabetic activity i.e. effect on serum glucose and improvement in glucose Area Under Curve (AUC) was calculated using the excel sheet and Graph Pad Prism software. The day-0 and day-6 glucose values of vehicle control and treatment were considered for calculating the effect on serum glucose. The effect on glucose AUC was calculated using the OGTT glucose levels at different time points and the improvement in glucose AUC were the reduction in glucose AUC after the treatment during OGTT.

The effect on serum glucose levels after treatment with Exenatide and its combination on day 6 in various groups and % change Vs Vehicle Control is depicted in Table no. 28

TABLE NO. 28

| Compound | Serum Glucose (mg/dl) | | | | | % Change Day 6 vs Day 0 | | | % Change Vs control | | |
|---|---|---|---|---|---|---|---|---|---|---|---|
| | Day 0 | | | Day 6 | | | | | | | |
| Vehicle for I.p. (PBS-10 ml/kg, i.p) | 415.7 | ± | 24.7 | 457.8 | ± | 40.5 | 13.7 | ± | 14.5 | | |
| Exenatide (0.1 μg/kg, i.p) | 408.4 | ± | 23.2 | 317.3 | ± | 25.0 | −22.2 | ± | 4.6 | −29.3 ± 4.2 |
| Vehicle for per oral (10 ml/kg, p.o) | 405.1 | ± | 23.1 | 466.6 | ± | 30.9 | 15.0 | ± | 2.8 | | |
| Compound Ia (0.1 mg/kg, p.o) | 420.6 | ± | 25.1 | 363.4 | ± | 39.0 | −13.4 | ± | 8.1 | −24.8 ± 7.0 |
| Compound Ia (0.1 mg/kg, p.o) + Exenatide (0.1 μg/kg, i.p) | 402.5 | ± | 22.6 | 224.0 | ± | 28.9 | −43.0 | ± | 6.1 | −50.5 ± 5.3 |

The treatment with Compound Ia (0.1 mg/kg, p.o.) and Exenatide (0.1 μg/kg, i.p.) showed 24.8 and 29.3% reduction in serum glucose whereas co-administration of Compound (Ia) at 0.1mg/kg +Exenatide (GLP-1 receptor agonist) at 0.1 μg/kg has shown 50.5% reduction in serum glucose.

The effect on glucose area under curve in OGTT after treatment with Exenatide and its combination and % change Vs Vehicle Control is depicted in Table no. 29

TABLE NO. 29

| Compounds (mg/kg) | AUC Glucose (mg/dl · min) | | | % improvement in AUC glucose vs control | | |
|---|---|---|---|---|---|---|
| Vehicle for I.p. (PBS-10 ml/kg, i.p) | 50202.8 | ± | 3020.2 | | | |
| Exenatide (0.1 μg/kg, i.p) | 40025.6 | ± | 4392.0 | 20.3 | ± | 8.7 |
| Vehicle for per oral (10 ml/kg, p.o) | 60917.9 | ± | 3892.3 | | | |
| Compound Ia (0.1 mg/kg, p.o) | 46452.6 | ± | 4298.1 | 23.7 | ± | 7.1 |
| Compound Ia (0.1 mg/kg, p.o) + Exenatide (0.1 μg/kg, i.p) | 33143.7 | ± | 4591.8 | 45.6 | ± | 7.5 |

In oral glucose tolerance test, treatment with Compound Ia (0.1 mg/kg, p.o.) and Exenatide (0.1 μg/kg, i.p.) showed 23.7 and 20.3% improvement in glucose area under curve (AUC) whereas co-administration of Compound (Ia) at 0.1mg/kg+Exenatide (GLP-1 receptor agonist) at 0.1 μg/kg has shown 45.6% improvement in glucose AUC during the OGTT.

This indicates that co-administration of Compound (Ia) and Exenatide (GLP-1 receptor agonist) has shown synergistic activity in antidiabetic parameters evaluated i.e. serum glucose and oral glucose tolerance test.

The effect on serum glucose levels after treatment with Glimepiride and its combination on day 6 in various groups and % change Vs Vehicle Control is depicted in Table no. 30

TABLE NO. 30

| Compound | Serum Glucose (mg/dl) | | | | % Change | | | % Change | | |
| --- | --- | --- | --- | --- | --- | --- | --- | --- | --- | --- |
| | Day 0 | | | Day 6 | | Day 6 vs Day 0 | | Vs control | | |
| Vehicle Control (10 ml/kg, p.o) | 405.1 | ± | 23.1 | 466.6 | ± 30.9 | 15.0 | ± 2.8 | | | |
| Compound Ia (0.1 mg/kg, p.o) | 420.6 | ± | 25.1 | 363.4 | ± 39.0 | −13.4 | ± 8.1 | −24.8 | ± | 7.0 |
| Glimepiride (2 mg/kg, p.o) | 402.0 | ± | 25.8 | 506.7 | ± 34.8 | 26.9 | ± 7.3 | 10.1 | ± | 6.4 |
| Compound Ia (0.1 mg/kg, p.o) + Glimepiride (2 mg/kg, po) | 357.3 | ± | 33.9 | 247.0 | ± 40.0 | −32.6 | ± 12.6 | −41.4 | ± | 10.9 |

The treatment with Compound Ia (0.1 mg/kg, p.o.) showed 24.8% reduction in serum glucose but glimepiride (2 mg/kg, p.o.) showed 10.1% increase in serum glucose as compared to vehicle control. Whereas co-administration of Compound (Ia) at 0.1 mg/kg+glimepiride (sulfonylurea) at 2 mg/kg, p.o. has shown synergistically 41.4% reduction in serum glucose.

The effect on glucose area under curve (AUC) in OGTT after treatment with Glimepiride and its combination in different treatment groups and % change Vs Vehicle Control is depicted in Table no. 31

TABLE NO. 31

| Compounds (mg/kg) | AUC Glucose (mg/dl · min) | | | % improvement in AUC glucose vs control | | |
| --- | --- | --- | --- | --- | --- | --- |
| Vehicle for per oral (10 ml/kg, p.o) | 60917.9 | ± | 3892.3 | | | |
| Compound Ia (0.1 mg/kg, p.o) | 46452.6 | ± | 4298.1 | 23.7 | ± | 7.1 |
| Glimepiride (2 mg/kg, p.o) | 62529.0 | ± | 3008.2 | −2.6 | ± | 4.9 |
| Compound Ia (0.1 mg/kg, p.o) + Glimepiride (2 mg/kg, po) | 45079.3 | ± | 5367.3 | 26.0 | ± | 8.8 |

In oral glucose tolerance test, Compound (Ia) at 0.1 mg/kg showed 23.7% improvement in glucose area under curve and glimepiride (2 mg/kg, p.o.) does not any improvement in glucose AUC. Whereas co-administration of Compound (Ia) at 0.1 mg/kg+glimepiride (2 mg/kg, p.o.) has shown synergistically 26% improvement in glucose area under curve (AUC) during the OGTT done after 7 days of treatment.

This indicates that co-administration of Compound (Ia) and glimepiride (sulfonylurea) has shown synergistic activity in antidiabetic parameters evaluated i.e. serum glucose and oral glucose tolerance test.

We claim:

1. A compound selected from the group consisting of:
   (i) Benethamine crystalline salt of (S) 2-Ethoxy-3-(4-{2-[2-methyl-5-(4-methylthiophenyl)-pyrrol-1-yl]-ethoxy}-phenyl)-propionic acid having an XRD pattern having a peak at 2 theta values of ±0.2 degree at about 10.0, 10.3, 14.5, 15.1, 15.7, 16.7, 17.4, 17.9, 18.6, 19.2, 19.8, 21.3, 23.2 and 25.7 degrees;
   (ii) Benzylamine crystalline salt of (S) 2-Ethoxy-3-(4-{2-[2-methyl-5-(4-methylthiophenyl)-pyrrol-1-yl]-ethoxy}-phenyl)-propionic acid having an XRD pattern having a peak at 2 theta values at about 14.8, 16.8, 17.5, 18.3, 19.3, 20.8, 22.6 and 24.2 ±0.2 degrees;
   (iii) Dibenzylamine crystalline salt of (S) 2-Ethoxy-3-(4-{2-[2-methyl-5-(4-methylthiophenyl)-pyrrol-1-yl]-ethoxy}-phenyl)-propionic acid having a peak at 2 theta values at about 8.72, 16.8, 18.5, 19.1, 19.6, 20.6, 21.6, 22.5 and 24.5 ±0.2 degrees; and
   (iv) Imidazole crystalline salt of (S) 2-Ethoxy-3-(4-{2-[2-methyl-5-(4-methylthiophenyl)-pyrrol-1-yl]-ethoxy}-phenyl)-propionic acid having an XRD pattern having a peak at 2 theta values at about 9.40, 14.7, 15.6, 17.3, 21.0, 21.5, 22.5 and 26.2 ±0.2 degrees.

2. The compound of claim 1, wherein the compound is a benethamine crystalline salt of (S) 2-Ethoxy-3-(4-{2-[2-methyl-5-(4-methylthiophenyl)-pyrrol-1-yl]-ethoxy}-phenyl)-propionic acid having an XRD pattern having a peak at 2 theta values of ±0.2 degree at about 10.0, 10.3, 14.5, 15.1, 15.7, 16.7, 17.4, 17.9, 18.6, 19.2, 19.8, 21.3, 23.2 and 25.7 degrees.

3. The compound of claim 1, wherein the compound is a benzylamine crystalline salt of (S) 2-Ethoxy-3-(4-{2-[2-methyl-5-(4-methylthiophenyl)-pyrrol-1-yl]-ethoxy}-phenyl)-propionic acid having an XRD pattern having a peak at 2 theta values at about 14.8, 16.8, 17.5, 18.3, 19.3, 20.8, 22.6 and 24.2±0.2 degrees.

4. The compound of claim 1, wherein the compound is a dibenzylamine crystalline salt of (S) 2-Ethoxy-3-(4-{2-[2-methyl-5-(4-methylthiophenyl)-pyrrol-1-yl]-ethoxy}-phenyl)-propionic acid having an XRD pattern having a peak at 2 theta values of about 8.72, 16.8, 18.5, 19.1, 19.6, 20.6, 21.6, 22.5 and 24.5±0.2 degrees.

5. The compound of claim 1, wherein the compound is a imidazole crystalline salt of (S) 2-Ethoxy-3-(4-{2-[2-methyl-5-(4-methylthiophenyl)-pyrrol-1-yl]-ethoxy}-phenyl)-propionic acid having an XRD pattern having a peak at 2 theta values of about 9.40, 14.7, 15.6, 17.3, 21.0, 21.5, 22.5 and 26.2±0.2 degrees.

6. The compound of claim 1, wherein the compound is a benethamine crystalline salt of (S) 2-Ethoxy-3-(4-{2-[2-methyl-5-(4-methylthiophenyl)-pyrrol-1-yl]-ethoxy}-phenyl)-propionic acid having a powder X-ray diffraction pattern substantially as depicted in FIG. 10.

7. The compound of claim 1, wherein the compound is a benzylamine crystalline salt of (S) 2-Ethoxy-3-(4-{2-[2-methyl-5-(4-methylthiophenyl)-pyrrol-1-yl]-ethoxy}-phenyl)-propionic acid having a powder X-ray diffraction pattern substantially as depicted in FIG. 11.

8. The compound of claim 1, wherein the compound is a dibenzylamine crystalline salt of (S) 2-Ethoxy-3-(4-{2-[2-methyl-5-(4-methylthiophenyl)-pyrrol-1-yl]-ethoxy}-phenyl)-propionic acid having a powder X-ray diffraction pattern substantially as depicted in FIG. 12.

9. The compound of claim 1, wherein the compound is a imidazole crystalline salt of (S) 2-Ethoxy-3-(4-{2-[2-methyl-5-(4-methylthiophenyl)-pyrrol-1-yl]-ethoxy}-phenyl)-propionic acid having a powder X-ray diffraction pattern substantially as depicted in FIG. 14.

10. A compound selected from the group consisting of:
    (i) (S)-α-4-Methylphenylethylamine salt of (S) 2-Ethoxy-3-(4-{2-[2-methyl-5-(4-methylthiophenyl)-pyrrol-1-yl]-ethoxy}-phenyl)-propionic acid;

(ii) (S)-α-3-Methoxyphenylethylamine salt of (S) 2-Ethoxy-3-(4-{2-[2-methyl-5-(4-methylthiophenyl)-pyrrol-1-yl]-ethoxy}-phenyl)-propionic acid;
(iii) (S)-α-4-Methoxyphenylethylamine salt of (S) 2-Ethoxy-3-(4-{2-[2-methyl-5-(4-methylthiophenyl)-pyrrol-1-yl]-ethoxy}-phenyl)-propionic acid;
(iv) (S)-α-4-Chlorophenylethylamine salt of (S) 2-Ethoxy-3-(4-{2-[2-methyl-5-(4-methylthiophenyl)-pyrrol-1-yl]-ethoxy}-phenyl)-propionic acid; and
(v) (S)-α-Naphthylethylamine salt of (S) 2-Ethoxy-3-(4-{2-[2-methyl-5-(4-methylthiophenyl)-pyrrol-1-yl]-ethoxy}-phenyl)-propionic acid.

11. A compound in amorphous form selected from:
(i) Zinc salt of (S) 2-Ethoxy-3-(4-{2-[2-methyl-5-(4-methylthiophenyl)-pyrrol-1-yl]-ethoxy}-phenyl)-propionic acid;
ii) Lithium salt of (S) 2-Ethoxy-3-(4-{2-[2-methyl-5-(4-methylthiophenyl)-pyrrol-1-yl]-ethoxy}-phenyl)-propionic acid;
(iii) Piperazine salt of (S) 2-Ethoxy-3-(4-{2-[2-methyl-5-(4-methylthiophenyl)-pyrrol-1-yl]-ethoxy}-phenyl)-propionic acid;
(iv) Tromethamine salt of (S) 2-Ethoxy-3-(4-{2-[2-methyl-5-(4-methylthiophenyl)-pyrrol-1-yl]-ethoxy}-phenyl)-propionic acid;
(v) L-Lysine salt of (S) 2-Ethoxy-3-(4-{2-[2-methyl-5-(4-methylthiophenyl)-pyrrol-1-yl]-ethoxy}-phenyl)-propionic acid;
(vi) Meglumine salt (S) 2-Ethoxy-3-(4-{2-[2-methyl-5-(4-methylthiophenyl)-pyrrol-1-yl]-ethoxy}-phenyl)-propionic acid;
(vii) Benethamine salt of (S) 2-Ethoxy-3-(4-{2-[2-methyl-5-(4-methylthiophenyl)-pyrrol-1-yl]-ethoxy}-phenyl)-propionic acid;
(viii) Benzylamine salt of (S) 2-Ethoxy-3-(4-{2-[2-methyl-5-(4-methylthiophenyl)-pyrrol-1-yl]-ethoxy}-phenyl)-propionic acid;
(ix) Dibenzylamine salt of (S) 2-Ethoxy-3-(4-{2-[2-methyl-5-(4-methylthiophenyl)-pyrrol-1-yl]-ethoxy}-phenyl)-propionic acid;
(x) Arginine salt of (S) 2-Ethoxy-3-(4-{2-[2-methyl-5-(4-methylthiophenyl)-pyrrol-1-yl]-ethoxy}-phenyl)-propionic acid;
(xi) Imidazole salt of (S) 2-Ethoxy-3-(4-{2-[2-methyl-5-(4-methylthiophenyl)-pyrrol-1-yl]-ethoxy}-phenyl)-propionic acid;
(xii) Dicyclohexylamine salt of (S) 2-Ethoxy-3-(4-{2-[2-methyl-5-(4-methylthiophenyl)-pyrrol-1-yl]-ethoxy}-phenyl)-propionic acid;
(xiii) Diethylamine salt of (S) 2-Ethoxy-3-(4-{2-[2-methyl-5-(4-methylthiophenyl)-pyrrol-1-yl]-ethoxy}-phenyl)-propionic acid;
(xiv) Diphenylamine salt of (S) 2-Ethoxy-3-(4-{2-[2-methyl-5-(4-methylthiophenyl)-pyrrol-1-yl]-ethoxy}-phenyl)-propionic acid;
(xv) α-Naphthylamine salt of (S) 2-Ethoxy-3-(4-{2-[2-methyl-5-(4-methylthiophenyl)-pyrrol-1-yl]-ethoxy}-phenyl)-propionic acid;
(xvi) O-phenylenediamine salt of (S) 2-Ethoxy-3-(4-{2-[2-methyl-5-(4-methylthiophenyl)-pyrrol-1-yl]-ethoxy}-phenyl)-propionic acid;
(xvii) 1,3-Diaminopropane salt of (S) 2-Ethoxy-3-(4-{2-[2-methyl-5-(4-methylthiophenyl)-pyrrol-1-yl]-ethoxy}-phenyl)-propionic acid;
(xviii) (S)-α-Naphthylethylamine salt of (S) 2-Ethoxy-3-(4-{2-[2-methyl-5-(4-methylthiophenyl)-pyrrol-1-yl]-ethoxy}-phenyl)-propionic acid;
(xix) (S)-3-Methoxyphenylethylamine salt of (S) 2-Ethoxy-3-(4-{2-[2-methyl-5-(4-methylthiophenyl)-pyrrol-1-yl]-ethoxy}-phenyl)-propionic acid;
(xx) (S)-4-Methoxyphenylethylamine salt of (S) 2-Ethoxy-3-(4-{2-[2-methyl-5-(4-methylthiophenyl)-pyrrol-1-yl]-ethoxy}-phenyl)-propionic acid;
(xxi) (S)-4-Chlorophenylethylamine salt of (S) 2-Ethoxy-3-(4-{2-[2-methyl-5-(4-methylthiophenyl)-pyrrol-1-yl]-ethoxy}-phenyl)-propionic acid;
(xxii) (S)-4-Methylphenylethylamine salt of (S) 2-Ethoxy-3-(4-{2-[2-methyl-5-(4-methylthiophenyl)-pyrrol-1-yl]-ethoxy}-phenyl)-propionic acid;
(xxiii) Cinchonine salt of (S) 2-Ethoxy-3-(4-{2-[2-methyl-5-(4-methylthiophenyl)-pyrrol-1-yl]-ethoxy}-phenyl)-propionic acid;
(xxiv) Cinchonidine salt of (S) 2-Ethoxy-3-(4-{2-[2-methyl-5-(4-methylthiophenyl)-pyrrol-1-yl]-ethoxy}-phenyl)-propionic acid;
(xxv) (-)-Quinine salt of (S) 2-Ethoxy-3-(4-{2-[2-methyl-5-(4-methylthiophenyl)-pyrrol-1-yl]-ethoxy}-phenyl)-propionic acid;
(xxvi) Benzathine salt (S) 2-Ethoxy-3-(4-{2-[2-methyl-5-(4-methylthiophenyl)-pyrrol-1-yl]-ethoxy}-phenyl)-propionic acid;
(xxvii) Ethanolamine salt of (S) 2-Ethoxy-3-(4-{2-[2-methyl-5-(4-methylthiophenyl)-pyrrol-1-yl]-ethoxy}-phenyl)-propionic acid;
(xxviii) Diethanolamine salt of (S) 2-Ethoxy-3-(4-{2-[2-methyl-5-(4-methylthiophenyl)-pyrrol-1-yl]-ethoxy}-phenyl)-propionic acid;
(xxix) Triethanolamine salt of (S) 2-Ethoxy-3-(4-{2-[2-methyl-5-(4-methylthiophenyl)-pyrrol-1-yl]-ethoxy}-phenyl)-propionic acid;
(xxx) Ethylenediamine salt of (S) 2-Ethoxy-3-(4-{2-[2-methyl-5-(4-methylthiophenyl)-pyrrol-1-yl]-ethoxy}-phenyl)-propionic acid;
(xxxi) Choline salt of (S) 2-Ethoxy-3-(4-{2-[2-methyl-5-(4-methylthiophenyl)-pyrrol-1-yl]-ethoxy}-phenyl)-propionic acid;
(xxxii) Epolamine salt of (S) 2-Ethoxy-3-(4-{2-[2-methyl-5-(4-methylthiophenyl)-pyrrol-1-yl]-ethoxy}-phenyl)-propionic acid;
(xxxiii) Morpholine 4-(2-hydroxyethyl) salt of (S) 2-Ethoxy-3-(4-{2-[2-methyl-5-(4-methylthiophenyl)-pyrrol-1-yl]-ethoxy}-phenyl)-propionic acid;
(xxxiv) N,N-Diethylethanolamine salt of (S) 2-Ethoxy-3-(4-{2-[2-methyl-5-(4-methylthiophenyl)-pyrrol-1-yl]-ethoxy}-phenyl)-propionic acid;
(xxxv) Deanol salt of (S) 2-Ethoxy-3-(4-{2-[2-methyl-5-(4-methylthiophenyl)-pyrrol-1-yl]-ethoxy}-phenyl)-propionic acid;
(xxxvi) Hydrabamine salt of (S) 2-Ethoxy-3-(4-{2-[2-methyl-5-(4-methylthiophenyl)-pyrrol-1-yl]-ethoxy}-phenyl)-propionic acid;
(xxxvii) Betaine salt of (S) 2-Ethoxy-3-(4-{2-[2-methyl-5-(4-methylthiophenyl)-pyrrol-1-yl]-ethoxy}-phenyl)-propionic acid;
(xxxviii) Ammonia salt of (S) 2-Ethoxy-3-(4-{2-[2-methyl-5-(4-methylthiophenyl)-pyrrol-1-yl]-ethoxy}-phenyl)-propionic acid;
(xxxix) Adamantanamine salt of (S) 2-Ethoxy-3-(4-{2-[2-methyl-5-(4-methylthiophenyl)-pyrrol-1-yl]-ethoxy}-phenyl)-propionic acid;
(xl) 1-Adamantanmethylamine salt of (S) 2-Ethoxy-3-(4-{2-[2-methyl-5-(4-methylthiophenyl)-pyrrol-1-yl]-ethoxy}-phenyl)-propionic acid;

(xli) Tritylamine salt of (S) 2-Ethoxy-3-(4-{2-[2-methyl-5-(4-methylthiophenyl)-pyrrol-1-yl]-ethoxy}-phenyl)-propionic acid; and (xlii) Pyrrolidine salt of (S) 2-Ethoxy-3-(4-{2-[2-methyl-5-(4-methylthiophenyl)-pyrrol-1-yl]-ethoxy}-phenyl)-propionic acid.

12. A compound selected from the following, wherein the compound is a mixture of crystalline and amorphous forms:

(i) Zinc salt of (S) 2-Ethoxy-3-(4-{2-[2-methyl-5-(4-methylthiophenyl)-pyrrol-1-yl]-ethoxy}-phenyl)-propionic acid;

ii) Lithium salt of (S) 2-Ethoxy-3-(4-{2-[2-methyl-5-(4-methylthiophenyl)-pyrrol-1-yl]-ethoxy}-phenyl)-propionic acid;

(iii) Piperazine salt of (S) 2-Ethoxy-3-(4-{2-[2-methyl-5-(4-methylthiophenyl)-pyrrol-1-yl]-ethoxy}-phenyl)-propionic acid;

(iv) Tromethamine salt of (S) 2-Ethoxy-3-(4-{2-[2-methyl-5-(4-methylthiophenyl)-pyrrol-1-yl]-ethoxy}-phenyl)-propionic acid;

(v) L-Lysine salt of (S) 2-Ethoxy-3-(4-{2-[2-methyl-5-(4-methylthiophenyl)-pyrrol-1-yl]-ethoxy}-phenyl)-propionic acid;

(vi) Meglumine salt of (S) 2-Ethoxy-3-(4-{2-[2-methyl-5-(4-methylthiophenyl)-pyrrol-1-yl]-ethoxy}-phenyl)-propionic acid;

(vii) Benethamine salt of (S) 2-Ethoxy-3-(4-{2-[2-methyl-5-(4-methylthiophenyl)-pyrrol-1-yl]-ethoxy}-phenyl)-propionic acid;

(viii) Benzylamine salt of (S) 2-Ethoxy-3-(4-{2-[2-methyl-5-(4-methylthiophenyl)-pyrrol-1-yl]-ethoxy}-phenyl)-propionic acid;

(ix) Dibenzylamine salt of (S) 2-Ethoxy-3-(4-{2-[2-methyl-5-(4-methylthiophenyl)-pyrrol-1-yl]-ethoxy}-phenyl)-propionic acid;

(x) Arginine salt of (S) 2-Ethoxy-3-(4-{2-[2-methyl-5-(4-methylthiophenyl)-pyrrol-1-yl]-ethoxy}-phenyl)-propionic acid;

(xi) Imidazole salt of (S) 2-Ethoxy-3-(4-{2-[2-methyl-5-(4-methylthiophenyl)-pyrrol-1-yl]-ethoxy}-phenyl)-propionic acid;

(xii) Dicyclohexylamine salt of (S) 2-Ethoxy-3-(4-{2-[2-methyl-5-(4-methylthiophenyl)-pyrrol-1-yl]-ethoxy}-phenyl)-propionic acid;

(xiii) Diethylamine salt of (S) 2-Ethoxy-3-(4-{2-[2-methyl-5-(4-methylthiophenyl)-pyrrol-1-yl]-ethoxy}-phenyl)-propionic acid;

(xiv) Diphenylamine salt of (S) 2-Ethoxy-3-(4-{2-[2-methyl-5-(4-methylthiophenyl)-pyrrol-1-yl]-ethoxy}-phenyl)-propionic acid;

(xv) α-Naphthylamine salt of (S) 2-Ethoxy-3-(4-{2-[2-methyl-5-(4-methylthiophenyl)-pyrrol-1-yl]-ethoxy}-phenyl)-propionic acid;

(xvi) O-phenylenediamine salt of (S) 2-Ethoxy-3-(4-{2-[2-methyl-5-(4-methylthiophenyl)-pyrrol-1-yl]-ethoxy}-phenyl)-propionic acid;

(xvii) 1,3-Diaminopropane salt of (S) 2-Ethoxy-3-(4-{2-[2-methyl-5-(4-methylthiophenyl)-pyrrol-1-yl]-ethoxy}-phenyl)-propionic acid;

(xviii) (S)-α-Naphthylethylamine salt of (S) 2-Ethoxy-3-(4-{2-[2-methyl-5-(4-methylthiophenyl)-pyrrol-1-yl]-ethoxy}-phenyl)-propionic acid;

(xix) (S)-3-Methoxyphenylethylamine salt of (S) 2-Ethoxy-3-(4-{2-[2-methyl-5-(4-methylthiophenyl)-pyrrol-1-yl]-ethoxy}-phenyl)-propionic acid;

(xx) (S)-4-Methoxyphenylethylamine salt of (S) 2-Ethoxy-3-(4-{2-[2-methyl-5-(4-methylthiophenyl)-pyrrol-1-yl]-ethoxy}-phenyl)-propionic acid;

(xxi) (S)-4-Chlorophenylethylamine salt of (S) 2-Ethoxy-3-(4-{2-[2-methyl-5-(4-methylthiophenyl)-pyrrol-1-yl]-ethoxy}-phenyl)-propionic acid;

(xxii) (S)-4-Methoxyphenylethylamine salt of (S) 2-Ethoxy-3-(4-{2-[2-methyl-5-(4-methylthiophenyl)-pyrrol-1-yl]-ethoxy}-phenyl)-propionic acid;

(xxiii) Cinchonine salt of (S) 2-Ethoxy-3-(4-{2-[2-methyl-5-(4-methylthiophenyl)-pyrrol-1-yl]-ethoxy}-phenyl)-propionic acid;

(xxiv) Cinchonidine salt of (S) 2-Ethoxy-3-(4-{2-[2-methyl-5-(4-methylthiophenyl)-pyrrol-1-yl]-ethoxy}-phenyl)-propionic acid;

(xxv) (-)-Quinine salt of (S) 2-Ethoxy-3-(4-{2-[2-methyl-5-(4-methylthiophenyl)-pyrrol-1-yl]-ethoxy}-phenyl)-propionic acid;

(xxvi) Benzathine salt of (S) 2-Ethoxy-3-(4-{2-[2-methyl-5-(4-methylthiophenyl)-pyrrol-1-yl]-ethoxy}-phenyl)-propionic acid;

(xxvii) Ethanolamine salt of (S) 2-Ethoxy-3-(4-{2-[2-methyl-5-(4-methylthiophenyl)-pyrrol-1-yl]-ethoxy}-phenyl)-propionic acid;

(xxviii) Diethanolamine salt of (S) 2-Ethoxy-3-(4-{2-[2-methyl-5-(4-methylthiophenyl)-pyrrol-1-yl]-ethoxy}-phenyl)-propionic acid;

(xxix) Triethanolamine salt of (S) 2-Ethoxy-3-(4-{2-[2-methyl-5-(4-methylthiophenyl)-pyrrol-1-yl]-ethoxy}-phenyl)-propionic acid;

(xxx) Ethylenediamine salt of (S) 2-Ethoxy-3-(4-{2-[2-methyl-5-(4-methylthiophenyl)-pyrrol-1-yl]-ethoxy}-phenyl)-propionic acid;

(xxxi) Choline salt of (S) 2-Ethoxy-3-(4-{2-[2-methyl-5-(4-methylthiophenyl)-pyrrol-1-yl]-ethoxy}-phenyl)-propionic acid;

(xxxii) Epolamine salt of (S) 2-Ethoxy-3-(4-{2-[2-methyl-5-(4-methylthiophenyl)-pyrrol-1-yl]-ethoxy}-phenyl)-propionic acid;

(xxxiii) Morpholine 4-(2-hydroxyethyl) salt of (S) 2-Ethoxy-3-(4-{2-[2-methyl-5-(4-methylthiophenyl)-pyrrol-1-yl]-ethoxy}-phenyl)-propionic acid;

(xxxiv) N,N-Diethylethanolamine salt of (S) 2-Ethoxy-3-(4-{2-[2-methyl-5-(4-methylthiophenyl)-pyrrol-1-yl]-ethoxy}-phenyl)-propionic acid;

(xxxv) Deanol salt of (S) 2-Ethoxy-3-(4-{2-[2-methyl-5-(4-methylthiophenyl)-pyrrol-1-yl]-ethoxy}-phenyl)-propionic acid;

(xxxvi) Hydrabamine salt of (S) 2-Ethoxy-3-(4-{2-[2-methyl-5-(4-methylthiophenyl)-pyrrol-1-yl]-ethoxy}-phenyl)-propionic acid;

(xxxvii) Betaine salt of (S) 2-Ethoxy-3-(4-{2-[2-methyl-5-(4-methylthiophenyl)-pyrrol-1-yl]-ethoxy}-phenyl)-propionic acid;

(xxxviii) Ammonia salt of (S) 2-Ethoxy-3-(4-{2-[2-methyl-5-(4-methylthiophenyl)-pyrrol-1-yl]-ethoxy}-phenyl)-propionic acid;

(xxxix) Adamantanamine salt of (S) 2-Ethoxy-3-(4-{2-[2-methyl-5-(4-methylthiophenyl)-pyrrol-1-yl]-ethoxy}-phenyl)-propionic acid;

(xl) 1-Adamantanmethylamine salt of (S) 2-Ethoxy-3-(4-{2-[2-methyl-5-(4-methylthiophenyl)-pyrrol-1-yl]-ethoxy}-phenyl)-propionic acid;

(xli) Tritylamine salt of (S) 2-Ethoxy-3-(4-{2-[2-methyl-5-(4-methylthiophenyl)-pyrrol-1-yl]-ethoxy}-phenyl)-propionic acid;

(xlii) Pyrrolidine salt of (S) 2-Ethoxy-3-(4-{2-[2-methyl-5-(4-methylthiophenyl)-pyrrol-1-yl]-ethoxy}-phenyl)-propionic acid.

13. A pharmaceutical composition comprising a compound of claim 1.

14. A pharmaceutical composition comprising a compound of claim 10.

15. A pharmaceutical composition comprising a compound of claim 11.

16. A pharmaceutical composition comprising a compound of claim 12.

* * * * *